US006372962B1

(12) United States Patent
Baker et al.

(10) Patent No.: US 6,372,962 B1
(45) Date of Patent: Apr. 16, 2002

(54) PATHOGEN RESISTANCE IN PLANTS USING CDNA-N/INTRON CONSTRUCTS

(75) Inventors: Barbara J. Baker, Richmond, CA (US); S. P. Dinesh-Kumar, New Haven, CT (US)

(73) Assignees: The Regents of the University of California, Oakland, CA (US); The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 09/357,206

(22) Filed: Jul. 20, 1999

Related U.S. Application Data

(60) Provisional application No. 60/093,494, filed on Jul. 20, 1998.

(51) Int. Cl.[7] .................................................. H01H 1/00

(52) U.S. Cl. .................... 800/279; 435/320.1; 435/468; 536/23.6; 536/24.1; 800/301; 800/317.1; 800/317.3; 800/317.4

(58) Field of Search ............................. 435/69.1, 320.1, 435/410, 419, 468, 411, 414; 536/23.6, 23.1, 24.1; 800/278, 279, 295, 298, 301, 317, 317.1, 317.3, 317.4

(56) References Cited

U.S. PATENT DOCUMENTS 5,571,706 A 11/1996 Baker et al.

OTHER PUBLICATIONS

Dinesh–Kumar et al, "Alternatively spliced N resistance gene transcripts: Their possible role in tobacco mosaic virus resistance", Feb. 2000, PNAS vol. 97 No. 4, pp. 1908–1913.*

Hehl et al, "TMV resistance gene N homologues are linked to Synchytrium endobioticum resistance in potato" 1999, Theor Appl Genet vol. 98 pp 379–386.*

Sharp, Phillip A., Split Genes and RNA Splicing, *Cell.*, Jun. 17, 1994, pp. 805–815, vol. 77, Cell Press.

Whitham et al., The Product of the Tobacco Mawsaic Virus Resistance Gene N: Similarity to Toll and the Interleukin–1 Receptor, *Cell*, Sep. 23, 1994, pp. 1101–1115, vol. 78, Cell Press.

Lawrence et al., The L6 Gene for Flax Rust Resistance is Related to the Arabidopsis Bacterial Resistance Gene RPS2 and the Tobacco Viral Resistance Gene N, *The Plant Cell*, Aug. 1995, pp. 1195–1206, vol. 7, American Society of Plant Physiologists.

Anderson et al., Inactivation of the Flax Rust Resistance Gene M Associated with Loss of a Repeated Unit Within the Leucine–Rich Repeat Coding Region, *The Plant Cell*, Apr. 1997, pp. 641–651, vol. 9, American Society of Plant Physiologists.

Parker et al., The Arabidopsis Downy Mildew Resistance Gene RPP5 Shares Similarity to the Toll and Interleukin–1 Receptors with N and L6, *The Plant Cell*, Jun. 1997, pp. 879–894, vol. 9, American Society of Plant Physiologists.

* cited by examiner

*Primary Examiner*—Amy J. Nelson
*Assistant Examiner*—Ashwin Mehta
(74) *Attorney, Agent, or Firm*—Alston & Bird LLP

(57) ABSTRACT

Constructs comprising (1) a cDNA molecule corresponding to the tobacco N gene and (2) at least a portion of the third intron of the N gene are disclosed. Such constructs are useful for producing TMV resistance in plants.

23 Claims, No Drawings

PATHOGEN RESISTANCE IN PLANTS USING CDNA-N/INTRON CONSTRUCTS

PRIORITY CLAIM

This application claims priority from co-pending U.S. Provisional Application No. 60/093,494, filed Jul. 20, 1998, which is herein incorporated by reference.

FIELD OF THE INVENTION

This invention relates to nucleic acid molecule useful for producing plants having virus resistance characteristics, and transgenic plants expressing these nucleic acid molecules.

BACKGROUND OF THE INVENTION

Plants are hosts to thousands of infectious diseases caused by a vast array of phytopathogenic fungi, bacteria, viruses, and nematodes. These pathogens are responsible for significant crop losses worldwide, resulting from both infection of growing plants and destruction of harvested crops.

Plants recognize and resist many invading phytopathogens by inducing a rapid defense response, termed the hypersensitive response (HR). HR results in localized cell and tissue death at the site of infection, which constrains further spread of the infection. This local response often triggers non-specific resistance throughout the plant, a phenomenon known as systemic acquired resistance (SAR). Once triggered, SAR provides resistance for days to a wide range of pathogens. The generation of the HR and SAR in a plant depends upon the interaction between a dominant or semi-dominant resistance (R) gene product in the plant and a corresponding dominant avirulence (Avr) gene product expressed by the invading phytopathogen. It has been proposed that phytopathogen Avr products function as ligands, and that plant R products function as receptors. Thus, in the widely accepted model of phytopathogen/plant interaction, binding of the Avr product of an invading pathogen to a corresponding R product in the plant initiates the chain of events within the plant that produces HR and SAR and ultimately leads to disease resistance.

Since the cloning of the first R gene, Pto from tomato, which confers resistance to *Pseudomonas syringae* pv. tomato (Martin et al., 1993), a number of other R genes have been reported (Hammond-Kosack and Jones, 1997). Much effort is currently being directed towards using these genes to engineer pathogen resistance in plants. The production of transgenic plants carrying a heterologous gene sequence is now routinely practiced by plant molecular biologists. Methods for incorporating an isolated gene sequence into an expression cassette, producing plant transformation vectors, and transforming many types of plants are well known. Examples of the production of transgenic plants having modified characteristics as a result of the introduction of a heterologous transgene include: U.S. Pat. No. 5,719,046 to Guerineau (production of herbicide resistant plants by introduction of bacterial dihydropteroate synthase gene); U.S. Pat. No. 5,231,020 to Jorgensen (modification of flavenoids in plants); U.S. Pat. No. 5,583,021 to Dougherty (production of virus resistant plants); and U.S. Pat. No. 5,767,372 to De Greve and U.S. Pat. No. 5,500,365 to Fischoff (production of insect resistant plants by introducing *Bacillus thuringiensis* genes).

In conjunction with such techniques, the isolation of plant R genes has similarly permitted the production of plants having enhanced resistance to certain pathogens. A number of these genes have been used to introduce the encoded resistance characteristic into plant lines that were previously susceptible to the corresponding pathogen. For example, U.S. Pat. No. 5,571,706 to Baker describes the introduction of the N gene into tobacco lines that are susceptible to Tobacco Mosaic Virus (TMV) in order to produce TMV-resistant tobacco plants. WO 95/28423 describes the creation of transgenic plants carrying the Rps2 gene from *Arabidopsis thaliana*, as a means of creating resistance to bacterial pathogens including *Pseudomonas syringae*, and WO 98/02545 describes the introduction of the Prf gene into plants to obtain broad-spectrum pathogen resistance. Cao et al. (1998) describes the introduction into Arabidopsis of the NPR1 cDNA expressed under the control of the 35S promoter to produce enhanced resistance to multiple bacterial pathogens.

The first R gene conferring virus resistance to be isolated from plants was the N gene of *Nicotiana glutinosa* tobacco (Whitham et al., 1994). The N gene (or homologs of this gene) is present in some but not all types of tobacco, and confers resistance to Tobacco Mosaic Virus (TMV). TMV is an important pathogen of not only tobacco, but also of other crop plants including tomato (Lycopersicon sp.) and pepper (Capsicum sp.). A review of the wide range of host species that serve as hosts to TMV is presented in Holmes (1946). TMV is the type virus of the genus Tobamovirus, which includes a number of closely related viral pathogens of commercially important plants. For example, the Tobamovirus group includes tomato mosaic virus, pepper green mottle virus and ondontoglossum ringspot virus, which is a pathogen of orchids (Agrios, 1997).

The *N. glutinosa* N gene is described in detail in U.S. Pat. No. 5,571,706 ("Plant Virus Resistance Gene and Methods") to Baker & Whitham, which is incorporated herein by reference. The sequence of this gene is available on GenBank under accession number U558886. U.S. Pat. No. 5,571,706 discloses the sequence of the N gene, as well as two cDNAs corresponding to the gene. The N gene (including the 5' and 3' regulatory regions) is over 12 kb in length and comprises five exons and four introns, encoding a full length N protein of 1144 amino acids, with a deduced molecular mass of 131.4 kDa. cDNA-N is a cDNA encoded by the N gene; it is approximately 3.7 kb in length and encodes the full length N protein. A second cDNA, cDNA-N-tr, is approximately 3.8 kb in length. It results from an alternative splicing pattern and encodes a truncated protein, N-tr, that is 652 amino acids in length and has a deduced molecular mass of 75.3 kDa. U.S. Pat. No. 5,571,706, and Whitham et al (1994) describe the production of transgenic tobacco plants carrying a full-length N transgene; these plants show the HR response following TMV challenge.

SUMMARY OF THE INVENTION

The inventors have discovered that while the introduction of the full length N gene into a plant results in TMV resistance, introduction of the full length N cDNA (cDNA-N) does not. Neither, it has been discovered, does introduction of cDNA-N-tr or the combination of cDNA-N-tr and cDNA-N. In particular, while plants containing the cDNA sequences exhibit HR in response to a TMV infection, the virus spreads systemically throughout the plants, suggesting that the normal SAR is not triggered.

Use of the shorter cDNA sequences rather than the full gene sequence would be advantageous because the shorter length makes manipulating the sequence easier, and reduces the likelihood that errors will be introduced into the sequence either during laboratory manipulation, or in the plant transformation process. To that end, the inventors have produced a form of the cDNA that does produce TMV resistance when introduced into plants. In this context, TMV resistance refers to the ability of a plant to resist systemic spread of the virus.

The inventors have identified a critical intron region of the N gene that is required for TMV resistance. cDNA-N constructs including this intron region (termed cDNA-N/intron constructs) are able to confer TMV resistance on otherwise susceptible plants. The intron region that is required for a cDNA-N to confer TMV resistance is contained within intron 3 (I13) of the N gene, and includes the 70 base pair alternative exon (AE) that is included within cDNA-N-tr and encodes part of the N-tr protein.

The structural region of the N gene (the sequence of which is shown in Seq. ID No. 1) comprises a series of exons (E) and introns (I) that may be schematically illustrated as follows:

E1-I1-E2-I2-E3-I3-E4-I4-E5 cDNA-N comprises the structural N gene sequence with the introns omitted, and may therefore be represented as:

E1-E2-E3-E4-E5.

The inventors have discovered that inclusion of I13 in the cDNA-N sequence in its naturally occurring position (i.e., between E3 and E4) restores the ability to encode TMV resistance. Thus, one possible cDNA-N/intron construct that may be employed is represented as:

E1-E2-E3-I3-E4-E5 (SEQ ID NO:16)

As discussed in detail below, while inclusion of the entire I3 sequence into a cDNA-N/intron construct is effective to confer TMV resistance, less than the entire I13 sequence may be employed, providing that the 70 base pair AE sequence within I13 is retained and splice acceptor sites for the intron are included. Other sequences may also be included in such constructs, including other N gene introns. For example, one or more of introns I1, I2 and I4, or portions of such sequences, may be added to the construct. Possible combinations include:

E1-I1-E2-E3-I3-E4-E5 (SEQ ID NO:17)

E1-E2-I2-E3-I3-E4-E5 (SEQ ID NO:18)

E1-E2-E3-I3-E4-I4-E5 (SEQ ID NO:19)

E1-I1-E2-I2-E3-I3-E4-E5 (SEQ ID NO:20)

E1-I1-E2-E3-I3-E4-I4-E5 (SEQ ID NO:21)

E1-E2-I2-E3-I3-E4-I4-E5 (SEQ ID NO:22)

In addition to the intron and exon sequences, such constructs require the presence of 5' and 3' regulatory regions. The N gene 5' and 3' regulatory regions may be employed for this purpose, and may be the most effective since they will confer regulatory control on the cDNA-N/intron constructs that is substantially similar to the regulatory control of N gene expression. Other 5' regulatory regions such as the CaMV35S promoter sequence are well known in the art and may also be effective to confer TMV resistance. A number of 3' regulatory regions may be employed, but not all such regions may be effective. For example, it is shown that a construct comprising cDNA-N/intron 3 operably linked at its 5' end to the N gene promoter (p/V) (included within a ca. 4.2 kb 5' regulatory region) and at its 3' end to a ca. 1.3 kb region of the N gene 3' regulatory sequence (3'-GRS) confers resistance to TMV when introduced into otherwise susceptible tobacco plants. In contrast, the same construct in which the 3'-GRS sequence is replaced with the NOS 3' regulatory region does not confer resistance.

Thus, in one embodiment, nucleic acid molecules produced by the inventors comprise cDNA-N with, positioned between the sequences corresponding to exons 3 and 4 of the N gene, the third intron (I3) of the N gene. In another embodiment, the nucleic acid molecule further comprises the 3' regulatory sequence from the N gene (3'-GRS), which regulatory sequence is disclosed herein. While the entire ca. 1.3 kb of 3'-GRS may be employed, less than this entire sequence may also be used in such constructs in order to obtain TMV resistance. The nucleic acid molecule may further comprise the N promoter sequence (pN) contained within the ca. 4.2 kb 5' regulatory region of the N gene, which is also disclosed herein. Again, while the entire ca. 4.2 kb sequence may be employed, less than this entire sequence may also be used in such constructs in order to obtain TMV resistance.

Introduction of the cDNA-N/intron constructs into plants may be used to confer resistance to plant viruses including TMV and other Tobamoviruses, such as tomato mosaic virus, pepper green mottle virus and ondontoglossum ringspot virus. Suitable plant species for transformation with these constructs include solanaceaous plants such as tobacco, tomato, potato and pepper, as well as other plant species, such as orchids, that are host to Tobamoviruses or other plant viruses. Transgenic plants that comprise the disclosed cDNA-N/intron constructs are encompassed by this invention.

SEQUENCE LISTING

Seq. ID No. 1 shows the nucleic acid sequence of the *N. glutinosa* N gene. The sequence comprises the following regions:

| Nucleotides | Feature |
|---|---|
| 1–4281 | 5' regulatory sequence (p/V) |
| 4282–4760 | exon 1 (last codon split between exon 1 and exon 2) |
| 4761–4990 | intron 1 |
| 4991–6086 | exon 2 |
| 6087–6928 | intron 2 |
| 6929–7201 | exon 3 |
| 7202–9019 | intron 3 |
| 9020–10588 | exon 4 |
| 10589–10921 | intron 4 |
| 10922–10939 | exon 5 |
| 10940–12286 | 3' regulatory region (3'-GRS) |

Seq. ID No. 2 shows the nucleic acid sequence of the *N. glutinosa* cDNA-N.

Seq. ID No. 3 shows the amino acid sequence of the *N. glutinosa* N protein.

Seq. ID No. 4 shows the nucleic acid sequence of the *N. glutinosa* cDNA-N-tr.

Seq. ID No. 5 shows the amino acid sequence of the *N. glutinosa* N-tr protein.

Seq. ID No. 6 shows the nucleic acid sequence of the *N. glutinosa* intron 3.

The alternative exon (AE) spans from nucleotides 117–186.

Seq. ID No. 7 shows the nucleic acid sequence of the ca. 1.3 kb *N. glutinosa* 3'-GRS.

Seq. ID No. 8 shows the nucleic acid sequence of the ca. 4.2 kb *N. glutinosa* pN.

Seq. ID No. 9 shows the nucleic acid sequence of pN/cDNA-N/ intron 3/3'-GRS.

Seq. ID No. 10–15 show primers that may be used to amplify N nucleic acids.

DETAILED DESCRIPTION OF THE INVENTION

I. Definitions

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the invention, the following definitions of terms are provided:

N gene: A gene that encodes an N and an N-tr protein, and which when introduced into a plant enhances the resistance of that plant to TMV infection. The prototypical N gene is the gene isolated from *N. glutinosa* and disclosed in U.S. Pat. No. 5,571,706. The sequence of this gene, including 5' and 3' regulatory regions is shown in Seq. ID No. 1). The ability of an N gene to confer TMV resistance may readily be determined by scoring the HR and SAR responses to TMV infection in transgenic plants, and by monitoring systemic spread of the virus, as disclosed below.

The disclosed N gene sequence is designated as the prototypical N gene since it is the first N gene to have been isolated. As discussed in U.S. Pat. No. 5,571,706, functional homologs of this gene from other plant species, such as from other Solanaceous species, may be obtained. Such homologs encode proteins having specified levels of sequence identity with the prototype N protein (e.g., at least 60% sequence identity), and retain N gene function, i.e., retain the ability to confer TMV resistance when introduced into plants. Similarly, the disclosed N and N-tr proteins are the prototypes of such proteins, and homologs of these proteins are encoded by N gene homologs. Accordingly, where reference is made herein to molecules relating to the N gene, for example, cDNA-N, N or N-tr proteins and introns of the N gene (such as I3), it will be understood that such reference includes not only the prototypical sequences of these molecules disclosed herein, but also corresponding sequences from N gene homologs. Also included within the scope of such terms are molecules that differ from the disclosed prototypical molecules by minor variations, such as nucleic acid molecules that vary from the disclosed sequences by virtue of the degeneracy of the genetic code, and nucleic acid sequences that have been modified to encode N or N-tr proteins having conservative amino acid substitutions. Such variant sequences may be produced by manipulating the nucleotide sequence of the tobacco cDNA-N or N gene using standard procedures such as site-directed mutagenesis or the polymerase chain reaction.

N tobacco: A tobacco line that carries at least one copy of an N gene. A plant that is homozygous for the N gene is designated NN, while a plant lacking a functional N gene is designated nn.

N protein/N-tr protein: Proteins encoded by an N gene. The N protein encoded by the prototypical N gene is shown in Seq. ID No. 3. The N-tr protein is a truncated form of the N protein and is encoded by an alternatively spliced form of the N gene; the prototypical sequence of N-tr is shown in Seq. ID No. 5. Expression of both forms of the protein in a plant cell is required for TMV resistance.

cDNA-N: A cDNA molecule that encodes an N protein. The nucleic acid sequence of the prototypical cDNA-N is shown in Seq. ID No. 2.

cDNA-N-tr: A cDNA molecule that encodes an N-tr protein. The nucleic acid sequence of the prototypical cDNA-N-tr is shown in Seq. ID No. 4.

cDNA-N/intron: A construct comprising a cDNA-N molecule and all or part of one or more N gene introns.

cDNA-N/intron 3: A construct comprising a cDNA-N molecule and all or part of an N gene intron 3 (I3) sequence (described in more detail below). The I3 sequence is typically situated in the cDNA at a position corresponding to the position of the intron in the N gene (i.e., between codons encoding Lys 616 and His 617 of the N protein).

N intron: An intron of an N gene. The prototypical N gene has four introns, I1, I2, I3 and I4. The sequences of these introns from the prototypical N gene are shown in Seq. ID No. 1. As discussed above, the invention may be practiced using these sequences or homologs of these sequences from N gene homologs, or variants on these sequences. The I3 intron is particularly relevant to the invention since it is the intron that is incorporated into cDNA-N/intron constructs to confer TMV resistance. While the entire I3 sequence as shown in Seq. ID No. 6 may be employed for this purpose, the biological activity of cDNA-N/intron constructs (i.e., enhancing TMV resistance) may also be obtained using less than the entire sequence. Reference to intron 3 (or I3) thus encompasses not only the entire intron 3 sequence of the prototypical N gene and its homologs and variants on this sequence, but also sequences that comprise less than the entire intron 3 sequence. At a minimum, the portion of the I3 sequence that is incorporated into cDNA-N/intron constructs is the alternative exon (AE) comprising nucleotides 117–186 of Seq. ID No. 6 and splice acceptor and donor sites. The splice two pairs of acceptor and donor sites for the AE within intron 3 comprise nucleotides 7200–7203 and 7316–7319 and 7386–7389 and 9018–9021 of Seq. ID No. 1. These sequences are quite similar to the consensus splice acceptor and donor sequences. In some other systems in which alternative splicing of exons has been reported, in addition to the splice acceptor and donor sites, a cis acting sequence is required. For example, two cis elements (GAAGAAGA and CAAGG) within the fibronectin AE modulate the exclusion or inclusion of the AE (Caputi et al. 1994). Sequences similar to these are located within the intron 3 AE of N and will be included within any intron 3 construct that is employed. TMV resistance may be obtained by including a greater portion of the I3 sequence, such as splice acceptor and donor sites together with nucleotides 100–200, 80–250, 50–300, or 1–500 or 1–1000 of Seq. ID No. 6, or indeed the entire I3 sequence. As described in Example 2 below, the pN/cDNA-N/intron 3/3'-GRS construct depicted in Seq. ID No. 9 confers TMV resistance in trangenic plants. Thus, in the context of this construct, the I3 sequence may be said to be biologically active (i.e., the construct produced TMV resistance when introduced into plants). One of skill in the art will be able to ascertain whether a particular sub-regions of an I3 confer biological activity by substituting such sequences for the I3 sequence in the cDNA-N/intron 3/3'-GRS construct, introducing the resulting sequence into plants and assessing resultant TMV resistance by analyzing HR and SAR responses, or by determining systemic spread of the virus. Accordingly, the term "biologically active intron 3" refers to an intron 3 of an N gene, or a portion or variant of such an intron that, when incorporated into a pN/cDNA-N/intron 3/3'-GRS construct, and introduced into a plant, results in TMV resistance.

3'-GRS: The 3' regulatory sequence of an N gene. The 3'-GRS of the prototypical N gene from tobacco is depicted in Seq. ID No. 7. For incorporation into cDNA-N/intron constructs, the entire 3'-GRS sequence shown in Seq. ID No. 7 (ca. 1.3 kb), or less than the entire sequence, may be utilized. As described in Example 2 below, a construct comprising pN/cDNA-N/intron 3 operably linked to the ca. 1.3 kb 3'-GRS sequence (the sequence of which is depicted in Seq. ID No. 9) confers TMV resistance in transgenic tobacco plants. Thus, in the context of this construct, the 1.3 kb 3'-GRS sequence may be said to be biologically active (i.e., the construct produced TMV resistance), whereas the NOS 3' regulatory sequence in the context of the same construct does not have biological activity. One of skill in the art will be able to ascertain whether a particular sub-region of the 3'-GRS confers biological activity by incorporating such sequences into a cDNA-N/intron 3 construct, introducing the resulting sequence into plants and assessing resultant TMV resistance by analyzing HR and SAR responses, or determining whether systemic virus spread occurs. For example, a 3' regulatory sequence comprising nucleotides 1–100, 1–150, 1–200, 1–500 or 1–1000 of the sequence shown in Seq. ID No. 7 may be utilized in a cDNA-N/intron 3 construct, and the degree to which such a construct enhances TMV resistance ascertained by the methods described herein. In addition, 3' regulatory sequences from N gene homologs may also be employed. Thus, the term “biologically active 3'-GRS” refers to a 3' regulatory region of an N gene, or a part or a variant of such a region, that, when operably linked to the 3' end of a pN/cDNA-N/intron 3 construct and introduced into a plant results in TMV resistance.

pN: The promoter region of an N gene. The pN of the prototypical N gene is depicted in Seq. ID No. 8. For incorporation into cDNA-N/intron constructs, the entire pN sequence shown in Seq. ID No. 8 (ca. 4.2 kb), or less than the entire sequence, may be utilized. As described in Example 2 below, a construct comprising the ca. 4.2 kb pN operably linked to the cDNA-N/intron/3'-GRS sequence (the sequence of which construct is depicted in Seq. ID No. 9) confers TMV resistance in transgenic tobacco plants. Thus, in the context of this construct, the ca. 4.2 kb pN sequence may be said to be biologically active (i.e., the construct produced TMV resistance). One of skill in the art will be able to ascertain whether a particular sub-region of pN confers biological activity by incorporating such sequences into a cDNA-N/intron 3/3'-GRS construct, introducing the resulting sequence into plants and assessing resultant TMV resistance by analyzing HR and SAR responses, or determining whether systemic virus spread occurs. For example, a 5' regulatory sequence comprising nucleotides 4000–4281, 3500–4281, 2500–4281 or 2000–4281 of the sequence shown in Seq. ID No. 8 may be utilized in a cDNA-N/intron 3 construct, and the degree to which such a construct enhances TMV resistance ascertained by the methods described herein. In addition, 5'regulatory sequences from N gene homologs may also be employed. Thus, the term “biologically active pN” refers to a 5' regulatory region of an N gene, or a part or a variant of such a region, that, when operably linked to the 5' end of a cDNA-N/intron 3/3'-GRS construct and introduced into a plant results in TMV resistance.

N exon: An exon of an N gene. The prototypical N gene has five exons, E1, E2, E3, E4, and E5.

Sequence identity: The similarity between two nucleic acid sequences, or two amino acid sequences is expressed in terms of the similarity between the sequences, otherwise referred to as sequence identity. Sequence identity is frequently measured in terms of percentage identity (or similarity or homlogy); the higher the percentage, the more similar the two sequences are. Homologs of the prototype N and N-tr proteins will possess a relatively high degree of sequence identity when aligned using standard methods.

Methods of alignment of sequences for comparison are well known in the art. Various programs and alignment algorithms are described in: Smith and Waterman (1981); Needleman and Wunsch (1970); Pearson and Lipman (1988); Higgins and Sharp (1988); Higgins and Sharp (1989); Corpet et al. (1988); Huang et al. (1992); and Pearson et al. (1994). Altschul et al. (1994) presents a detailed consideration of sequence alignment methods and homology calculations.

The NCBI Basic Local Alignment Search Tool (BLAST) (Altschul et al., 1990) is available from several sources, including the National Center for Biotechnology Information (NCBI, Bethesda, Md.) and on the Internet, for use in connection with the sequence analysis programs blastp, blastn, blastx, tblastn and tblastx.

Homologs of the disclosed prototype N and N-tr protein are typically characterized by possession of at least 60% sequence identity counted over the full length alignment with the amino acid sequence of the prototype using the NCBI Blast 2.0, gapped blastp set to default parameters. Proteins with even greater similarity to the reference sequences will show increasing percentage identities when assessed by this method, such as at least 70%, at least 75%, at least 80%, at least 90% or at least 95% of sequence identity. When less than the entire sequence is being compared for sequence identity, homologs will typically possess at least 75% sequence identity over short windows of 10–20 amino acids, and may possess sequence identities of at least 85% or at least 90% or 95% depending on their similarity to the reference sequence. Methods for determining sequence identity over such short windows are described at the NCBI Internet site. One of skill in the art will appreciate that these sequence identity ranges are provided for guidance only; it is entirely possible that strongly significant homologs could be obtained that fall outside of the ranges provided.

Nucleic acid hybridization: Another indication that two nucleic acid sequences share a high degree of similarity, for example, 50% or greater, is that the two molecules hybridize to each other under defined hybridization conditions. The defined hybridization conditions may be more or less stringent, with more stringent conditions allowing less non-specific binding, i.e., binding between pairs of nucleic acid probes that are not perfectly matched.

Because the degree to which two nucleic acids will bind is dependent upon their sequences, stringency is sequence dependent. Generally, stringency of hybridization is expressed with reference to the temperature under which the wash step is carried out. Generally, such wash temperatures are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. An equation for calculating $T_m$ and conditions for nucleic acid hybridization is well known and can be found in Sambrook et al., 1989, Molecular Cloning: A Laboratory Manual, $2^{nd}$ ed., vol. 1–3, Cold Spring Harbor, N.Y.; specifically see volume 2, chapter 9.

Conditions for hybridization between nucleotides of the present invention (e.g., between two nucleotides showing substantial similarity) include wash conditions of 70° C. and about 0.2×SSC for 1 hour, or alternatively, 65° C., 60° C., or 55° C. and about 0.2 to 2×SSC (with, for instance, about 0.1% SDS) for 1 hour. Typically, blocking reagents are used to block non-specific hybridization. Such blocking reagents include, for instance, salmon sperm DNA. Hybridization, particularly under highly stringent conditions (e.g., Wash temperatures of 60° C. or more and SSC concentrations of 0.2×) is suggestive of evolutionary similarity between the nucleotides. Such similarity (whether produced by convergent or divergent evolution) is strongly indicative of a similar role for the nucleotides and their resultant proteins.

Nucleic acid sequences that do not show a high degree of identity may nevertheless encode similar amino acid sequences due to the degeneracy of the genetic code. It is understood that changes in nucleic acid sequence can be made using this degeneracy to produce multiple nucleic acid sequence that all encode substantially the same protein.

Oligonucleotide: A linear polynucleotide sequence of up to about 100 nucleotide bases in length.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Isolated: An "isolated" biological component (such as a nucleic acid or protein or organelle) has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Purified: The term purified does not require absolute purity; rather, it is intended as a relative term. Thus, for example, a purified N protein preparation is one in which the N protein is more enriched than the protein is in its natural environment within a plant cell. Generally, a preparation of N protein is purified such that the N protein represents at least 5% of the total protein content of the preparation. For particular applications, higher purity may be desired, such that preparations in which the N protein represents at least 20% or at least 50% of the total protein content may be employed.

Ortholog: Two nucleotide or amino acid sequences are orthologs of each other if they share a common ancestral sequence and diverged when a species carrying that ancestral sequence split into two species. Orthologous sequences are also homologous sequences.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

cDNA (complementary DNA): A piece of DNA lacking internal, non-coding segments (introns) and regulatory sequences that determine transcription. cDNA is synthesized in the laboratory by reverse transcription from messenger RNA extracted from cells.

ORF (open reading frame): A series of nucleotide triplets (codons) coding for amino acids without any termination codons. These sequences are usually translatable into a peptide.

Transgenic plant: As used herein, this term refers to a plant that contains recombinant genetic material not normally found in plants of this type and which has been introduced into the plant in question (or into progenitors of the plant) by human manipulation. Thus, a plant that is grown from a plant cell into which recombinant DNA is introduced by transformation is a transgenic plant, as are all offspring of that plant that contain the introduced transgene (whether produced sexually or asexually).

II. Production of cDNA-Intron Constructs

The prototypical cDNA-N sequence may be amplified by the polymerase chain reaction (PCR) from a suitable cDNA library (e.g., one produced from TMV-infected N tobacco plants) or directly from TMV infected N tobacco plant cells by reverse transcription PCR (RT-PCR). The pN, I3 and 3' regulatory sequences of this N gene may similarly be amplified directly from N tobacco genomic DNA, or from a genomic library of N tobacco. Methods and conditions for both direct PCR and RT-PCR are known in the art and are described in Innis et al. (1990).

The selection of PCR primers will be made according to the portions of cDNA-N (or the N gene) that are to be amplified. Primers may be chosen to amplify small segments of the CDNA, the open reading frame, all or part of the intron 3 sequence, all or part of the 1.3 kb 3' regulatory sequence, all or part of the 4.2 kb 5' regulatory sequence, all or part of the cDNA molecule or all or part of the N gene sequence. Variations in amplification conditions may be required to accommodate primers of differing lengths; such considerations are well known in the art and are discussed in Innis et al. (1990), Sambrook et al. (1989), and Ausubel et al (1992). By way of example only, the cDNA-N molecule as shown in Seq. ID No. 2 may be amplified using the following combination of primers:

Primer 1 5'GGCACGAGATTTTTTCACATACAG 3' (Seq. ID No. 10)

Primer 2 5'AAGTAATATAGAGATGTTATTAC 3' (Seq. ID No. 11)

The open reading frame portion of cDNA-N may be amplified using the following primer pair:

Primer 3 5'ATGGCATCTTCTTCTTCTTCTTCTA-GATGG 3' (Seq. ID No. 12)

Primer 4 5'CCCATTGATGAGCTCATAAAAGGAAGT-TCT 3' (Seq. ID No. 13)

And the I3 sequence of the N gene may be amplified with the following primer pair:

Primer 5 5'GTACAATAGCTTGAATTCTATTTTGTTG 3 (Seq. ID No. 14)

Primer 6 5'CTGTTTAGAACACAGACAGAATGAGAA 3' (Seq. ID No. 15)

These primers are illustrative only; it will be appreciated by one skilled in the art that many different primers may be derived from the cDNA-N and N gene sequences in order to amplify particular regions of these molecules. Resequencing of PCR products obtained by these amplification procedures is recommended; this will facilitate confirmation of the amplified sequence and will also provide information on natural variation on the sequences in different ecotypes and plant populations.

PCR primers may also be designed having terminal restriction endonuclease sites to facilitate cloning of amplified products. Incorporation of the I3 sequence into the amplified cDNA-N may be achieved by making use of restriction sites within cDNA-N as described in Example 2 below. Similarly, regulatory sequences such as pN and 3'-GRS may be incorporated into the constructs using standard molecular biology techniques.

III. Obtaining N Homologs and Sequence Variants

The description of methods for producing cDNA-N/intron constructs above uses the example of the prototypical N gene and cDNA sequences. As discussed above, the terms N gene, cDNA-N, cDNA-N-tr, pN, I3 and 3'-GRS, and N and N-tr encompass not only the prototypical forms of these molecules but also homologs and variants that differ in exact sequence from the disclosed prototype sequences.

N Homologs

Homologs of the N gene are present in a number of plant species including tomato and other varieties of tobacco. Such homologs may also be used to produce cDNA-N/intron constructs. As described above, homologs of the disclosed N gene confer TMV resistance when introduced into otherwise susceptible plants and encode N and N-tr that are typically characterized by possession of at least 60% sequence identity counted over the full length alignment with the amino acid sequence of the prototype N and N-tr sequences using the NCBI Blast 2.0, gapped blastp set to default parameters. Proteins with even greater similarity to the reference sequences will show increasing percentage identities when assessed by this method, such as at least 70%, at least 75%, at least 80%, at least 90% or at least 95% sequence identity.

Both conventional hybridization and PCR amplification procedures may be utilized to clone sequences encoding N and N-tr homologs. Common to both of these techniques is the hybridization of probes or primers derived from the prototype cDNA-N or N gene sequence to a target nucleotide preparation, which may be, in the case of conventional hybridization approaches, a cDNA or genomic library or, in the case of PCR amplification, a cDNA or genomic library, or an mRNA preparation. Amplification of, or hybridization to, a cDNA library in order to obtain N homologs should preferably be performed on a cDNA library made from a plant infected with TMV so that the N homolog is actively expressed in the cells from which the library is made.

Direct PCR amplification may be performed on cDNA or genomic libraries prepared from the plant species in question, or RT-PCR may be performed using mRNA extracted from the plant cells using standard methods. PCR primers will comprise at least 15 consecutive nucleotides of the tobacco cDNA-N or N gene. One of skill in the art will appreciate that sequence differences between the tobacco cDNA-N or N gene and the target nucleic acid to be amplified may result in lower amplification efficiencies. To compensate for this, longer PCR primers or lower annealing temperatures may be used during the amplification cycle. Where lower annealing temperatures are used, sequential rounds of amplification using nested primer pairs may be necessary to enhance specificity.

For conventional hybridization techniques the hybridization probe is preferably conjugated with a detectable label such as a radioactive label, and the probe is preferably of at least 20 nucleotides in length. As is well known in the art, increasing the length of hybridization probes tends to give enhanced specificity. The labeled probe derived from the tobacco cDNA-N or N gene sequence may be hybridized to a plant cDNA or genomic library and the hybridization signal detected using means known in the art. The hybridizing colony or plaque (depending on the type of library used) is then purified and the cloned sequence contained in that colony or plaque isolated and characterized.

Homologs of the tobacco cDNA-N or N gene may alternatively be obtained by immunoscreening of an expression library. With the provision of the disclosed N gene and encoded proteins, the N or N-tr proteins may be expressed and purified in a heterologous expression system (e.g., *E. coli*) and used to raise antibodies (monoclonal or polyclonal) specific for the N or N-tr protein. Antibodies may also be raised against synthetic peptides derived from the tobacco N or N-tr amino acid sequences. Methods of raising antibodies are well known in the art and are described in Harlow and Lane (1988). Such antibodies can then be used to screen an expression cDNA library produced from the plant from which it is desired to clone the N homolog using routine methods. The selected cDNAs can be confirmed by sequencing and enzyme activity.

Variant Sequences

Variant N and N-tr proteins include proteins that differ in amino acid sequence from the prototypical N and N-tr sequences. Such proteins may be produced by manipulating the nucleotide sequence of the prototype N cDNAs or N gene using standard procedures such as site-directed mutagenesis or the polymerase chain reaction. The simplest modifications involve the substitution of one or more amino acids for amino acids having similar biochemical properties. These so-called conservative substitutions are likely to have minimal impact on the activity of the resultant protein. Table 1 shows amino acids that may be substituted for an original amino acid in a protein and which are regarded as conservative substitutions.

TABLE 1

| Original Residue | Conservative Substitutions |
|---|---|
| Ala | ser |
| Arg | lys |
| Asn | gln, his |
| Asp | glu |
| Cys | ser |
| Gln | asn |
| Glu | asp |
| Gly | pro |
| His | asn; gln |
| Ile | leu, val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

More substantial changes in biological function or other features may be obtained by selecting substitutions that are less conservative than those in Table 1, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions which in general are expected to produce the greatest changes in protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine. The effects of these amino acid substitutions or deletions or additions may be assessed for N derivatives by analyzing the ability of the N gene encoding the derivative proteins to confer TMV resistance on transgenic plants.

Variant N cDNAs or N genes may be produced by standard DNA mutagenesis techniques, for example, M13 primer mutagenesis. Details of these techniques are provided in Sambrook et al. (1989), Ch. 15. By the use of such techniques, variants may be created which differ in minor ways from the prototypical N nucleic acid sequences, yet which still retain N gene function. In their simplest form, such variants may differ from the disclosed sequences by alteration of the coding region to fit the codon usage bias of the particular organism into which the molecule is to be introduced.

Alternatively, the coding region may be altered by taking advantage of the degeneracy of the genetic code to alter the coding sequence in such a way that, while the nucleotide sequence is substantially altered, it nevertheless encodes proteins having amino acid sequences identical or substantially similar to the prototype N and N-tr sequences. For example, the second amino acid residue of the prototype N protein is alanine. This is encoded in the prototype N gene open reading frame (ORF) by the nucleotide codon triplet GCA. Because of the degeneracy of the genetic code, three other nucleotide codon triplets—GCT, GCC and GCG—also code for alanine. Thus, the nucleotide sequence of the N ORF could be changed at this position to any of these three codons without affecting the amino acid composition of the encoded protein or the characteristics of the protein. Based upon the degeneracy of the genetic code, variant DNA molecules may be derived from the N cDNA and gene sequences using standard DNA mutagenesis techniques as described above, or by synthesis of DNA sequences.

IV. Introduction of cDNA-Intron Constructs into Plants

Once a cDNA (or gene) encoding a protein involved in the determination of a particular plant characteristic has been isolated, standard techniques may be used to express the cDNA in transgenic plants in order to modify that particular plant characteristic. The basic approach is to clone the cDNA into a transformation vector, such that it is operably linked to control sequences (e.g., a promoter) that direct expression of the cDNA in plant cells. The transformation vector is then introduced into plant cells by one of a number of techniques (e.g., electroporation) and progeny plants containing the introduced cDNA are selected. Preferably all or part of the transformation vector will stably integrate into the genome of the plant cell. That part of the transformation vector which integrates into the plant cell and which contains the introduced cDNA and associated sequences for controlling expression (the introduced "transgene") may be referred to as the recombinant expression cassette.

Selection of progeny plants containing the introduced transgene may be made based upon the detection of an altered phenotype. Such a phenotype may result directly from the cDNA cloned into the transformation vector or may be manifested as enhanced resistance to a chemical agent (such as an antibiotic) as a result of the inclusion of a dominant selectable marker gene incorporated into the transformation vector.

Successful examples of the modification of plant characteristics by transformation with cloned nucleic acid sequences are replete in the technical and scientific literature. Selected examples, which serve to illustrate the knowledge in this field of technology include:

U.S. Pat. No. 5,571,706 ("Plant Virus Resistance Gene and Methods");

U.S. Pat. No. 5,677,175 ("Plant Pathogen Induced Proteins");

U.S. Pat. No. 5,510,471 ("Chimeric Gene for the Transformation of Plants");

U.S. Pat. No. 5,750,386 ("Pathogen-Resistant Transgenic Plants");

U.S. Pat. No. 5,597,945 ("Plants Genetically Enhanced for Disease Resistance");

U.S. Pat. No. 5,589,615 ("Process for the Production of Transgenic Plants with Increased Nutritional Value Via the Expression of Modified 2S Storage Albumins");

U.S. Pat. No. 5,750,871 ("Transformation and Foreign Gene Expression in Brassica Species"); and U.S. Pat. No. 5,268,526 ("Overexpression of Phytochrome in Transgenic Plants").

These examples include descriptions of transformation vector selection, transformation techniques and the construction of constructs designed to over-express the introduced cDNA. In light of the foregoing and the provision herein of cDNA-N/intron constructs, it is thus apparent that one of skill in the art will be able to introduce these constructs into plants in order to produce plants having TMV resistance. Expression of cDNA-N/intron constructs in plants that are otherwise sensitive to TMV, will be useful to confer resistance to this and possibly other viruses.

A. Plant Types

Viruses infect many plant species, and TMV in particular is a serious pathogen of Solanaceous species such as tobacco (Nicotiana sp.), tomato (Lycopersicn sp.) and pepper (Capsicum sp.) and is able to infect potato (Solanum sp.). cDNA-N/intron 3 constructs as described herein are expected to be effective against not only TMV, but also other viruses, including other Tobamoviruses. Closely related Tobamoviruses include tomato mosaic virus and pepper green mottle virus, and it is known that expression of the N gene in tomato confers resistance to tomato moaic virus. Thus, cDNA-N/intron constructs may be usefully expressed in a wide range of higher plants to confer resistance to viral diseases, both monocotyledonous and dicotyledenous plants, including, but not limited to maize, wheat, rice, barley, soybean, cotton, beans in general, rape/canola, alfalfa, flax, sunflower, safflower, brassica, cotton, flax, peanut, clover; vegetables such as lettuce, tomato, cucurbits, cassava, potato, carrot, radish, pea, lentils, cabbage, cauliflower, broccoli, Brussels sprouts, peppers; tree fruits such as citrus, apples, pears, peaches, apricots, walnuts; and flowers such as orchides, carnations and roses.

B. Vector Construction

A number of recombinant vectors suitable for stable transfection of plant cells or for the establishment of transgenic plants have been described including those described in Pouwels et al., (1987), Weissbach and Weissbach, (1989), and Gelvin et al., (1990). Typically, plant transformation vectors include one or more cloned plant genes (or cDNAs) under the transcriptional control of 5' and 3' regulatory sequences and a dominant selectable marker. The selection of suitable 5' and 3' regulatory sequences for the cDNA-N/intron constructs is discused above. Dominant selectable marker genes that allow for the ready selection of transformants include those encoding antibiotic resistance genes (e.g., resistance to hygromycin, kanamycin, bleomycin, G418, streptomycin or spectinomycin) and herbicide resistance genes (e.g., phosphinothricin acetyltransferase).

C. Transformation and Regeneration Techniques

Transformation and regeneration of both monocotyledonous and dicotyledonous plant cells is now routine, and the appropriate transformation technique will be determined by the practitioner. The choice of method will vary with the type of plant to be transformed; those skilled in the art will recognize the suitability of particular methods for given plant types. Suitable methods may include, but are not limited to: electroporation of plant protoplasts; liposome-mediated transformation; polyethylene glycol (PEG) mediated transformation; transformation using viruses; micro-injection of plant cells; micro-projectile bombardment of plant cells; vacuum infiltration; and Agrobacterium tumefaciens (AT) mediated transformation. Typical procedures for transforming and regenerating plants are described in the patent documents listed at the beginning of this section.

D. Selection of Transformed Plants

Following transformation and regeneration of plants with the transformation vector, transformed plants are usually selected using a dominant selectable marker incorporated into the transformation vector. Typically, such a marker will confer antibiotic resistance on the seedlings of transformed plants, and selection of transformants can be accomplished by exposing the seedlings to appropriate concentrations of the antibiotic.

After transformed plants are selected and grown to maturity, they can be assayed using the methods described herein to determine whether the susceptibility of the plant to TMV infection has been altered as a result of the introduced cDNA-N/intron construct.

EXAMPLES

The following Examples are illustrative of the invention:

Example 1

The N gene, but Neither cDNA-N nor cDNA-N-tr, Confers TMV Resistance in Transgenic Plants cDNA-N and cDNA-N-tr were cloned into the T-DNA vector pOCA28 (Olszewski et al., 1988; gift from F. Ausubel, Harvard Medical School). The resulting vectors were transformed into TMV suceptible tobacco (SR1::nn) by Agrobacterium-mediated transformation (Horsch et al., 1985). The lower leaves of T0 transformants were inoculated with TMV (U1 strain) 3–4 weeks after transfer to soil as described by Takahashi (1956) and Klement (1990). Following such inoculation, resistance or susceptibility of a plant to TMV may be assessed using a number of standard tests, including determining HR and SAR responses, and detecting the presence of TMV in the upper leaves of the plant.

With respect to HR, the inoculated leaves of a resistant plant will show localized regions of necrosis around the site of infection within about 48 hours after inoculation; the lesions are generally about 0.1 cm in diameter and TMV is restricted to the region immediately surrounding the necrotic lesions. In contrast, leaves of susceptible plants generally show no lesions, the TMV spreads systemically, and the leaves develop mosaic symptoms characterized by intermittent areas of light and dark leaf tissue.

The SAR response is generally determined about 7–10 days after inoculation of the lower leaves, by inoculating upper leaves of the plant in the same manner. A resistant plant in which the SAR has been triggered by the earlier inoculation will show HR lesions on these upper leaves within about 48 hours of the second inoculation, but the lesions are typically fewer and significantly smaller (0.03–0.05 cm diameter) than the HR lesions on the lower leaves. A susceptible plant will again show no lesions, and the mosaic patterning signifying systemic infection will be observed on the upper leaves.

Systemic spread of the virus can be detected in a number of ways. By visual inspection of the leaves, systemic infection can be detected by the appearance of the mosaic light and dark patches on the leaves away from the site of the initial inoculation. The presence of systemically spread virus can also be detected by a bioassay in which leaves of the inoculated test plant (taken from a part of the test plant distal from the initial inoculation ("distal leaves")) are rubbed onto an indicator plant (e.g., *N. tabacum* Sansum NN). The development of an HR response on the indicator plant indicates the presence of systemic spread of the virus through the test plant. Additionally, systemic spread of the virus may be detected at the molecular level by removing distal leaves, extracting RNA using standard procedures and performing a Northern blot using a radiolabeled probe derived from the TMV genome. In this test, systemic spread is indicated by the presence of TMV-hybridizing bands on the Northern blot. Alternatively, systemic spread of the virus may be detected immunologically, for example by ELISA of protein extracted from distal leaves using an anti-TMV protein antibody.

With development of a resistance response (localized HR and containment of virus to the infection site) or susceptible response (mosaic and systemic spread of the virus) to TMV was observed. T1 progeny were analyzed to confirm transmission of phenotypes into the next generation.

The development of a resistance response (localized HR and containment of virus to the infection site) or susceptible response (mosaic and systemic spread of the virus) to TMV was determined using these assay methods in both the T0 and T1 generations. Expression of the N gene driven by its native N promoter and linked to the N 3' end in the SR1::nn plants produced TMV resistance phenotype similar to that of Samsun NN plants, i.e., induction of HR lesions (about 0.1 cm in diamenter) and containment of the virus to the infection site. In contrast, expression of the cDNA-N under 35S (constitutive) or N (native) promoter and linked to a NOS terminator leads to large HR lesions (up to 0.5 cm diameter vs. 0.1 cm for wild type N plants) in SR1::nn tobacco plants at the site of TMV infection after 10 days (compared to 2 days in resistant wild type N plants). Appearance of HR lesion is accompanied by spread of the virus into systemic leaves leading to mosaic symptoms with punctate HR lesions. Expression of the cDNA-N-tr in SR1::nn does not lead to induction of any HR and TMV spreads systemically and results in mosaic symptoms. Plants that contain both cDNAs show the same phenotype as plants transformed with cDNA-N alone. These results demonstrate that neither the cDNA-N nor the cDNA-N-tr confers TMV resistance alone or in combination.

Based on these results it was hypothesized that the 3' region of the N gene may have an effect on the expression of the N cDNAs. Therefore, the N-cDNA was expressed under the control of the native N promoter and linked to the 3' regulatory region of the N gene. Plants expressing these constructs respond to TMV infection with an HR phenotype within 2 days, similar to the wild type N gene-containing plants. However, the HR is insufficient to inhibit spread of TMV—HR continues to spread throughout the plant and results in death within 10–15 days post infection.

Example 2 cDNA-N/Intron 3 Constructs Confer Full TMV Resistance In Transgenic Plants

A. Introns 1, 2 and 4 are Dispensible for N Function:

To determine the minimum DNA sequence in the N gene that is required to confer the resistance response to TMV infection, various intron deletion constructions in the N gene were created. To delete intron 1 (bases 4761–4990) from the N genomic clone, the XbaI-SphI (bases 81–1383) DNA fragment from the N cDNA was cloned into XbaI-SphI-restricted N gene. To delete intron 2 (bases 6087–6928) from the N genomic clone, the SphI-SalI (bases (1383–1758) DNA fragment from N cDNA was cloned into SphI-SalI-restricted N gene. To delete intron 4 (bases 10589–10921) from the N genomic clone, the AgeI-SacI (bases 2973–3482) DNA fragment was cloned into AgeI-SacI-restricted N gene. These N gene intron deletion DNA fragments were cloned into T-DNA vector pOCA28 and transformed into TMV susceptible tobacco SR1::nn. T0 transformants and T1 selfed progenies were inoculated with TMV (U1 strain) 3–4 weeks after transfer to soil as described (Takahashi, 1956; Klement, 1990). The development of resistance response or suceptible response to TMV was observed as described in the previous example. These assays indicated that the deletion of introns 1, 2 or 4 did not affect the resistance response to TMV. All plants transformed with these constructs showed a resistance response similar to that of N gene-containing plants.

B. AE is Required For Resistance:

Based on these results and the observation that cDNA-N does not confer resistance, it was proposed that the alternative exon (AE) that is present in the intron 3 may be important for the proper function of the N gene. To test the importance of AE in gene function, the AE and the flanking splice sites were deleted from the N gene. The AE and flanking splice sites (bases 7316–7389) were deleted from the N gene by PCR. An upstream primer that anneals to bases 7034–7054 in the N gene and a downstrem primer that anneals to bases 7315–7300 in the N gene were used to generate a PCR fragment of 280 bp. This 280 bp PCR fragment was used as an upstream primer along with a downtream primer that anneals to bases 9051–9030 in the N gene were used to amplify a fragment of 2016 bp. The 2016 bp PCR fragment was restricted with SalI-BglII and cloned into the N gene restricted with same enzymes. The AE and flanking splice site deleted DNA fragment was cloned into T-DNA vector pOCA28 and transformed into TMV susceptible tobacco SR1::nn. T0 transformants and T1 selfed progenies were inoculated with TMV (U1 strain) 3–4 weeks after transfer to soil as described (Takahashi, 1956; Klement, 1990). The development of resistance response or suceptible response to TMV was observed as described in the previous example. These plants respond to TMV infection with HR phenotype within 2 days, similar to the wild type N gene-containing plants. However, the HR is insufficient to inhibit spread of TMV. HR continues to spread throughout the plant and results in death within 10–15 days post infection. This result indicates that the AE generated by alternative splicing is required for proper N gene function.

C. The Addition of Intron 3 to cDNA-N Partially Restores Resistance:

Based on these results, it was proposed that the intron 3 that contains the AE is critical for proper N gene function. To test this a cDNA-N with intron 3 was constructed under control of the native N promoter and linked to a NOS terminator by first cloning the XbaI-SacI fragment (bases 81–3482 of Seq. ID No. 1) from N cDNA into XbaI-SacI-restricted N gene, resulting in the plasmid SPDK400. To introduce the NOS terminator, the EcoICRI-EcoRI-restricted fragment filled in with klenow enzyme containing the NOS terminator from the pBI221 plasmid (CLONTEC, Palo Alto, Calif.) was cloned into AatII-restricted, klenow enzyme filled-in SPDK400. The cDNA-N with intron III under its native N promoter and linked to a NOS terminator DNA fragment was then cloned into T-DNA vector pOCA28 and transformed into TMV susceptible tobacco SR1::nn. T0 transformants and T1 selfed progenies were inoculated with TMV (U1 strain) 3–4 weeks after transfer to soil as described (Takahashi, 1956; Klement, 1990). The development of resistance or susceptibility responses to TMV was observed as described in the previous example. These plants responded to TMV infection with HR phenotype within 2 days, similar to the wild type N gene-containing plants. However, the HR is insufficient to inhibit spread of TMV. HR continues to spread throughout the plant and results in death within 10–15 days post infection. This result indicates that the AE is required for N function and in addition the 3'-GRS of the N gene may be required for proper N function.

D. pN/cDNA-N/intron 3/3'-GRS Confers Complete Resistance:

To test the effect of the AE and 3'-GRS on the cDNA-N function, the pN/cDNA-N/intron 3/3'-GRS construct depicted in Seq. I.D No. 9 was constructed. To generate this construct, the XbaI-SacI DNA fragment from the N cDNA (bases 81–3482) was cloned into XbaI-SacI-restricted N gene. The cDNA-N with intron 3 under its native N promoter and linked to a 3' RS of the N gene was cloned into T-DNA vector pOCA28 and transformed into TMV susceptible tobacco SR1::nn. T0 transformants and T1 selfed progenies were inoculated with TMV (U1 strain) 3–4 weeks after transfer to soil as described (Takahashi, 1956; Klement, 1990). The development of resistance or susceptibility responses to TMV was observed as described in the previous example. The results showed that plants transformed with the the pN/cDNA-N/intron 3/3'-GRS construct were able to mount complete resistance in response to TMV infection, including HR, SAR and inhibition of systemic spread of the virus.

E. Molecular Analysis of mRNA-N and mRNA-N-tr in N Gene Containing Tobacco Plants:

In order to detemine if mRNA-N and mRNA-N-tr are generated in vivo in the wild type N gene containing tobacco plants, quantitative reverse trancription PCR experiments (RT-PCR) were performed before and after TMV infection. The first strand cDNA was generated using polyA RNA derived from healthy and TMV infected N gene containing plants using oligo dT primer. The resulting first strand cDNA was used as template with N primers that anneal to Exon 3 and Exon 4 to perform RT PCR. The RT PCR results indicate that the endogenous ratio of mRNA-N to mRNA-N-tr is 25:1. However, 6 hours after TMV infection the ratio of mRNA-N to mRNA-N-tr changes to 1:23. This switching in the ratio of mRNA-N to mRNA-N-tr following TMV infection may be necessary to achieve complete resistance to TMV pathogen.

F. Discussion:

The foregoing results suggest that not only are both N and N-tr required for resistance, but also a regulatory mechanism inherent in the N gene is required for complete TMV resistance. This regulatory mechanism requires at least certain sequences in intron 3, and may also require sequences in the 5' and 3' regulatory regions of the N gene. The description herein of a simple method for determining whether particular sequence elements are required (by switching such elements into a pN/cDNA-N/intron3/3'GRS construct and assessing resistance conferred in planta by the resulting construct) will permit the elucidation of the minimal elements required for such regulation.

Having described the invention by way of illustrative examples, it will be apparent that one of skill in the art will be able to modify certain parameters (e.g., the precise sequence of cDNA-N/intron3 constructs) without departing from the spirit and teachings of the present invention. Such equivalents are encompassed within the scope of the following claims.

REFERENCES

Agrios (1997) Plant Pathology, Academic Press (London).

Altschul & Gish. (1996). *Methods Enzymol*., 266, 460–80.

Altschul et al. (1990). *J. Mol. Biol*., 215, 403–10

Altschul et al. (1994). *Nature Genet*., 6, 119–29.

Ausubel et al. (1987) In *Current Protocols in Molecular Biology*, Greene Publishing Associates and Wiley-lnterscience.

Cao et al. (1998) *Proc. Natl. Acad. Sci. USA* 95: 6531–6536.

Caputi et al. (1994) *Nucl. Acids. Res*. 22: 1018–1022.

Corpet et al. (1988). *Nucleic Acids Research* 16, 10881–90.

Gelvin et al. (1990) *Plant Molecular Biology Manual*, Kluwer Academic Publishers.

Harlow & Lane (1988) *Antibodies, A Laboratory Manual*, Cold Spring Harbor Laboratory, New York.

Higgins and Sharp (1988). *Gene*, 73: 237–244.

Higgins and Sharp (1989). *CABIOS* 5: 151–153.

Holmes (1946) *Phytopathology* 86: 643–659.

Horsch et al. (1985) *Science* 227: 1229–1231.

Huang, et al. (1992). *Computer Applications in the Biosciences* 8, 155–65.

Innis et al. (eds.) (1990) *PCR Protocols, A Guide to Methods and Applications*, Academic Press, Inc., San Diego, Calif.

Klement (1990) In Methods in Phytobacteriology (Klement et al., eds.) Akademiai Kiado (Budapest, Hungary)

Needleman and Wunsch (1970). *J. Mol. Biol*.48: 443.

Olszewski (1988) *Nucl. Acids. Res*. 16: 10765–10783.

Pearson and Lipman (1988). *Proc. Natl. Acad. Sci. USA* 85: 2444.

Pearson et al. (1994). *Methods in Molecular Biology* 24, 307–31.

Pouwels et al. (1987)

Sambrook et al. (1989) *In Molecular Cloning: A Laboratory Manual*, Cold Spring Harbor, N.Y.

Smith and Waterman (1981). *Adv. Appl. Math*. 2: 482.

Smith et al. (1985) *Science* 229:1219–1224.

Takahashi (1956) *Phytopathology* 46: 654–656.

Weissbach & Weissbach (1989) Methods for Plant Molecular Biology, Academic Press.

Whitham et al. (1994) *Cell* 78: 1101–1115.

We claim:

1. A recombinant nucleic acid molecule comprising cDNA-N/intron 3, wherein said cDNA-N/intron 3 comprises Ngene function and wherein the nucleotide sequence of said cDNA-N/intron 3 has at least 70% sequence identity to SEQ ID NO: 16, and wherein said cDNA-N/intron 3 encodes an N protein and an N-tr protein that have the activity of SEQ ID NO: 3 and SEQ ID NO: 5, respectively, in conferring tobacco mosaic virus resistance to plants.

2. A nucleic acid according to claim 1 wherein the nucleic acid further comprises pN and 3'-GRS.

3. A nucleic acid molecule according to claim 1 wherein the nucleic acid molecule comprises nucleotides 4282–9534 of the sequence shown in Seq. ID No. 9.

4. A nucleic acid molecule according to claim 2 wherein the nucleic acid molecule comprises the sequence shown in Seq. ID No. 9.

5. A transgenic plant comprising a recombinant nucleic acid molecule according to claim 1.

6. A transgenic plant according to claim 5 wherein the plant is selected from the group consisting of: tobacco, tomato and pepper.

7. A transgenic plant comprising a recombinant nucleic acid molecule according to claim 2.

8. A transgenic plant according to claim 7 wherein the plant is selected from the group consisting of: tobacco, tomato and pepper.

9. A transgenic plant comprising a recombinant nucleic acid molecule according to claim 3.

10. A transgenic plant according to claim 9 wherein the plant is selected from the group consisting of: tobacco, tomato and pepper.

11. A transgenic plant comprising a recombinant nucleic acid molecule according to claim 4.

12. A transgenic plant according to claim 11 wherein the plant is selected from the group consisting of: tobacco, tomato and pepper.

13. A recombinant nucleic acid molecule having a structure and sequence selected from the group consisting of:

E1 E2 E3 I3 E4 E5 (SEQ ID NO:16),

E1 I1 E2 E3 I3 E4 E5 (SEQ ID NO:17),

E1 E2 I2 E3 I3 E4 E5 (SEQ ID NO:18),

E1 E2 E3 I3 E4 I4 E5 (SEQ ID NO:19),

E1 I1 E2 I2 E3 I3 E4 E5 (SEQ ID NO:20),

E1 I1 E2 E3 I3 E4 I4 E5 (SEQ ID NO:21), and

E1 E2 I2 E3 I3 E4 I4 E5 (SEQ ID NO:22)

wherein E1–E5 are exons 1–5 of an N gene, and I1–I4 are introns 1–4 of an N gene.

14. A nucleic acid molecule according to claim 13, further comprising pN operably linked to E1 and 3'-GRS operably linked to E5.

15. A transgenic plant comprising a recombinant nucleic acid molecule according to claim 14.

16. A transgenic plant according to claim 15, wherein the plant is selected from the group consisting of: tobacco, tomato and pepper.

17. A recombinant nucleic acid molecule comprising a promoter sequence, an open reading frame, an intron and a 3' regulatory sequence of an N gene, wherein:

(a) the open reading frame is a cDNA-N sequence having 5' and 3' ends;

(b) the intron is a biologically active intron 3 of the N gene;

(c) the promoter sequence is a biologically active pN of the N gene;

(d) the 3' regulatory region is a biologically active 3'-GRS of the N gene; and wherein: the promoter sequence is operably linked to the 5' end of the open reading frame, the intron is positioned within the open reading frame at a position corresponding to the position of the intron in the N gene, the 3' regulatory region is operably linked to the 3' end of the open reading frame, and the recombinant nucleic acid molecule comprises N gene function, and comprises a nucleotide sequence having at least 70% sequence identity to SEQ ID NO: 9 and encodes an N protein and an N-tr protein that have the activity of SEQ ID NO: 3 and SEQ ID NO: 5, respectively, in conferring tobacco mosaic virus resistance to plants.

18. A transgenic plant comprising a recombinant nucleic acid molecule according to claim 17.

19. A transgenic plant according to claim 18, wherein the plant is selected from the group consisting of: tobacco, tomato and pepper.

20. A recombinant nucleic acid molecule comprising N gene function and comprising a nucleic acid sequence having at least 70% sequence identity to a sequence selected from the group consisting of SEQ ID NO: 16, SEQ ID NO: 17, SEQ ID NO: 18, SEQ ID NO: 19, SEQ ID NO: 20, SEQ ID NO: 21, and SEQ ID NO: 22, wherein said recombinant nucleic acid molecule encodes an N protein and an N-tr protein that have the activity of SEQ ID NO: 3 and SEQ ID NO: 5, respectively, in conferring tobacco mosaic virus resistance to plants.

21. A nucleic acid molecule according to claim 20, further comprising an operably linked pN and an operably linked 3'-GRS.

22. A transgenic plant comprising a recombinant nucleic acid molecule according to claim 21.

23. A transgenic plant according to claim 22, wherein the plant is selected from the group consisting of: tobacco, tomato and pepper.

* * * * *

UNITED STATES PATENT AND TRADEMARK OFFICE

CERTIFICATE OF CORRECTION

PATENT NO. : 6,372,962 B1
DATED : April 16, 2002
INVENTOR(S) : Dinesh-Kumar et al.

It is certified that error appears in the above-identified patent and that said Letters Patent is hereby corrected as shown below:

Title page,
Item [*], Notice:, add -- This patent is subject to a Terminal Disclaimer. --

Column 108,
Line 59, after "acid" insert -- molecule --;
Line 60, after "acid" insert -- molecule --.

Signed and Sealed this

Twenty-sixth Day of November, 2002

Attest:

JAMES E. ROGAN

Attesting Officer

*Director of the United States Patent and Trademark Office*

SEQUENCE LISTING

```
<160> NUMBER OF SEQ ID NOS:   22

<210> SEQ ID NO 1
<211> LENGTH: 12286
<212> TYPE: DNA
<213> ORGANISM: Nicotiana glutinosa

<400> SEQUENCE: 1

gatcttattc taattatatg acatttgcaa ctgtgaaggc aagaatttct tactctataa      60

ttttttaatt aaatatctaa tctaaaattt ctatagtaaa attgtgattt tgtgctcata     120

ttctcatatt tttcaatgtc tttgtttttc tttcttgttt tttatttact ttagggagga     180

gggcacacag ctcctgagta caaacgtgaa gagtgttttc atatgtttaa aagatggata     240

actcaacaac ctttgtaaac atgtaacccc atcgaagatt aatttattaa atagccatta     300

ttaagcatct gtcttctttt ctttccgatt tttatgtgtg agggtgcaaa aattaactgt     360

aaaaatagta cgggctagcc agttttcgga ctaatcattc aaaatagtca acgtttgtca     420

agtcattgaa aaatatccgc tattttgctg caacagaaac cgtccagcat atatactgga     480

gttgggtgca catgtgtatg tatttccagt acattatgct ggaactccaa cacgcggaaa     540

gttccagcat aatatactgg agattcgagc acctgtgtaa gaacttccag aatattatac     600

tggaccgata tagtttgctg gaaatccagt atattatgct ggagttctag tatatttatg     660

ctggaactcc attatattat cctggagttc cagtatactt atgctggaac tccagtataa     720
```

-continued

```
tatgctggag tttcactata cttatgctgg aactctagta taatatactg gaatattttc    780
cggatcttga acaatgtgtt cgttcaaatt tatctttaca tgaaaagtga ctaaatttta    840
attacttttg aaagtgtgac tatttttgaa tgagcacttg taaatctggt tatttttgaa    900
tttctcccga attaacttag tctaacaata tcttgttctg actggaaaat tcagtctaat    960
taattactgc attaactatc tcttcttctc tttgtgaatt tttttttttt ttttataaca   1020
aatatgagat aatataaaaa cctctagttc ttctttgaaa aacaggtgag attccaatta   1080
aaacaaaatg ccattcttga acgattttga cagggctttt gcatctatat ccactttttg   1140
ggtcatattt taatttatac ccgctttgca aaaaaattac aagcgtatcc acttttcgca   1200
taaacttcag gcttacgggt ctggagtagc aaaggcaatc acacaaaggt tcagcattct   1260
aggctttttc gaaaacttca gcagaatgct gaagttattt agttcatttg taaaaacttc   1320
agcactaaat aagctgaagt tttgtcctgg attaaataat tttgtcataa agctttttca   1380
ataacttcag cagaagatgc tgaagttatt tagttcattt ataaaaactc cagcactaaa   1440
taagctgaag ttttttcttg aattaattag ttttgtcata aagcttttc aaaaaacttc   1500
agtgctgaag ttatttagtt cgtttttaaa atcttcagca gaagatggtg aagttattaa   1560
gttcatttgt aaaaacttca gcatcagata agctgaagtt ttgtcctgga ttcattagtt   1620
ttgcagtaaa gctttttcaa aaacttcagc agaagatgct gaagttattt agttcatttg   1680
taaaaacttt agcactaaat atgctgaagt tttgcacagg tattagaaag gtggcgcctg   1740
aaattgtaaa aattaagata tatattaaat aatttaaaaa taaaggtata aattaaatga   1800
gagcgatcaa ataaggcgcc tgcgcaattt ttgatgtcaa ttaggtagca tcaagttaat   1860
tttgcacaat ttttgcgttt ctctatttag attgtttgaa aaaatgacaa ctttaataaa   1920
ttgccgaaat aataaaaaaa taaacaagtt gacagttacc tctttctcct cccgtacaac   1980
cttttcacca ccacccctcc atgtccatga tttgttggtc cctaaagttt aaataataat   2040
aaataaataa ataaaaattg taattaaaat ttagagatca actttggtcg ttaaatatat   2100
attattaaaa tattataccg accgaagttg gtcggtattt tatttatcct aaatatttgg   2160
ttcttttaac ttagtgacca acgttggtcg ctaaattaaa aggaccacca atatagcgac   2220
caatccattt tggacgcgtt ttggtcggta tattgtgata agcgaccaac tttggtcgct   2280
atttgtggtc tctttttgcc ggatttctag cagtgtgtac acgcaaatcg aaaaggataa   2340
aatgagattt ttaaggctaa cgagtgcaga attaaatttt aaaacgtaag tttaggtcat   2400
cacatattat gtgattttta aaaaaatgat cttcatatag aatacacacg taacacgctt   2460
gcccaaaaac tattagaaca aaataagtaa cggctatttt taaaccttca atccgtagca   2520
gcccactaat ccctggctcc aattttcttc aataataagt tgtatgcaga aggaaaaaga   2580
ttgttcctag aagttgtatg cgatactaaa caccttcccc ctgttatttt tctgtctgtt   2640
ttctttaaag caacgaatcc tgtgccttga ttcttttctt gtttcctgtg ttagttataa   2700
gtttcaataa tgaaaaataa tatattatat tgggcgtagg atcacaaggg attcaagaag   2760
caacactagt cgggaataga taaaggaaca taatcaataa tcagcatgga aaaggaagaa   2820
gtagcgaaaa ttcggcaaga ataatcaatt taattaatta cagtagctaa ttcttatata   2880
ttaagtttct gagaaaagta acatttcttc acatttatgg acctacattt gttgtcactt   2940
tctatctgcg caaagaaaaa taagaccata gtactgcttt tggttagtac aactgttgac   3000
aaagaaaatt actgggatat tacccttcgt tttctttgta gctttattta tcggcttgta   3060
```

-continued

```
cttttagttg ttccttgtga acatattact gttgaatttg gtgcagggag ggtgggtggt   3120
ctttgaagga attacctact tcccttctat tacagtgcaa agaaaaccct ataacaataa   3180
taattctaat caactggagt aaacattaag atgaagcttc acaaaaaaat cctacaattt   3240
actttctatt aggagtagtc ggtggcggat ttaggatttt gcgaatatga gtgcactatt   3300
acgaagaggc gaatctagga tataaatttt acaggtttaa cgtttggttc ttactattgc   3360
acccattaca attttgaaat tataagttca aaattattat tttttaattg taattttctt   3420
atatctattt ccatactccg tacttaaaat attgggatca gtttaaccca atagcataca   3480
ctgcattatg cactagttta atatgcaaat tttatttaat catataagat ttttcggtga   3540
caaataacaa ataggaattt taatatgtga aaattttaaa agaataaatc aaaaagaaag   3600
aaagaaagaa aaagaaatgt atttaattaa tacgcaccaa gtgatgccta gttttagaaa   3660
agaaaaaata acaataagat tgtcatagga aaaaggattg aaaggtcgac cagataattt   3720
tttttttttt tttttaccca gaatgatatg ttccacaata tattgtacaa ttttgtcgaa   3780
actttataat aactttctta acgttaataa attgggaaca agtttacgat taaatttcac   3840
atgtgatcat tcaactttgt gtttattatc caacaaaaat gaaaaatatt ttgctagatg   3900
aagactttgt catcctcggt agaaaactaa aatagaaaaa gaattcaatc aatggagacc   3960
tttttctctt tggagcaata attcaattca attgggaagg aatttcctac tcccttctat   4020
taaagttcaa agaaaaccca ataattcctt ttattgcatt aagaagaatt ttcctactag   4080
tgtatatcag ttgactagga caccaataat tctatggagt agagcccatc tcacacaaac   4140
tttttccaat agcaatataa ctcttatctc ttctaatata tataaaaatt tgttgaaaat   4200
atcatctatt attttcttac cacaatcaca attttttcac atacagtttc ttattctttt   4260
cagagaatta acgttgagtc catggcatct tcttcttctt cttctagatg gagctatgat   4320
gttttcttaa gttttagagg cgaagatact cgaaaaacgt ttacaagtca cttatacgaa   4380
gtcttgaatg ataagggaat aaaaaccttt caagatgata aaaggctaga gtacggcgca   4440
accatcccag gtgaactctg taaagctata gaagagtctc aatttgccat tgttgttttc   4500
tcagagaatt atgcaacatc aaggtggtgt ttgaatgaac tagtgaagat catggaatgc   4560
aaaactcgat ttaagcaaac tgttataccg atattctatg atgtggatcc atcacatgtt   4620
cggaaccaaa aggagagctt tgcaaaagcc tttgaagaac atgaaacaaa gtataaggat   4680
gatgttgagg gaatacaaag atggaggatt gctttaaatg aagcggccaa tctcaaaggc   4740
tcctgtgata atcgtgacaa gtgagttaaa aacatataag ctgaatactt tgcattcaaa   4800
tgagttaaac ataatcttaa ataaattttt caatttttttg gaataaattg atagttgatt   4860
atatatgttt ctatcagtta attacaaact caataacatt attacgtaga taaaattttt   4920
attagttctt caaagagttt gatttatgtg cacactcttt gtatatatca caatcttttt   4980
acttttgtag gactgatgca gactgtattc gacagattgt tgaccaaatc tcatccaaat   5040
tatgcaagat ttctttatct tatttgcaaa acattgttgg aatagatact catttagaga   5100
aaatagaatc cttactagag ataggaatca atggtgttcg gattatgggg atctggggaa   5160
tgggggggagt cggtaaaaca acaatagcaa gagctatatt tgatactctt ttaggaagaa   5220
tggatagttc ctatcaattt gatggtgctt gtttccttaa ggatattaaa gaaaacaaac   5280
gtggaatgca ttctttgcaa aatgcccttc tctctgaact tttaaggaa aaagctaatt   5340
acaataatga ggaggatgga aagcaccaaa tggctagtag acttcgttcg aagaaggtcc   5400
taattgtgct tgatgatata gataataaag atcattattt ggagtattta gcaggtgatc   5460
```

-continued

```
ttgattggtt tggtaatggt agtagaatta ttataacaac tagagacaag catttgatag   5520
agaagaatga tataatatat gaggtgactg cactacccga tcatgaatcc attcaattgt   5580
tcaaacaaca tgctttcgga aaagaagttc caaatgagaa ttttgagaag ctttcattag   5640
aggtagtaaa ttatgctaaa ggccttcctt tagccctcaa agtgtggggt tctttgctgc   5700
ataacctacg attaactgaa tggaaaagtg ctatagagca catgaaaaat aactcttatt   5760
ctggaattat tgataagctc aaaataagtt atgatggatt agagcccaaa caacaagaga   5820
tgtttttaga tatagcatgc ttcttgcgag gggaagaaaa agattacatc ctacaaatcc   5880
ttgagagttg tcatattgga gctgaatacg ggttacgtat tttaattgac aaatctcttg   5940
tgttcatctc tgaatataat caggttcaaa tgcatgactt aatacaggat atgggtaaat   6000
atatagtgaa ttttcaaaaa gatcccggag aacgtagcag attatggctc gccaaggaag   6060
tcgaagaagt gatgagcaac aacacagtaa gtaagctaaa taatgcaata atatttaatt   6120
tctaatttta tattctaaag acacataggg cagtcaattc cagttatttg ttcctcttgc   6180
ttcatagtct tgacggtaca tcattttagt tgtttacttt agttagtagg agatataaaa   6240
gtaatattaa ttacctcatt agtaaaaaaa aacattaatt gcctaatttg tttagtagcc   6300
gctttaattt acgttcccta attcgttttt tcttatattt tttagggatg gattagtcta   6360
gtagccactt aatctgtttg atccaatgtc tttctttgga ttaacttgaa aattttatga   6420
cattatatat aataactcaa tcattcattc actttaccat tattattttt tatataaagt   6480
tacaatttat tggtactgtt tcagttacaa ttactttcca acatggaaaa cttataaact   6540
ggactccaat aaacttataa gaaaaatgta ataatagaaa ataaaattat ataattaatt   6600
acaaaaaagt atttttctga agtaacatca gtatttctta aaaagaatcc aattaacatt   6660
gtatcttaaa ctttggtatt gtaaggcgtg agaaagtagt ggccttattt caatttgacg   6720
tgaagaatag aatgcctttt aacgacataa gggaaggggg caagaataag tttctattca   6780
gccgggctcg aagcagaagg tagaacgtaa tatcttttgt tggttcagct catcaagcta   6840
ttacaaaaga gtccgctcat attaacaaac ggagtttata cgacatttga aattatactt   6900
tgtagactaa tgatcttctt gttaccaggg gaccatggca atggaagcaa tttgggtttc   6960
ttcttattct agtactctac gctttagcaa tcaggccgtg aaaaatatga aaaggcttag   7020
ggtatttaac atggggaggt cgtcgacaca ttatgccatc gattatctgc ccaacaactt   7080
gcgttgtttt gtttgcacta actatccttg ggagtcattt ccatctacat ttgaactcaa   7140
aatgcttgtt cacctccaac tccgacacaa ttctctgcgt catttatgga cagaaacaaa   7200
ggtacaatag cttgaattct attttgttgt catttatttt tctctctaac tatctttgtc   7260
ctttaatttg gtgataatga acaaatatta ttgttttttg ttatgaaaca ataaaagaag   7320
aagaacaata ttgcagagaa agagggagat ggaattctta ttgaattttg gggcgattta   7380
caatggggta agacccctct atttacaggg gaaaaataac ttagcctcaa aataaagctc   7440
tttaaaagat agacattcac tctaaataga attctattat aacacttttg gcgtacttcc   7500
ttttttggct agaattatga tacatgtctt taaatgaaca gaagttgctt ttgtaattta   7560
tcaggactta tgttgaaact tatgaaaatt gttattgttt atgttgtcta atactaaata   7620
taaaatacaa taatatttta tcgtaatttt ttaaaaattt gtcaaataat gcaaatgaaa   7680
aattaaattt tttggtcctt taaaaatttg agaatgaaaa agtacgagtt atacttccta   7740
aaagtttgat agtgaataat atgtaaaatt taaagaatga ctaatattgg actaatactt   7800
```

-continued

```
taaaacaaat aacttaatat acaaattata gcgagacatt ttcattcgtt gtactgaatg   7860
caagaaagaa aggaaaaaaa aactcattta taatatagtt tgtcttctac tattttacct   7920
tattgcttca aatttgtatt ttatcgattt tgctatatct tatgattttt ttcacggtca   7980
atattcttct tacaagaata aattttatat acctcaagtg ttttgtcaat ttgataaata   8040
atttttctta tatgatgaac ttgtaaaata atagaattgg attcttttgc taattagtta   8100
attcaacgac ttaattattt attctcaaca ttaaaggaaa taatttagtt tttattaatt   8160
caaactctta gtatttgctc attctaattt tcagtccaat aagaattcaa ttttcaaata   8220
gtaagaaaag tcatatattt tgaattttat gttttccgaa gcattgtttg tttgtttaac   8280
tctacgggag ttttctaact cacattttgt ataataaaat tttttgagta gtagttcagt   8340
acaactctaa tattaatggg ctttaaataa ggaaatatat attacgtaaa aatttaaatc   8400
attttaaagt tctttcctac caagtaaata agggaaaatt taataacaaa aatttagttg   8460
attttaaaat cctaaatatt agaaaattaa cttaaaatat aatttcgtct agtgtaaaat   8520
ttatttttaa agggtaaaaa agacgaacga cattaagagc ctttgtaatt ttaatatagt   8580
ataaatataa ataatttacc tttattcagt ttcttaacaa gtaattttcc atatataaaa   8640
aataaatttc tatattcaca caaaaataat gtgttggccc tcgtaattca aatactatca   8700
ttcatttctt gtcgagggag tagtaaatac ttttaggaaa gttagcaata agtaatcaag   8760
aaatcaagaa aacagaggtc atttgatgcc cacaaataca aatgaaaaaa caaaacaaat   8820
gttacgaaac aataaaagaa caagaatagc ctcaaagtaa aactctctga tagacattta   8880
ctctaaatag aattctattt ataacaatca aaaagtttct acatttatag atagctccac   8940
tagccaaata ttttattatt ggaatcagca aaataggttg tttctttttt tattctcatt   9000
ctgtctgtgt tctaaacagc atttgccgtc tctacggagg atagatctca gctggtctaa   9060
aagattgacg cgaacaccag atttcacggg gatgccaaat ttggagtatg tgaatttgta   9120
tcaatgtagt aatcttgaag aagttcacca ttccctggga tgttgcagca aagtcattgg   9180
tttatatttg aatgattgta aaagccttaa gaggtttcca tgtgttaacg tggaatctct   9240
tgaatatctg ggtctaagaa gttgcgatag tttagagaaa ttgccagaaa tctacgggag   9300
aatgaagccg gagatacaga ttcacatgca aggctctggg ataagggaac taccatcatc   9360
tatttttcag tacaaaactc atgttaccaa gctattgttg tggaatatga aaaaccttgt   9420
agctcttcca agcagcatat gtaggttgaa aagtttggtt agtctgagtg tgtcgggttg   9480
ctcaaaactt gaaagcttgc cagaagagat aggggattta gacaacttac gggtgtttga   9540
tgccagtgat actctaattt tacgacctcc gtcttccatc atacgcttga acaaacttat   9600
aatcttgatg tttcgaggct tcaaagatgg agtgcacttt gagttccctc ctgtggctga   9660
aggattacac tcattggaat atctgaatct cagttactgc aatctaatag atggaggact   9720
tccggaagag attggatcct tatcctcttt gaaaaagttg gatctcagta gaaataattt   9780
tgagcatttg ccttcaagta tagcccaact tggtgctctt caatccttag acttaaaaga   9840
ttgccagagg cttacacagc taccagaact tcccccagaa ttaaatgaat tgcatgtaga   9900
ttgtcatatg gctctgaaat ttatccatta tttagtaaca aagagaaaga aactacatag   9960
agtgaaactt gatgatgcac acaatgatac tatgtacaat ttgtttgcat ataccatgtt  10020
tcagaatatc tcttccatga ggcatgacat ctctgcttca gattccttgt cactaacagt  10080
atttaccggt caaccgtatc ctgaaaagat cccgagttgg ttccaccatc agggttggga  10140
tagtagtgta tcagtcaatt tgcctgaaaa ttggtatata cctgataaat tcttgggatt  10200
```

```
tgctgtatgt tactctcgta gcttaattga cacaacagct cacttgattc ccgtatgtga  10260
tgacaagatg tcgcgcatga cccagaaact tgccttatca gaatgtgata cagaatcatc  10320
caactattca gaatgggata tacatttttt ctttgtacct tttgctggct tatgggatac  10380
atctaaggca aatggaaaaa caccaaatga ttatgggatt attaggctat ctttttctgg  10440
agaagagaag atgtatggac ttcgtttgtt gtataaagaa ggaccagagg ttaatgcctt  10500
gttacaaatg agggaaaata gcaatgaacc aacagaacat tccactggga taaggaggac  10560
tcaatataac aacagaactt ccttttatgt aagtctctac ttctattagc tacaaagtct  10620
tcttccaaaa tcaatactcc atccgttcca gtttatgtga acctattttt tgttcgtcca  10680
ttctaaaaag aatgacccct ttctaaattt ggaaataatt ttggttaaac ttataattct  10740
accattaacg agaagctttt ataaccacac aaatattctg ggcccttttt tgaattgttt  10800
aggaccataa attccaaaag tcctcatttt ttcttaaact ccgtgcccaa tcaaacaagt  10860
tcacgtaaat tggaacggag ggaatatatt ttttcttctc attcttttcc cctatttaca  10920
ggagctcatc aatgggtgat gtacatatca acaacgagtt ttaaaggatt ccaacaagta  10980
taacttttta tgctcaaatc agctccttgt attgtggaga aagctgagta cgagatgaag  11040
ttgacgtccg ttatccttta tgatctctct gttctttgtg ttaacttgcc tacttcatca  11100
gatgaataac agaagcccgt tcctctcatt ctcaacactg tttgcacgtc tgttgttact  11160
tgttaaaatg gatcttgata aagtaataac atctctatat tacttataag tggttttaac  11220
aagttcactc ttttgctttt gcagttcaaa tgggaacaca atgtatattg agaactagaa  11280
caatgacact gcatatatat atatatatgt atgtatgtaa ttctcgtctt ttggactaga  11340
ataccttgtt tcattatgaa atgaattaac atcttcgcct ttgctgacaa gtaaccaatt  11400
acagatgaat gaaatcacct gatcaacatt cattagcttt gtattctttg acgatttcgg  11460
tttcataact ctttcccctg cagttaaaat atgtagttag cccgattgca cctctagggc  11520
gcagcggagt attaaaaaaa aaaagatctt tctcatttgt ctaagtcttg gtagtcagaa  11580
ttacgagttt gtataaagtt ggctcaaaca tcacctttgt ataagaaaaa tacatacaca  11640
cacagtagaa aagaaacaga taccttcgca aatttgattg ggaggtactg atttcttctt  11700
tcagttggcg attagcctct tgtgtcatct ttggagcttc ttatgatttt tttttcttag  11760
gtaaaattca tttaataatt tgttaatcat attactgttg ggctaaacta ccccgataca  11820
ctcataacat ggtgtgatat tgttcgcttt gggccaagcc cgtatggttt tccccaaaag  11880
gcttcgcacc attaagagat ccatacacct taaatgtaga ctcacaatct tttcagctat  11940
taatgtggca ctttattcgc atacccaaca ttatgtgtac actacaggaa ttagagttgg  12000
aacagagttt taaaactagt caaagagttt tggagctaac aaaactatct tgataaatat  12060
aatacaaaca attcgtagtg ttcagaggcg gaataactat gtgattactg tagaaactta  12120
taaactttaa attttggatt cgcatttgct taccgttgat tttctatctc atttatcttg  12180
gctggttgtg ccataattaa atccattgga gggacattgt aggattagct tacgtaaatg  12240
tgcttgtaaa ttgaataacg tgagctaaca ttgttgacaa attcta                12286
```

<210> SEQ ID NO 2
<211> LENGTH: 3760
<212> TYPE: DNA
<213> ORGANISM: Nicotiana glutinosa
<220> FEATURE:
<221> NAME/KEY: CDS
<222> LOCATION: (60)..(3494)

-continued

<400> SEQUENCE: 2

```
ggcacgagat tttttcacat acagtttctt attcttttca gagaattaac gttgagtcc      59

atg gca tct tct tct tct tct tct aga tgg agc tat gat gtt ttc tta      107
Met Ala Ser Ser Ser Ser Ser Ser Arg Trp Ser Tyr Asp Val Phe Leu
1               5                   10                  15

agt ttt aga ggc gaa gat act cga aaa acg ttt aca agt cac tta tac      155
Ser Phe Arg Gly Glu Asp Thr Arg Lys Thr Phe Thr Ser His Leu Tyr
            20                  25                  30

gaa gtc ttg aat gat aag gga ata aaa acc ttt caa gat gat aaa agg      203
Glu Val Leu Asn Asp Lys Gly Ile Lys Thr Phe Gln Asp Asp Lys Arg
        35                  40                  45

cta gag tac ggc gca acc atc cca ggt gaa ctc tgt aaa gct ata gaa      251
Leu Glu Tyr Gly Ala Thr Ile Pro Gly Glu Leu Cys Lys Ala Ile Glu
    50                  55                  60

gag tct caa ttt gcc att gtt gtt ttc tca gag aat tat gca aca tca      299
Glu Ser Gln Phe Ala Ile Val Val Phe Ser Glu Asn Tyr Ala Thr Ser
65                  70                  75                  80

agg tgg tgt ttg aat gaa cta gtg aag atc atg gaa tgc aaa act cga      347
Arg Trp Cys Leu Asn Glu Leu Val Lys Ile Met Glu Cys Lys Thr Arg
                85                  90                  95

ttt aag caa act gtt ata ccg ata ttc tat gat gtg gat cca tca cat      395
Phe Lys Gln Thr Val Ile Pro Ile Phe Tyr Asp Val Asp Pro Ser His
            100                 105                 110

gtt cgg aac caa aag gag agc ttt gca aaa gcc ttt gaa gaa cat gaa      443
Val Arg Asn Gln Lys Glu Ser Phe Ala Lys Ala Phe Glu Glu His Glu
        115                 120                 125

aca aag tat aag gat gat gtt gag gga ata caa aga tgg agg att gct      491
Thr Lys Tyr Lys Asp Asp Val Glu Gly Ile Gln Arg Trp Arg Ile Ala
    130                 135                 140

tta aat gaa gcg gcc aat ctc aaa ggc tcc tgt gat aat cgt gac aag      539
Leu Asn Glu Ala Ala Asn Leu Lys Gly Ser Cys Asp Asn Arg Asp Lys
145                 150                 155                 160

act gat gca gac tgt att cga cag att gtt gac caa atc tca tcc aaa      587
Thr Asp Ala Asp Cys Ile Arg Gln Ile Val Asp Gln Ile Ser Ser Lys
                165                 170                 175

tta tgc aag att tct tta tct tat ttg caa aac att gtt gga ata gat      635
Leu Cys Lys Ile Ser Leu Ser Tyr Leu Gln Asn Ile Val Gly Ile Asp
            180                 185                 190

act cat tta gag aaa ata gaa tcc tta cta gag ata gga atc aat ggt      683
Thr His Leu Glu Lys Ile Glu Ser Leu Leu Glu Ile Gly Ile Asn Gly
        195                 200                 205

gtt cgg att atg ggg atc tgg gga atg ggg gga gtc ggt aaa aca aca      731
Val Arg Ile Met Gly Ile Trp Gly Met Gly Gly Val Gly Lys Thr Thr
    210                 215                 220

ata gca aga gct ata ttt gat act ctt tta gga aga atg gat agt tcc      779
Ile Ala Arg Ala Ile Phe Asp Thr Leu Leu Gly Arg Met Asp Ser Ser
225                 230                 235                 240

tat caa ttt gat ggt gct tgt ttc ctt aag gat att aaa gaa aac aaa      827
Tyr Gln Phe Asp Gly Ala Cys Phe Leu Lys Asp Ile Lys Glu Asn Lys
                245                 250                 255

cgt gga atg cat tct ttg caa aat gcc ctt ctc tct gaa ctt tta agg      875
Arg Gly Met His Ser Leu Gln Asn Ala Leu Leu Ser Glu Leu Leu Arg
            260                 265                 270

gaa aaa gct aat tac aat aat gag gag gat gga aag cac caa atg gct      923
Glu Lys Ala Asn Tyr Asn Asn Glu Glu Asp Gly Lys His Gln Met Ala
        275                 280                 285

agt aga ctt cgt tcg aag aag gtc cta att gtg ctt gat gat ata gat      971
Ser Arg Leu Arg Ser Lys Lys Val Leu Ile Val Leu Asp Asp Ile Asp
```

-continued

```
    290                 295                 300

aat aaa gat cat tat ttg gag tat tta gca ggt gat ctt gat tgg ttt     1019
Asn Lys Asp His Tyr Leu Glu Tyr Leu Ala Gly Asp Leu Asp Trp Phe
305                 310                 315                 320

ggt aat ggt agt aga att att ata aca act aga gac aag cat ttg ata     1067
Gly Asn Gly Ser Arg Ile Ile Ile Thr Thr Arg Asp Lys His Leu Ile
                325                 330                 335

gag aag aat gat ata ata tat gag gtg act gca cta ccc gat cat gaa     1115
Glu Lys Asn Asp Ile Ile Tyr Glu Val Thr Ala Leu Pro Asp His Glu
            340                 345                 350

tcc att caa ttg ttc aaa caa cat gct ttc gga aaa gaa gtt cca aat     1163
Ser Ile Gln Leu Phe Lys Gln His Ala Phe Gly Lys Glu Val Pro Asn
        355                 360                 365

gag aat ttt gag aag ctt tca tta gag gta gta aat tat gct aaa ggc     1211
Glu Asn Phe Glu Lys Leu Ser Leu Glu Val Val Asn Tyr Ala Lys Gly
    370                 375                 380

ctt cct tta gcc ctc aaa gtg tgg ggt tct ttg ctg cat aac cta cga     1259
Leu Pro Leu Ala Leu Lys Val Trp Gly Ser Leu Leu His Asn Leu Arg
385                 390                 395                 400

tta act gaa tgg aaa agt gct ata gag cac atg aaa aat aac tct tat     1307
Leu Thr Glu Trp Lys Ser Ala Ile Glu His Met Lys Asn Asn Ser Tyr
                405                 410                 415

tct gga att att gat aag ctc aaa ata agt tat gat gga tta gag ccc     1355
Ser Gly Ile Ile Asp Lys Leu Lys Ile Ser Tyr Asp Gly Leu Glu Pro
            420                 425                 430

aaa caa caa gag atg ttt tta gat ata gca tgc ttc ttg cga ggg gaa     1403
Lys Gln Gln Glu Met Phe Leu Asp Ile Ala Cys Phe Leu Arg Gly Glu
        435                 440                 445

gaa aaa gat tac atc cta caa atc ctt gag agt tgt cat att gga gct     1451
Glu Lys Asp Tyr Ile Leu Gln Ile Leu Glu Ser Cys His Ile Gly Ala
    450                 455                 460

gaa tac ggg tta cgt att tta att gac aaa tct ctt gtg ttc atc tct     1499
Glu Tyr Gly Leu Arg Ile Leu Ile Asp Lys Ser Leu Val Phe Ile Ser
465                 470                 475                 480

gaa tat aat cag gtt caa atg cat gac tta ata cag gat atg ggt aaa     1547
Glu Tyr Asn Gln Val Gln Met His Asp Leu Ile Gln Asp Met Gly Lys
                485                 490                 495

tat ata gtg aat ttt caa aaa gat ccc gga gaa cgt agc aga tta tgg     1595
Tyr Ile Val Asn Phe Gln Lys Asp Pro Gly Glu Arg Ser Arg Leu Trp
            500                 505                 510

ctc gcc aag gaa gtc gaa gaa gtg atg agc aac aac aca ggg acc atg     1643
Leu Ala Lys Glu Val Glu Glu Val Met Ser Asn Asn Thr Gly Thr Met
        515                 520                 525

gca atg gaa gca att tgg gtt tct tct tat tct agt act cta cgc ttt     1691
Ala Met Glu Ala Ile Trp Val Ser Ser Tyr Ser Ser Thr Leu Arg Phe
    530                 535                 540

agc aat cag gcc gtg aaa aat atg aaa agg ctt agg gta ttt aac atg     1739
Ser Asn Gln Ala Val Lys Asn Met Lys Arg Leu Arg Val Phe Asn Met
545                 550                 555                 560

ggg agg tcg tcg aca cat tat gcc atc gat tat ctg ccc aac aac ttg     1787
Gly Arg Ser Ser Thr His Tyr Ala Ile Asp Tyr Leu Pro Asn Asn Leu
                565                 570                 575

cgt tgt ttt gtt tgc act aac tat cct tgg gag tca ttt cca tct aca     1835
Arg Cys Phe Val Cys Thr Asn Tyr Pro Trp Glu Ser Phe Pro Ser Thr
            580                 585                 590

ttt gaa ctc aaa atg ctt gtt cac ctc caa ctc cga cac aat tct ctg     1883
Phe Glu Leu Lys Met Leu Val His Leu Gln Leu Arg His Asn Ser Leu
        595                 600                 605

cgt cat tta tgg aca gaa aca aag cat ttg ccg tct cta cgg agg ata     1931
```

-continued

```
Arg His Leu Trp Thr Glu Thr Lys His Leu Pro Ser Leu Arg Arg Ile
    610                 615                 620

gat ctc agc tgg tct aaa aga ttg acg cga aca cca gat ttc acg ggg      1979
Asp Leu Ser Trp Ser Lys Arg Leu Thr Arg Thr Pro Asp Phe Thr Gly
625                 630                 635                 640

atg cca aat ttg gag tat gtg aat ttg tat caa tgt agt aat ctt gaa      2027
Met Pro Asn Leu Glu Tyr Val Asn Leu Tyr Gln Cys Ser Asn Leu Glu
                645                 650                 655

gaa gtt cac cat tcc ctg gga tgt tgc agc aaa gtc att ggt tta tat      2075
Glu Val His His Ser Leu Gly Cys Cys Ser Lys Val Ile Gly Leu Tyr
            660                 665                 670

ttg aat gat tgt aaa agc ctt aag agg ttt cca tgt gtt aac gtg gaa      2123
Leu Asn Asp Cys Lys Ser Leu Lys Arg Phe Pro Cys Val Asn Val Glu
        675                 680                 685

tct ctt gaa tat ctg ggt cta aga agt tgc gat agt tta gag aaa ttg      2171
Ser Leu Glu Tyr Leu Gly Leu Arg Ser Cys Asp Ser Leu Glu Lys Leu
    690                 695                 700

cca gaa atc tac ggg aga atg aag ccg gag ata cag att cac atg caa      2219
Pro Glu Ile Tyr Gly Arg Met Lys Pro Glu Ile Gln Ile His Met Gln
705                 710                 715                 720

ggc tct ggg ata agg gaa cta cca tca tct att ttt cag tac aaa act      2267
Gly Ser Gly Ile Arg Glu Leu Pro Ser Ser Ile Phe Gln Tyr Lys Thr
                725                 730                 735

cat gtt acc aag cta ttg ttg tgg aat atg aaa aac ctt gta gct ctt      2315
His Val Thr Lys Leu Leu Leu Trp Asn Met Lys Asn Leu Val Ala Leu
            740                 745                 750

cca agc agc ata tgt agg ttg aaa agt ttg gtt agt ctg agt gtg tcg      2363
Pro Ser Ser Ile Cys Arg Leu Lys Ser Leu Val Ser Leu Ser Val Ser
        755                 760                 765

ggt tgc tca aaa ctt gaa agc ttg cca gaa gag ata ggg gat tta gac      2411
Gly Cys Ser Lys Leu Glu Ser Leu Pro Glu Glu Ile Gly Asp Leu Asp
    770                 775                 780

aac tta cgg gtg ttt gat gcc agt gat act cta att tta cga cct ccg      2459
Asn Leu Arg Val Phe Asp Ala Ser Asp Thr Leu Ile Leu Arg Pro Pro
785                 790                 795                 800

tct tcc atc ata cgc ttg aac aaa ctt ata atc ttg atg ttt cga ggc      2507
Ser Ser Ile Ile Arg Leu Asn Lys Leu Ile Ile Leu Met Phe Arg Gly
                805                 810                 815

ttc aaa gat gga gtg cac ttt gag ttc cct cct gtg gct gaa gga tta      2555
Phe Lys Asp Gly Val His Phe Glu Phe Pro Pro Val Ala Glu Gly Leu
            820                 825                 830

cac tca ttg gaa tat ctg aat ctc agt tac tgc aat cta ata gat gga      2603
His Ser Leu Glu Tyr Leu Asn Leu Ser Tyr Cys Asn Leu Ile Asp Gly
        835                 840                 845

gga ctt ccg gaa gag att gga tcc tta tcc tct ttg aaa aag ttg gat      2651
Gly Leu Pro Glu Glu Ile Gly Ser Leu Ser Ser Leu Lys Lys Leu Asp
    850                 855                 860

ctc agt aga aat aat ttt gag cat ttg cct tca agt ata gcc caa ctt      2699
Leu Ser Arg Asn Asn Phe Glu His Leu Pro Ser Ser Ile Ala Gln Leu
865                 870                 875                 880

ggt gct ctt caa tcc tta gac tta aaa gat tgc cag agg ctt aca cag      2747
Gly Ala Leu Gln Ser Leu Asp Leu Lys Asp Cys Gln Arg Leu Thr Gln
                885                 890                 895

cta cca gaa ctt ccc cca gaa tta aat gaa ttg cat gta gat tgt cat      2795
Leu Pro Glu Leu Pro Pro Glu Leu Asn Glu Leu His Val Asp Cys His
            900                 905                 910

atg gct ctg aaa ttt atc cat tat tta gta aca aag aga aag aaa cta      2843
Met Ala Leu Lys Phe Ile His Tyr Leu Val Thr Lys Arg Lys Lys Leu
        915                 920                 925
```

-continued

```
cat aga gtg aaa ctt gat gat gca cac aat gat act atg tac aat ttg     2891
His Arg Val Lys Leu Asp Asp Ala His Asn Asp Thr Met Tyr Asn Leu
    930                 935                 940

ttt gca tat acc atg ttt cag aat atc tct tcc atg agg cat gac atc     2939
Phe Ala Tyr Thr Met Phe Gln Asn Ile Ser Ser Met Arg His Asp Ile
945                 950                 955                 960

tct gct tca gat tcc ttg tca cta aca gta ttt acc ggt caa ccg tat     2987
Ser Ala Ser Asp Ser Leu Ser Leu Thr Val Phe Thr Gly Gln Pro Tyr
                965                 970                 975

cct gaa aag atc ccg agt tgg ttc cac cat cag ggt tgg gat agt agt     3035
Pro Glu Lys Ile Pro Ser Trp Phe His His Gln Gly Trp Asp Ser Ser
            980                 985                 990

gta tca gtc aat ttg cct gaa aat  tgg tat ata cct gat  aaa ttc ttg   3083
Val Ser Val Asn Leu Pro Glu Asn  Trp Tyr Ile Pro Asp  Lys Phe Leu
        995                 1000                1005

gga ttt  gct gta tgt tac tct  cgt agc tta att gac  aca aca gct      3128
Gly Phe  Ala Val Cys Tyr Ser  Arg Ser Leu Ile Asp  Thr Thr Ala
    1010                1015                1020

cac ttg  att ccc gta tgt gat  gac aag atg tcg cgc  atg acc cag      3173
His Leu  Ile Pro Val Cys Asp  Asp Lys Met Ser Arg  Met Thr Gln
    1025                1030                1035

aaa ctt  gcc tta tca gaa tgt  gat aca gaa tca tcc  aac tat tca      3218
Lys Leu  Ala Leu Ser Glu Cys  Asp Thr Glu Ser Ser  Asn Tyr Ser
    1040                1045                1050

gaa tgg  gat ata cat ttt ttc  ttt gta cct ttt gct  ggc tta tgg      3263
Glu Trp  Asp Ile His Phe Phe  Phe Val Pro Phe Ala  Gly Leu Trp
    1055                1060                1065

gat aca  tct aag gca aat gga  aaa aca cca aat gat  tat ggg att      3308
Asp Thr  Ser Lys Ala Asn Gly  Lys Thr Pro Asn Asp  Tyr Gly Ile
    1070                1075                1080

att agg  cta tct ttt tct gga  gaa gag aag atg tat  gga ctt cgt      3353
Ile Arg  Leu Ser Phe Ser Gly  Glu Glu Lys Met Tyr  Gly Leu Arg
    1085                1090                1095

ttg ttg  tat aaa gaa gga cca  gag gtt aat gcc ttg  tta caa atg      3398
Leu Leu  Tyr Lys Glu Gly Pro  Glu Val Asn Ala Leu  Leu Gln Met
    1100                1105                1110

agg gaa  aat agc aat gaa cca  aca gaa cat tcc act  ggg ata agg      3443
Arg Glu  Asn Ser Asn Glu Pro  Thr Glu His Ser Thr  Gly Ile Arg
    1115                1120                1125

agg act  caa tat aac aac aga  act tcc ttt tat gag  ctc atc aat      3488
Arg Thr  Gln Tyr Asn Asn Arg  Thr Ser Phe Tyr Glu  Leu Ile Asn
    1130                1135                1140

ggg tga tgtacatatc aacaacgagt tttaaaggat tccaacaagt ataacttttt      3544
Gly

atgctcaaat cagctccttg tattgtggag aaagctgagt acgagatgaa gttgacgtcc   3604

gttatccttt atgatctctc tgttctttgt gttaacttgc ctacttcatc agatgaataa   3664

cagaagcccg ttcctctcat tctcaacact gtttgcacgt ctgttgttac ttgttaaaat   3724

ggatcttgat aaagtaataa catctctata ttactt                             3760


<210> SEQ ID NO 3
<211> LENGTH: 1144
<212> TYPE: PRT
<213> ORGANISM: Nicotiana glutinosa

<400> SEQUENCE: 3

Met Ala Ser Ser Ser Ser Ser Ser Arg Trp Ser Tyr Asp Val Phe Leu
1               5                   10                  15

Ser Phe Arg Gly Glu Asp Thr Arg Lys Thr Phe Thr Ser His Leu Tyr
```

-continued

```
            20                  25                  30

Glu Val Leu Asn Asp Lys Gly Ile Lys Thr Phe Gln Asp Asp Lys Arg
        35                  40                  45

Leu Glu Tyr Gly Ala Thr Ile Pro Gly Glu Leu Cys Lys Ala Ile Glu
    50                  55                  60

Glu Ser Gln Phe Ala Ile Val Val Phe Ser Glu Asn Tyr Ala Thr Ser
65                  70                  75                  80

Arg Trp Cys Leu Asn Glu Leu Val Lys Ile Met Glu Cys Lys Thr Arg
                85                  90                  95

Phe Lys Gln Thr Val Ile Pro Ile Phe Tyr Asp Val Asp Pro Ser His
            100                 105                 110

Val Arg Asn Gln Lys Glu Ser Phe Ala Lys Ala Phe Glu Glu His Glu
        115                 120                 125

Thr Lys Tyr Lys Asp Asp Val Glu Gly Ile Gln Arg Trp Arg Ile Ala
    130                 135                 140

Leu Asn Glu Ala Ala Asn Leu Lys Gly Ser Cys Asp Asn Arg Asp Lys
145                 150                 155                 160

Thr Asp Ala Asp Cys Ile Arg Gln Ile Val Asp Gln Ile Ser Ser Lys
                165                 170                 175

Leu Cys Lys Ile Ser Leu Ser Tyr Leu Gln Asn Ile Val Gly Ile Asp
            180                 185                 190

Thr His Leu Glu Lys Ile Glu Ser Leu Leu Glu Ile Gly Ile Asn Gly
        195                 200                 205

Val Arg Ile Met Gly Ile Trp Gly Met Gly Gly Val Gly Lys Thr Thr
    210                 215                 220

Ile Ala Arg Ala Ile Phe Asp Thr Leu Leu Gly Arg Met Asp Ser Ser
225                 230                 235                 240

Tyr Gln Phe Asp Gly Ala Cys Phe Leu Lys Asp Ile Lys Glu Asn Lys
                245                 250                 255

Arg Gly Met His Ser Leu Gln Asn Ala Leu Leu Ser Glu Leu Leu Arg
            260                 265                 270

Glu Lys Ala Asn Tyr Asn Asn Glu Glu Asp Gly Lys His Gln Met Ala
        275                 280                 285

Ser Arg Leu Arg Ser Lys Lys Val Leu Ile Val Leu Asp Asp Ile Asp
    290                 295                 300

Asn Lys Asp His Tyr Leu Glu Tyr Leu Ala Gly Asp Leu Asp Trp Phe
305                 310                 315                 320

Gly Asn Gly Ser Arg Ile Ile Ile Thr Thr Arg Asp Lys His Leu Ile
                325                 330                 335

Glu Lys Asn Asp Ile Ile Tyr Glu Val Thr Ala Leu Pro Asp His Glu
            340                 345                 350

Ser Ile Gln Leu Phe Lys Gln His Ala Phe Gly Lys Glu Val Pro Asn
        355                 360                 365

Glu Asn Phe Glu Lys Leu Ser Leu Glu Val Val Asn Tyr Ala Lys Gly
    370                 375                 380

Leu Pro Leu Ala Leu Lys Val Trp Gly Ser Leu Leu His Asn Leu Arg
385                 390                 395                 400

Leu Thr Glu Trp Lys Ser Ala Ile Glu His Met Lys Asn Asn Ser Tyr
                405                 410                 415

Ser Gly Ile Ile Asp Lys Leu Lys Ile Ser Tyr Asp Gly Leu Glu Pro
            420                 425                 430

Lys Gln Gln Glu Met Phe Leu Asp Ile Ala Cys Phe Leu Arg Gly Glu
        435                 440                 445
```

-continued

```
Glu Lys Asp Tyr Ile Leu Gln Ile Leu Glu Ser Cys His Ile Gly Ala
    450                 455                 460

Glu Tyr Gly Leu Arg Ile Leu Ile Asp Lys Ser Leu Val Phe Ile Ser
465                 470                 475                 480

Glu Tyr Asn Gln Val Gln Met His Asp Leu Ile Gln Asp Met Gly Lys
                485                 490                 495

Tyr Ile Val Asn Phe Gln Lys Asp Pro Gly Glu Arg Ser Arg Leu Trp
            500                 505                 510

Leu Ala Lys Glu Val Glu Glu Val Met Ser Asn Asn Thr Gly Thr Met
        515                 520                 525

Ala Met Glu Ala Ile Trp Val Ser Ser Tyr Ser Ser Thr Leu Arg Phe
    530                 535                 540

Ser Asn Gln Ala Val Lys Asn Met Lys Arg Leu Arg Val Phe Asn Met
545                 550                 555                 560

Gly Arg Ser Ser Thr His Tyr Ala Ile Asp Tyr Leu Pro Asn Asn Leu
                565                 570                 575

Arg Cys Phe Val Cys Thr Asn Tyr Pro Trp Glu Ser Phe Pro Ser Thr
            580                 585                 590

Phe Glu Leu Lys Met Leu Val His Leu Gln Leu Arg His Asn Ser Leu
        595                 600                 605

Arg His Leu Trp Thr Glu Thr Lys His Leu Pro Ser Leu Arg Arg Ile
    610                 615                 620

Asp Leu Ser Trp Ser Lys Arg Leu Thr Arg Thr Pro Asp Phe Thr Gly
625                 630                 635                 640

Met Pro Asn Leu Glu Tyr Val Asn Leu Tyr Gln Cys Ser Asn Leu Glu
                645                 650                 655

Glu Val His His Ser Leu Gly Cys Cys Ser Lys Val Ile Gly Leu Tyr
            660                 665                 670

Leu Asn Asp Cys Lys Ser Leu Lys Arg Phe Pro Cys Val Asn Val Glu
        675                 680                 685

Ser Leu Glu Tyr Leu Gly Leu Arg Ser Cys Asp Ser Leu Glu Lys Leu
    690                 695                 700

Pro Glu Ile Tyr Gly Arg Met Lys Pro Glu Ile Gln Ile His Met Gln
705                 710                 715                 720

Gly Ser Gly Ile Arg Glu Leu Pro Ser Ser Ile Phe Gln Tyr Lys Thr
                725                 730                 735

His Val Thr Lys Leu Leu Leu Trp Asn Met Lys Asn Leu Val Ala Leu
            740                 745                 750

Pro Ser Ser Ile Cys Arg Leu Lys Ser Leu Val Ser Leu Ser Val Ser
        755                 760                 765

Gly Cys Ser Lys Leu Glu Ser Leu Pro Glu Glu Ile Gly Asp Leu Asp
    770                 775                 780

Asn Leu Arg Val Phe Asp Ala Ser Asp Thr Leu Ile Leu Arg Pro Pro
785                 790                 795                 800

Ser Ser Ile Ile Arg Leu Asn Lys Leu Ile Ile Leu Met Phe Arg Gly
                805                 810                 815

Phe Lys Asp Gly Val His Phe Glu Phe Pro Pro Val Ala Glu Gly Leu
            820                 825                 830

His Ser Leu Glu Tyr Leu Asn Leu Ser Tyr Cys Asn Leu Ile Asp Gly
        835                 840                 845

Gly Leu Pro Glu Glu Ile Gly Ser Leu Ser Ser Leu Lys Lys Leu Asp
    850                 855                 860
```

-continued

```
Leu Ser Arg Asn Asn Phe Glu His Leu Pro Ser Ser Ile Ala Gln Leu
865                 870                 875                 880

Gly Ala Leu Gln Ser Leu Asp Leu Lys Asp Cys Gln Arg Leu Thr Gln
                885                 890                 895

Leu Pro Glu Leu Pro Pro Glu Leu Asn Glu Leu His Val Asp Cys His
            900                 905                 910

Met Ala Leu Lys Phe Ile His Tyr Leu Val Thr Lys Arg Lys Lys Leu
        915                 920                 925

His Arg Val Lys Leu Asp Asp Ala His Asn Asp Thr Met Tyr Asn Leu
    930                 935                 940

Phe Ala Tyr Thr Met Phe Gln Asn Ile Ser Ser Met Arg His Asp Ile
945                 950                 955                 960

Ser Ala Ser Asp Ser Leu Ser Leu Thr Val Phe Thr Gly Gln Pro Tyr
                965                 970                 975

Pro Glu Lys Ile Pro Ser Trp Phe His His Gln Gly Trp Asp Ser Ser
            980                 985                 990

Val Ser Val Asn Leu Pro Glu Asn  Trp Tyr Ile Pro Asp  Lys Phe Leu
        995                 1000                1005

Gly Phe  Ala Val Cys Tyr Ser  Arg Ser Leu Ile Asp  Thr Thr Ala
    1010                1015                1020

His Leu  Ile Pro Val Cys Asp  Asp Lys Met Ser Arg  Met Thr Gln
    1025                1030                1035

Lys Leu  Ala Leu Ser Glu Cys  Asp Thr Glu Ser Ser  Asn Tyr Ser
    1040                1045                1050

Glu Trp  Asp Ile His Phe Phe  Phe Val Pro Phe Ala  Gly Leu Trp
    1055                1060                1065

Asp Thr  Ser Lys Ala Asn Gly  Lys Thr Pro Asn Asp  Tyr Gly Ile
    1070                1075                1080

Ile Arg  Leu Ser Phe Ser Gly  Glu Glu Lys Met Tyr  Gly Leu Arg
    1085                1090                1095

Leu Leu  Tyr Lys Glu Gly Pro  Glu Val Asn Ala Leu  Leu Gln Met
    1100                1105                1110

Arg Glu  Asn Ser Asn Glu Pro  Thr Glu His Ser Thr  Gly Ile Arg
    1115                1120                1125

Arg Thr  Gln Tyr Asn Asn Arg  Thr Ser Phe Tyr Glu  Leu Ile Asn
    1130                1135                1140

Gly


<210> SEQ ID NO 4
<211> LENGTH: 3830
<212> TYPE: DNA
<213> ORGANISM: Nicotiana glutinosa
<220> FEATURE:
<221> NAME/KEY: CDS
<222> LOCATION: (60)..(2018)

<400> SEQUENCE: 4

ggcacgagat tttttcacat acagtttctt attcttttca gagaattaac gttgagtcc      59

atg gca tct tct tct tct tct tct aga tgg agc tat gat gtt ttc tta      107
Met Ala Ser Ser Ser Ser Ser Ser Arg Trp Ser Tyr Asp Val Phe Leu
1               5                   10                  15

agt ttt aga ggc gaa gat act cga aaa acg ttt aca agt cac tta tac      155
Ser Phe Arg Gly Glu Asp Thr Arg Lys Thr Phe Thr Ser His Leu Tyr
            20                  25                  30

gaa gtc ttg aat gat aag gga ata aaa acc ttt caa gat gat aaa agg      203
Glu Val Leu Asn Asp Lys Gly Ile Lys Thr Phe Gln Asp Asp Lys Arg
```

-continued

```
        35                  40                  45

cta gag tac ggc gca acc atc cca ggt gaa ctc tgt aaa gct ata gaa      251
Leu Glu Tyr Gly Ala Thr Ile Pro Gly Glu Leu Cys Lys Ala Ile Glu
    50                  55                  60

gag tct caa ttt gcc att gtt gtt ttc tca gag aat tat gca aca tca      299
Glu Ser Gln Phe Ala Ile Val Val Phe Ser Glu Asn Tyr Ala Thr Ser
65                  70                  75                  80

agg tgg tgt ttg aat gaa cta gtg aag atc atg gaa tgc aaa act cga      347
Arg Trp Cys Leu Asn Glu Leu Val Lys Ile Met Glu Cys Lys Thr Arg
                85                  90                  95

ttt aag caa act gtt ata ccg ata ttc tat gat gtg gat cca tca cat      395
Phe Lys Gln Thr Val Ile Pro Ile Phe Tyr Asp Val Asp Pro Ser His
            100                 105                 110

gtt cgg aac caa aag gag agc ttt gca aaa gcc ttt gaa gaa cat gaa      443
Val Arg Asn Gln Lys Glu Ser Phe Ala Lys Ala Phe Glu Glu His Glu
        115                 120                 125

aca aag tat aag gat gat gtt gag gga ata caa aga tgg agg att gct      491
Thr Lys Tyr Lys Asp Asp Val Glu Gly Ile Gln Arg Trp Arg Ile Ala
    130                 135                 140

tta aat gaa gcg gcc aat ctc aaa ggc tca tgt gat aat cgt gac aag      539
Leu Asn Glu Ala Ala Asn Leu Lys Gly Ser Cys Asp Asn Arg Asp Lys
145                 150                 155                 160

act gat gca gac tgt att cga cag att gtt gac caa atc tca tcc aaa      587
Thr Asp Ala Asp Cys Ile Arg Gln Ile Val Asp Gln Ile Ser Ser Lys
                165                 170                 175

tta tgc aag att tct tta tct tat ttg caa aac att gtt gga ata gat      635
Leu Cys Lys Ile Ser Leu Ser Tyr Leu Gln Asn Ile Val Gly Ile Asp
            180                 185                 190

act cat tta gag aaa ata gaa tcc tta cta gag ata gga atc aat ggt      683
Thr His Leu Glu Lys Ile Glu Ser Leu Leu Glu Ile Gly Ile Asn Gly
        195                 200                 205

gtt cgg att atg ggg atc tgg gga atg ggg gga gtc ggt aaa aca aca      731
Val Arg Ile Met Gly Ile Trp Gly Met Gly Gly Val Gly Lys Thr Thr
    210                 215                 220

ata gca aga gct ata ttt gat act ctt tta gga aga atg gat agt tcc      779
Ile Ala Arg Ala Ile Phe Asp Thr Leu Leu Gly Arg Met Asp Ser Ser
225                 230                 235                 240

tat caa ttt gat ggt gct tgt ttc ctt aag gat att aaa gaa aac aaa      827
Tyr Gln Phe Asp Gly Ala Cys Phe Leu Lys Asp Ile Lys Glu Asn Lys
                245                 250                 255

cgt gga atg cat tct ttg caa aat gcc ctt ctc tct gaa ctt tta agg      875
Arg Gly Met His Ser Leu Gln Asn Ala Leu Leu Ser Glu Leu Leu Arg
            260                 265                 270

gaa aaa gct aat tac aat aat gag gag gat gga aag cac caa atg gct      923
Glu Lys Ala Asn Tyr Asn Asn Glu Glu Asp Gly Lys His Gln Met Ala
        275                 280                 285

agt aga ctt cgt tcg aag aag gtc cta att gtg ctt gat gat ata gat      971
Ser Arg Leu Arg Ser Lys Lys Val Leu Ile Val Leu Asp Asp Ile Asp
    290                 295                 300

aat aaa gat cat tat ttg gag tat tta gca ggt gat ctt gat tgg ttt     1019
Asn Lys Asp His Tyr Leu Glu Tyr Leu Ala Gly Asp Leu Asp Trp Phe
305                 310                 315                 320

ggt aat ggt agt aga att att ata aca act aga gac aag cat ttg ata     1067
Gly Asn Gly Ser Arg Ile Ile Ile Thr Thr Arg Asp Lys His Leu Ile
                325                 330                 335

gag aag aat gat ata ata tat gag gtg act gca cta ccc gat cat gaa     1115
Glu Lys Asn Asp Ile Ile Tyr Glu Val Thr Ala Leu Pro Asp His Glu
            340                 345                 350

tcc att caa ttg ttc aaa caa cat gct ttc gga aaa gaa gtt cca aat     1163
```

-continued

```
Ser Ile Gln Leu Phe Lys Gln His Ala Phe Gly Lys Glu Val Pro Asn
        355                 360                 365

gag aat ttt gag aag ctt tca tta gag gta gta aat tat gct aaa ggc     1211
Glu Asn Phe Glu Lys Leu Ser Leu Glu Val Val Asn Tyr Ala Lys Gly
    370                 375                 380

ctt cct tta gcc ctc aaa gtg tgg ggt tct ttg ctg cat aac cta cga     1259
Leu Pro Leu Ala Leu Lys Val Trp Gly Ser Leu Leu His Asn Leu Arg
385                 390                 395                 400

tta act gaa tgg aaa agt gct ata gag cac atg aaa aat aac tct tat     1307
Leu Thr Glu Trp Lys Ser Ala Ile Glu His Met Lys Asn Asn Ser Tyr
                405                 410                 415

tct gga att att gat aag ctc aaa ata agt tat gat gga tta gag ccc     1355
Ser Gly Ile Ile Asp Lys Leu Lys Ile Ser Tyr Asp Gly Leu Glu Pro
            420                 425                 430

aaa caa caa gag atg ttt tta gat ata gca tgc ttc ttg cga ggg gaa     1403
Lys Gln Gln Glu Met Phe Leu Asp Ile Ala Cys Phe Leu Arg Gly Glu
        435                 440                 445

gaa aaa gat tac atc cta caa atc ctt gag agt tgt cat att gga gct     1451
Glu Lys Asp Tyr Ile Leu Gln Ile Leu Glu Ser Cys His Ile Gly Ala
    450                 455                 460

gaa tac ggg tta cgt att tta att gac aaa tct ctt gtg ttc atc tct     1499
Glu Tyr Gly Leu Arg Ile Leu Ile Asp Lys Ser Leu Val Phe Ile Ser
465                 470                 475                 480

gaa tat aat cag gtt caa atg cat gac tta ata cag gat atg ggt aaa     1547
Glu Tyr Asn Gln Val Gln Met His Asp Leu Ile Gln Asp Met Gly Lys
                485                 490                 495

tat ata gtg aat ttt caa aaa gat ccc gga gaa cgt agc aga tta tgg     1595
Tyr Ile Val Asn Phe Gln Lys Asp Pro Gly Glu Arg Ser Arg Leu Trp
            500                 505                 510

ctc gcc aag gaa gtc gaa gaa gtg atg agc aac aac aca ggg acc atg     1643
Leu Ala Lys Glu Val Glu Glu Val Met Ser Asn Asn Thr Gly Thr Met
        515                 520                 525

gca atg gaa gca att tgg gtt tct tct tat tct agt act cta cgc ttt     1691
Ala Met Glu Ala Ile Trp Val Ser Ser Tyr Ser Ser Thr Leu Arg Phe
    530                 535                 540

agc aat cag gcc gtg aaa aat atg aaa agg ctt agg gta ttt aac atg     1739
Ser Asn Gln Ala Val Lys Asn Met Lys Arg Leu Arg Val Phe Asn Met
545                 550                 555                 560

ggg agg tcg tcg aca cat tat gcc atc gat tat ctg ccc aac aac ttg     1787
Gly Arg Ser Ser Thr His Tyr Ala Ile Asp Tyr Leu Pro Asn Asn Leu
                565                 570                 575

cgt tgt ttt gtt tgc act aac tat cct tgg gag tca ttt cca tct aca     1835
Arg Cys Phe Val Cys Thr Asn Tyr Pro Trp Glu Ser Phe Pro Ser Thr
            580                 585                 590

ttt gaa ctc aaa atg ctt gtt cac ctc caa ctc cga cac aat tct ctg     1883
Phe Glu Leu Lys Met Leu Val His Leu Gln Leu Arg His Asn Ser Leu
        595                 600                 605

cgt cat tta tgg aca gaa aca aag aag aag aac aat att gca gag aaa     1931
Arg His Leu Trp Thr Glu Thr Lys Lys Lys Asn Asn Ile Ala Glu Lys
    610                 615                 620

gag gga gat gga att ctt att gaa ttt tgg ggc gat tta caa tgg gca     1979
Glu Gly Asp Gly Ile Leu Ile Glu Phe Trp Gly Asp Leu Gln Trp Ala
625                 630                 635                 640

ttt gcc gtc tct acg gag gat aga tct cag ctg gtc taa aagattgacg      2028
Phe Ala Val Ser Thr Glu Asp Arg Ser Gln Leu Val
                645                 650

cgaacaccag atttcacggg gatgccaaat ttggagtatg tgaatttgta tcaatgtagt   2088

aatcttgaag aagttcacca ttccctggga tgttgcagca aagtcattgg tttatatttg   2148
```

-continued

```
aatgattgta aaagccttaa gaggtttcca tgtgttaacg tggaatctct tgaatatctg   2208

ggtctaagaa gttgcgatag tttagagaaa ttgccagaaa tctacgggag aatgaagccg   2268

gagatacaga ttcacatgca aggctctggg ataagggaac taccatcatc tatttttcag   2328

tacaaaactc atgttaccaa gctattgttg tggaatatga aaaaccttgt agctcttcca   2388

agcagcatat gtaggttgaa aagtttggtt agtctgagtg tgtcgggttg ctcaaaactt   2448

gaaagcttgc cagaagagat aggggattta gacaacttac gggtgtttga tgccagtgat   2508

actctaattt tacgacctcc gtcttccatc atacgcttga acaaacttat aatcttgatg   2568

tttcgaggct tcaaagatgg agtgcacttt gagttccctc ctgtggctga aggattacac   2628

tcattggaat atctgaatct cagttactgc aatctaatag atggaggact tccggaagag   2688

attggatcct tatcctcttt gaaaaagttg gatctcagta gaaataattt tgagcatttg   2748

ccttcaagta tagcccaact tggtgctctt caatccttag acttaaaaga ttgccagagg   2808

cttacacagc taccagaact tcccccagaa ttaaatgaat tgcatgtaga ttgtcatatg   2868

gctctgaaat ttatccatga tttagtaaca aagagaaaga aactacatag agtgaaactt   2928

gatgatgcac acaatgatac tatgtacaat ttgtttgcat ataccatgtt tcagaatatc   2988

tcttccatga ggcatgacat ctctgcttca gattccttgt cactaacagt atttaccggt   3048

caaccgtatc ctgaaaagat cccgagttgg ttccaccatc agggttggga tagtagtgta   3108

tcagtcaatt tgcctgaaaa ttggtatata cctgataaat tcttgggatt tgctgtatgt   3168

tactctcgta gcttaattga cacaacagct cacttgattc ccgtatgtga tgacaagatg   3228

tcgcgcatga cccagaaact tgccttatca gaatgtgata cagaatcatc caactattca   3288

gaatgggata tacatttttt ctttgtacct tttgctggct tatgggatac atctaaggca   3348

aatggaaaaa caccaaatga ttatgggatt attaggctat ctttttctgg agaagagaag   3408

atgtatggac ttcgtttgtt gtataaagaa ggaccagagg ttaatgcctt gttacaaatg   3468

agggaaaata gcaatgaacc aacagaacat tccactggga taaggaggac tcaatataac   3528

aacagaactt ccttttatga gctcatcaat gggtgatgta catatcaaca acgagtttta   3588

aaggattcca acaagtataa ctttttatgc tcaaatcagc tccttgtatt gtggagaaag   3648

ctgagtacga gatgaagttg acgtccgtta tcctttatga tctctctgtt ctttgtgtta   3708

acttgcctac ttcatcagat gaataacaga agcccgttcc tctcattctc aacactgttt   3768

gcacgtctgt tgttacttgt taaaatggat cttgataaag taataacatc tctatattac   3828

tt                                                                  3830


<210> SEQ ID NO 5
<211> LENGTH: 652
<212> TYPE: PRT
<213> ORGANISM: Nicotiana glutinosa

<400> SEQUENCE: 5

Met Ala Ser Ser Ser Ser Ser Ser Arg Trp Ser Tyr Asp Val Phe Leu
1               5                   10                  15

Ser Phe Arg Gly Glu Asp Thr Arg Lys Thr Phe Thr Ser His Leu Tyr
            20                  25                  30

Glu Val Leu Asn Asp Lys Gly Ile Lys Thr Phe Gln Asp Asp Lys Arg
        35                  40                  45

Leu Glu Tyr Gly Ala Thr Ile Pro Gly Glu Leu Cys Lys Ala Ile Glu
    50                  55                  60

Glu Ser Gln Phe Ala Ile Val Val Phe Ser Glu Asn Tyr Ala Thr Ser
```

-continued

```
65                  70                  75                  80

Arg Trp Cys Leu Asn Glu Leu Val Lys Ile Met Glu Cys Lys Thr Arg
                85                  90                  95

Phe Lys Gln Thr Val Ile Pro Ile Phe Tyr Asp Val Asp Pro Ser His
            100                 105                 110

Val Arg Asn Gln Lys Glu Ser Phe Ala Lys Ala Phe Glu Glu His Glu
        115                 120                 125

Thr Lys Tyr Lys Asp Asp Val Glu Gly Ile Gln Arg Trp Arg Ile Ala
    130                 135                 140

Leu Asn Glu Ala Ala Asn Leu Lys Gly Ser Cys Asp Asn Arg Asp Lys
145                 150                 155                 160

Thr Asp Ala Asp Cys Ile Arg Gln Ile Val Asp Gln Ile Ser Ser Lys
                165                 170                 175

Leu Cys Lys Ile Ser Leu Ser Tyr Leu Gln Asn Ile Val Gly Ile Asp
            180                 185                 190

Thr His Leu Glu Lys Ile Glu Ser Leu Leu Glu Ile Gly Ile Asn Gly
        195                 200                 205

Val Arg Ile Met Gly Ile Trp Gly Met Gly Gly Val Gly Lys Thr Thr
    210                 215                 220

Ile Ala Arg Ala Ile Phe Asp Thr Leu Leu Gly Arg Met Asp Ser Ser
225                 230                 235                 240

Tyr Gln Phe Asp Gly Ala Cys Phe Leu Lys Asp Ile Lys Glu Asn Lys
                245                 250                 255

Arg Gly Met His Ser Leu Gln Asn Ala Leu Leu Ser Glu Leu Leu Arg
            260                 265                 270

Glu Lys Ala Asn Tyr Asn Asn Glu Glu Asp Gly Lys His Gln Met Ala
        275                 280                 285

Ser Arg Leu Arg Ser Lys Lys Val Leu Ile Val Leu Asp Asp Ile Asp
    290                 295                 300

Asn Lys Asp His Tyr Leu Glu Tyr Leu Ala Gly Asp Leu Asp Trp Phe
305                 310                 315                 320

Gly Asn Gly Ser Arg Ile Ile Ile Thr Thr Arg Asp Lys His Leu Ile
                325                 330                 335

Glu Lys Asn Asp Ile Ile Tyr Glu Val Thr Ala Leu Pro Asp His Glu
            340                 345                 350

Ser Ile Gln Leu Phe Lys Gln His Ala Phe Gly Lys Glu Val Pro Asn
        355                 360                 365

Glu Asn Phe Glu Lys Leu Ser Leu Glu Val Val Asn Tyr Ala Lys Gly
    370                 375                 380

Leu Pro Leu Ala Leu Lys Val Trp Gly Ser Leu Leu His Asn Leu Arg
385                 390                 395                 400

Leu Thr Glu Trp Lys Ser Ala Ile Glu His Met Lys Asn Asn Ser Tyr
                405                 410                 415

Ser Gly Ile Ile Asp Lys Leu Lys Ile Ser Tyr Asp Gly Leu Glu Pro
            420                 425                 430

Lys Gln Gln Glu Met Phe Leu Asp Ile Ala Cys Phe Leu Arg Gly Glu
        435                 440                 445

Glu Lys Asp Tyr Ile Leu Gln Ile Leu Glu Ser Cys His Ile Gly Ala
    450                 455                 460

Glu Tyr Gly Leu Arg Ile Leu Ile Asp Lys Ser Leu Val Phe Ile Ser
465                 470                 475                 480

Glu Tyr Asn Gln Val Gln Met His Asp Leu Ile Gln Asp Met Gly Lys
                485                 490                 495
```

-continued

```
Tyr Ile Val Asn Phe Gln Lys Asp Pro Gly Glu Arg Ser Arg Leu Trp
            500                 505                 510

Leu Ala Lys Glu Val Glu Glu Val Met Ser Asn Asn Thr Gly Thr Met
        515                 520                 525

Ala Met Glu Ala Ile Trp Val Ser Ser Tyr Ser Ser Thr Leu Arg Phe
    530                 535                 540

Ser Asn Gln Ala Val Lys Asn Met Lys Arg Leu Arg Val Phe Asn Met
545                 550                 555                 560

Gly Arg Ser Ser Thr His Tyr Ala Ile Asp Tyr Leu Pro Asn Asn Leu
                565                 570                 575

Arg Cys Phe Val Cys Thr Asn Tyr Pro Trp Glu Ser Phe Pro Ser Thr
            580                 585                 590

Phe Glu Leu Lys Met Leu Val His Leu Gln Leu Arg His Asn Ser Leu
        595                 600                 605

Arg His Leu Trp Thr Glu Thr Lys Lys Lys Asn Asn Ile Ala Glu Lys
    610                 615                 620

Glu Gly Asp Gly Ile Leu Ile Glu Phe Trp Gly Asp Leu Gln Trp Ala
625                 630                 635                 640

Phe Ala Val Ser Thr Glu Asp Arg Ser Gln Leu Val
                645                 650
```

<210> SEQ ID NO 6
<211> LENGTH: 1818
<212> TYPE: DNA
<213> ORGANISM: Nicotiana glutinosa

<400> SEQUENCE: 6

```
gtacaatagc ttgaattcta ttttgttgtc atttattttt ctctctaact atctttgtcc     60

tttaatttgg tgataatgaa caaatattat tgttttttgt tatgaaacaa taaaagaaga    120

agaacaatat tgcagagaaa gagggagatg gaattcttat tgaattttgg ggcgatttac    180

aatggggtaa gacccctcta tttacagggg aaaaataact tagcctcaaa ataaagctct    240

ttaaaagata gacattcact ctaaatagaa ttctattata acacttttgg cgtacttcct    300

tttttggcta gaattatgat acatgtcttt aaatgaacag aagttgcttt tgtaatttat    360

caggacttat gttgaaactt atgaaaattg ttattgttta tgttgtctaa tactaaatat    420

aaaatacaat aatattttat cgtaattttt taaaaatttg tcaaataatg caaatgaaaa    480

attaaatttt ttggtccttt aaaaatttga gaatgaaaaa gtacgagtta tacttcctaa    540

aagtttgata gtgaataata tgtaaaattt aaagaatgac taatattgga ctaatacttt    600

aaaacaaata acttaatata caaattatag cgagacattt tcattcgttg tactgaatgc    660

aagaaagaaa ggaaaaaaaa actcatttat aatatagttt gtcttctact attttacctt    720

attgcttcaa atttgtattt tatcgatttt gctatatctt atgatttttt tcacggtcaa    780

tattcttctt acaagaataa attttatata cctcaagtgt tttgtcaatt tgataaataa    840

tttttcttat atgatgaact tgtaaaataa tagaattgga ttcttttgct aattagttaa    900

ttcaacgact taattattta ttctcaacat taaaggaaat aatttagttt ttattaattc    960

aaactcttag tatttgctca ttctaatttt cagtccaata agaattcaat tttcaaatag   1020

taagaaaagt catatatttt gaattttatg ttttccgaag cattgtttgt ttgtttaact   1080

ctacgggagt tttctaactc acattttgta taataaaatt ttttgagtag tagttcagta   1140

caactctaat attaatgggc tttaaataag gaaatatata ttacgtaaaa atttaaatca   1200
```

-continued

```
ttttaaagtt ctttcctacc aagtaaataa gggaaaattt aataacaaaa atttagttga   1260

ttttaaaatc ctaaatatta gaaaattaac ttaaaatata atttcgtcta gtgtaaaatt   1320

tatttttaaa gggtaaaaaa gacgaacgac attaagagcc tttgtaattt taatatagta   1380

taaatataaa taatttacct ttattcagtt tcttaacaag taattttcca tatataaaaa   1440

ataaatttct atattcacac aaaaataatg tgttggccct cgtaattcaa atactatcat   1500

tcatttcttg tcgagggagt agtaaatact tttaggaaag ttagcaataa gtaatcaaga   1560

aatcaagaaa acagaggtca tttgatgccc acaaatacaa atgaaaaaac aaaacaaatg   1620

ttacgaaaca ataaaagaac aagaatagcc tcaaagtaaa actctctgat agacatttac   1680

tctaaataga attctattta taacaatcaa aaagtttcta catttataga tagctccact   1740

agccaaatat tttattattg gaatcagcaa aataggttgt ttcttttttt attctcattc   1800

tgtctgtgtt ctaaacag                                                 1818
```

```
<210> SEQ ID NO 7
<211> LENGTH: 1347
<212> TYPE: DNA
<213> ORGANISM: Nicotiana glutinosa

<400> SEQUENCE: 7

tgtacatatc aacaacgagt tttaaaggat tccaacaagt ataacttttt atgctcaaat     60

cagctccttg tattgtggag aaagctgagt acgagatgaa gttgacgtcc gttatccttt    120

atgatctctc tgttctttgt gttaacttgc ctacttcatc agatgaataa cagaagcccg    180

ttcctctcat tctcaacact gtttgcacgt ctgttgttac ttgttaaaat ggatcttgat    240

aaagtaataa catctctata ttacttataa gtggttttaa caagttcact cttttgcttt    300

tgcagttcaa atgggaacac aatgtatatt gagaactaga acaatgacac tgcatatata    360

tatatatatg tatgtatgta attctcgtct tttggactag aataccttgt ttcattatga    420

aatgaattaa catcttcgcc tttgctgaca agtaaccaat tacagatgaa tgaaatcacc    480

tgatcaacat tcattagctt tgtattcttt gacgatttcg gtttcataac tctttcccct    540

gcagttaaaa tatgtagtta gcccgattgc acctctaggg cgcagcggag tattaaaaaa    600

aaaaagatct ttctcatttg tctaagtctt ggtagtcaga attacgagtt tgtataaagt    660

tggctcaaac atcacctttg tataagaaaa atacatacac acacagtaga aaagaaacag    720

ataccttcgc aaatttgatt gggaggtact gatttcttct ttcagttggc gattagcctc    780

ttgtgtcatc tttggagctt cttatgattt ttttttctta ggtaaaattc atttaataat    840

ttgttaatca tattactgtt gggctaaact accccgatac actcataaca tggtgtgata    900

ttgttcgctt tgggccaagc ccgtatggtt ttccccaaaa ggcttcgcac cattaagaga    960

tccatacacc ttaaatgtag actcacaatc ttttcagcta ttaatgtggc actttattcg   1020

catacccaac attatgtgta cactacagga attagagttg gaacagagtt ttaaaactag   1080

tcaaagagtt ttggagctaa caaaactatc ttgataaata taatacaaac aattcgtagt   1140

gttcagaggc ggaataacta tgtgattact gtagaaactt ataaacttta aattttggat   1200

tcgcatttgc ttaccgttga ttttctatct catttatctt ggctggttgt gccataatta   1260

aatccattgg agggacattg taggattagc ttacgtaaat gtgcttgtaa attgaataac   1320

gtgagctaac attgttgaca aattcta                                       1347

<210> SEQ ID NO 8
<211> LENGTH: 4281
```

<212> TYPE: DNA
<213> ORGANISM: Nicotiana glutinosa

<400> SEQUENCE: 8

```
gatcttattc taattatatg acatttgcaa ctgtgaaggc aagaatttct tactctataa     60
ttttttaatt aaatatctaa tctaaaattt ctatagtaaa attgtgattt tgtgctcata    120
ttctcatatt tttcaatgtc tttgtttttc tttcttgttt tttatttact ttagggagga    180
gggcacacag ctcctgagta caaacgtgaa gagtgttttc atatgtttaa aagatggata    240
actcaacaac ctttgtaaac atgtaacccc atcgaagatt aatttattaa atagccatta    300
ttaagcatct gtcttctttt ctttccgatt tttatgtgtg agggtgcaaa aattaactgt    360
aaaaatagta cgggctagcc agttttcgga ctaatcattc aaaatagtca acgtttgtca    420
agtcattgaa aaatatccgc tattttgctg caacagaaac cgtccagcat atatactgga    480
gttgggtgca catgtgtatg tatttccagt acattatgct ggaactccaa cacgcggaaa    540
gttccagcat aatatactgg agattcgagc acctgtgtaa gaacttccag aatattatac    600
tggaccgata tagtttgctg gaaatccagt atattatgct ggagttctag tatatttatg    660
ctggaactcc attatattat cctggagttc cagtatactt atgctggaac tccagtataa    720
tatgctggag tttcactata cttatgctgg aactctagta taatatactg gaatattttc    780
cggatcttga acaatgtgtt cgttcaaatt tatctttaca tgaaaagtga ctaaatttta    840
attacttttg aaagtgtgac tatttttgaa tgagcacttg taaatctggt tatttttgaa    900
tttctcccga attaacttag tctaacaata tcttgttctg actggaaaat tcagtctaat    960
taattactgc attaactatc tcttcttctc tttgtgaatt tttttttttt ttttataaca   1020
aatatgagat aatataaaaa cctctagttc ttctttgaaa aacaggtgag attccaatta   1080
aaacaaaatg ccattcttga acgattttga cagggctttt gcatctatat ccactttttg   1140
ggtcatattt taatttatac ccgctttgca aaaaaattac aagcgtatcc acttttcgca   1200
taaacttcag gcttacgggt ctggagtagc aaaggcaatc acacaaaggt tcagcattct   1260
aggctttttc gaaaacttca gcagaatgct gaagttattt agttcatttg taaaaacttc   1320
agcactaaat aagctgaagt tttgtcctgg attaaataat tttgtcataa agctttttca   1380
ataacttcag cagaagatgc tgaagttatt tagttcattt ataaaaactc cagcactaaa   1440
taagctgaag ttttttcttg aattaattag ttttgtcata aagcttttc aaaaaaacttc   1500
agtgctgaag ttatttagtt cgtttttaaa atcttcagca gaagatggtg aagttattaa   1560
gttcatttgt aaaaacttca gcatcagata agctgaagtt ttgtcctgga ttcattagtt   1620
ttgcagtaaa gctttttcaa aaacttcagc agaagatgct gaagttattt agttcatttg   1680
taaaaacttt agcactaaat atgctgaagt tttgcacagg tattagaaag gtggcgcctg   1740
aaattgtaaa aattaagata tatattaaat aatttaaaaa taaaggtata aattaaatga   1800
gagcgatcaa ataaggcgcc tgcgcaattt ttgatgtcaa ttaggtagca tcaagttaat   1860
tttgcacaat ttttgcgttt ctctatttag attgtttgaa aaaatgacaa ctttaataaa   1920
ttgccgaaat aataaaaaaa taaacaagtt gacagttacc tctttctcct cccgtacaac   1980
cttttcacca ccacccctcc atgtccatga tttgttggtc cctaaagttt aaataataat   2040
aaataaataa ataaaaattg taattaaaat ttagagatca actttggtcg ttaaatatat   2100
attattaaaa tattataccg accgaagttg gtcggtattt tatttatcct aaatatttgg   2160
ttcttttaac ttagtgacca acgttggtcg ctaaattaaa aggaccacca atatagcgac   2220
```

-continued

```
caatccattt tggacgcgtt ttggtcggta tattgtgata agcgaccaac tttggtcgct   2280
atttgtggtc tctttttgcc ggatttctag cagtgtgtac acgcaaatcg aaaaggataa   2340
aatgagattt ttaaggctaa cgagtgcaga attaaatttt aaaacgtaag tttaggtcat   2400
cacatattat gtgattttta aaaaaatgat cttcatatag aatacacacg taacacgctt   2460
gcccaaaaac tattagaaca aaataagtaa cggctatttt taaaccttca atccgtagca   2520
gcccactaat ccctggctcc aattttcttc aataataagt tgtatgcaga aggaaaaaga   2580
ttgttcctag aagttgtatg cgatactaaa caccttcccc ctgttatttt tctgtctgtt   2640
ttctttaaag caacgaatcc tgtgccttga ttctttttctt gtttcctgtg ttagttataa   2700
gtttcaataa tgaaaaataa tatattatat tgggcgtagg atcacaaggg attcaagaag   2760
caacactagt cgggaataga taaaggaaca taatcaataa tcagcatgga aaaggaagaa   2820
gtagcgaaaa ttcggcaaga ataatcaatt taattaatta cagtagctaa ttcttatata   2880
ttaagtttct gagaaaagta acatttcttc acatttatgg acctacattt gttgtcactt   2940
tctatctgcg caaagaaaaa taagaccata gtactgcttt tggttagtac aactgttgac   3000
aaagaaaatt actgggatat tacccttcgt tttctttgta gctttattta tcggcttgta   3060
cttttagttg ttccttgtga acatattact gttgaatttg gtgcagggag ggtgggtggt   3120
ctttgaagga attacctact tcccttctat tacagtgcaa agaaaaccct ataacaataa   3180
taattctaat caactggagt aaacattaag atgaagcttc acaaaaaaat cctacaattt   3240
actttctatt aggagtagtc ggtggcggat ttaggatttt gcgaatatga gtgcactatt   3300
acgaagaggc gaatctagga tataaatttt acaggtttaa cgtttggttc ttactattgc   3360
acccattaca attttgaaat tataagttca aaattattat tttttaattg taattttctt   3420
atatctattt ccatactccg tacttaaaat attgggatca gtttaaccca atagcataca   3480
ctgcattatg cactagttta atatgcaaat tttatttaat catataagat ttttcggtga   3540
caaataacaa ataggaattt taatatgtga aaattttaaa agaataaatc aaaaagaaag   3600
aaagaaagaa aaagaaatgt atttaattaa tacgcaccaa gtgatgccta gttttagaaa   3660
agaaaaaata acaataagat tgtcatagga aaaaggattg aaaggtcgac cagataattt   3720
tttttttttt tttttaccca gaatgatatg ttccacaata tattgtacaa ttttgtcgaa   3780
actttataat aactttctta acgttaataa attgggaaca agtttacgat taaatttcac   3840
atgtgatcat tcaactttgt gtttattatc caacaaaaat gaaaaatatt ttgctagatg   3900
aagactttgt catcctcggt agaaaactaa aatagaaaaa gaattcaatc aatggagacc   3960
tttttctctt tggagcaata attcaattca attgggaagg aatttcctac tcccttctat   4020
taaagttcaa agaaaaccca ataattcctt ttattgcatt aagaagaatt ttcctactag   4080
tgtatatcag ttgactagga caccaataat tctatggagt agagcccatc tcacacaaac   4140
tttttccaat agcaatataa ctcttatctc ttctaatata tataaaaatt tgttgaaaat   4200
atcatctatt attttcttac cacaatcaca atttttttcac atacagtttc ttattctttt   4260
cagagaatta acgttgagtc c                                              4281
```

<210> SEQ ID NO 9
<211> LENGTH: 10881
<212> TYPE: DNA
<213> ORGANISM: Artificial
<220> FEATURE:
<223> OTHER INFORMATION: Artificial construct of PN / c-DNA-N / Intron 3 / 3'-GRS

<400> SEQUENCE: 9

```
gatcttattc taattatatg acatttgcaa ctgtgaaggc aagaatttct tactctataa     60
ttttttaatt aaatatctaa tctaaaattt ctatagtaaa attgtgattt tgtgctcata    120
ttctcatatt tttcaatgtc tttgtttttc tttcttgttt tttatttact ttagggagga    180
gggcacacag ctcctgagta caaacgtgaa gagtgttttc atatgtttaa aagatggata    240
actcaacaac ctttgtaaac atgtaacccc atcgaagatt aatttattaa atagccatta    300
ttaagcatct gtcttctttt ctttccgatt tttatgtgtg agggtgcaaa aattaactgt    360
aaaaatagta cgggctagcc agttttcgga ctaatcattc aaaatagtca acgtttgtca    420
agtcattgaa aaatatccgc tattttgctg caacagaaac cgtccagcat atatactgga    480
gttgggtgca catgtgtatg tatttccagt acattatgct ggaactccaa cacgcggaaa    540
gttccagcat aatatactgg agattcgagc acctgtgtaa gaacttccag aatattatac    600
tggaccgata tagtttgctg gaaatccagt atattatgct ggagttctag tatatttatg    660
ctggaactcc attatattat cctggagttc cagtatactt atgctggaac tccagtataa    720
tatgctggag tttcactata cttatgctgg aactctagta taatatactg gaatattttc    780
cggatcttga acaatgtgtt cgttcaaatt tatctttaca tgaaaagtga ctaaatttta    840
attactttg aaagtgtgac tatttttgaa tgagcacttg taaatctggt tatttttgaa     900
tttctcccga attaacttag tctaacaata tcttgttctg actggaaaat tcagtctaat    960
taattactgc attaactatc tcttcttctc tttgtgaatt tttttttttt ttttataaca   1020
aatatgagat aatataaaaa cctctagttc ttctttgaaa aacaggtgag attccaatta   1080
aaacaaaatg ccattcttga acgattttga cagggctttt gcatctatat ccactttttg   1140
ggtcatattt taatttatac ccgctttgca aaaaaattac aagcgtatcc acttttcgca   1200
taaacttcag gcttacgggt ctggagtagc aaaggcaatc acacaaaggt tcagcattct   1260
aggctttttc gaaaacttca gcagaatgct gaagttattt agttcatttg taaaaacttc   1320
agcactaaat aagctgaagt tttgtcctgg attaaataat tttgtcataa agctttttca   1380
ataacttcag cagaagatgc tgaagttatt tagttcattt ataaaaactc cagcactaaa   1440
taagctgaag ttttttcttg aattaattag ttttgtcata aagcttttttc aaaaaacttc  1500
agtgctgaag ttatttagtt cgtttttaaa atcttcagca gaagatggtg aagttattaa   1560
gttcatttgt aaaaacttca gcatcagata agctgaagtt ttgtcctgga ttcattagtt   1620
ttgcagtaaa gctttttcaa aaacttcagc agaagatgct gaagttattt agttcatttg   1680
taaaaacttt agcactaaat atgctgaagt tttgcacagg tattagaaag gtggcgcctg   1740
aaattgtaaa aattaagata tatattaaat aatttaaaaa taaaggtata aattaaatga   1800
gagcgatcaa ataaggcgcc tgcgcaattt ttgatgtcaa ttaggtagca tcaagttaat   1860
tttgcacaat ttttgcgttt ctctatttag attgtttgaa aaaatgacaa ctttaataaa   1920
ttgccgaaat aataaaaaaa taaacaagtt gacagttacc tctttctcct cccgtacaac   1980
cttttcacca ccacccctcc atgtccatga tttgttggtc cctaaagttt aaataataat   2040
aaataaataa ataaaaattg taattaaaat ttagagatca actttggtcg ttaaatatat   2100
attattaaaa tattataccg accgaagttg gtcggtattt tatttatcct aaatatttgg   2160
ttcttttaac ttagtgacca acgttggtcg ctaaattaaa aggaccacca atatagcgac   2220
caatccattt tggacgcgtt ttggtcggta tattgtgata agcgaccaac tttggtcgct   2280
atttgtggtc tctttttgcc ggatttctag cagtgtgtac acgcaaatcg aaaaggataa   2340
```

-continued

```
aatgagattt ttaaggctaa cgagtgcaga attaaatttt aaaacgtaag tttaggtcat   2400
cacatattat gtgattttta aaaaaatgat cttcatatag aatacacacg taacacgctt   2460
gcccaaaaac tattagaaca aaataagtaa cggctatttt taaaccttca atccgtagca   2520
gcccactaat ccctggctcc aattttcttc aataataagt tgtatgcaga aggaaaaaga   2580
ttgttcctag aagttgtatg cgatactaaa caccttcccc ctgttatttt tctgtctgtt   2640
ttctttaaag caacgaatcc tgtgccttga ttcttttctt gtttcctgtg ttagttataa   2700
gtttcaataa tgaaaaataa tatattatat tgggcgtagg atcacaaggg attcaagaag   2760
caacactagt cgggaataga taaaggaaca taatcaataa tcagcatgga aaaggaagaa   2820
gtagcgaaaa ttcggcaaga ataatcaatt taattaatta cagtagctaa ttcttatata   2880
ttaagtttct gagaaaagta acatttcttc acatttatgg acctacattt gttgtcactt   2940
tctatctgcg caaagaaaaa taagaccata gtactgcttt tggttagtac aactgttgac   3000
aaagaaaatt actgggatat tacccttcgt tttctttgta gctttattta tcggcttgta   3060
cttttagttg ttccttgtga acatattact gttgaatttg gtgcagggag ggtgggtggt   3120
ctttgaagga attacctact tcccttctat tacagtgcaa agaaaaccct ataacaataa   3180
taattctaat caactggagt aaacattaag atgaagcttc acaaaaaaat cctacaattt   3240
actttctatt aggagtagtc ggtggcggat ttaggatttt gcgaatatga gtgcactatt   3300
acgaagaggc gaatctagga tataaatttt acaggtttaa cgtttggttc ttactattgc   3360
acccattaca attttgaaat tataagttca aaattattat tttttaattg taattttctt   3420
atatctattt ccatactccg tacttaaaat attgggatca gtttaaccca atagcataca   3480
ctgcattatg cactagttta atatgcaaat tttatttaat catataagat ttttcggtga   3540
caaataacaa ataggaattt taatatgtga aaattttaaa agaataaatc aaaaagaaag   3600
aaagaaagaa aaagaaatgt atttaattaa tacgcaccaa gtgatgccta gttttagaaa   3660
agaaaaaata acaataagat tgtcatagga aaaaggattg aaaggtcgac cagataattt   3720
ttttttttt ttttttacca gaatgatatg ttccacaata tattgtacaa ttttgtcgaa   3780
actttataat aactttctta acgttaataa attgggaaca agtttacgat taaatttcac   3840
atgtgatcat tcaactttgt gtttattatc caacaaaaat gaaaaatatt ttgctagatg   3900
aagactttgt catcctcggt agaaaactaa aatagaaaaa gaattcaatc aatggagacc   3960
tttttctctt tggagcaata attcaattca attgggaagg aatttcctac tcccttctat   4020
taaagttcaa agaaaaccca ataattcctt ttattgcatt aagaagaatt ttcctactag   4080
tgtatatcag ttgactagga caccaataat tctatggagt agagcccatc tcacacaaac   4140
tttttccaat agcaatataa ctcttatctc ttctaatata tataaaaatt tgttgaaaat   4200
atcatctatt attttcttac cacaatcaca attttttcac atacagtttc ttattctttt   4260
cagagaatta acgttgagtc catggcatct tcttcttctt cttctagatg gagctatgat   4320
gttttcttaa gttttagagg cgaagatact cgaaaaacgt ttacaagtca cttatacgaa   4380
gtcttgaatg ataagggaat aaaaaccttt caagatgata aaaggctaga gtacggcgca   4440
accatcccag gtgaactctg taaagctata gaagagtctc aatttgccat tgttgttttc   4500
tcagagaatt atgcaacatc aaggtggtgt ttgaatgaac tagtgaagat catggaatgc   4560
aaaactcgat ttaagcaaac tgttataccg atattctatg atgtggatcc atcacatgtt   4620
cggaaccaaa aggagagctt tgcaaaagcc tttgaagaac atgaaacaaa gtataaggat   4680
```

-continued

```
gatgttgagg gaatacaaag atggaggatt gctttaaatg aagcggccaa tctcaaaggc   4740
tcctgtgata atcgtgacaa gactgatgca gactgtattc gacagattgt tgaccaaatc   4800
tcatccaaat tatgcaagat ttctttatct tatttgcaaa acattgttgg aatagatact   4860
catttagaga aaatagaatc cttactagag ataggaatca atggtgttcg gattatgggg   4920
atctggggaa tgggggagt cggtaaaaca acaatagcaa gagctatatt tgatactctt   4980
ttaggaagaa tggatagttc ctatcaattt gatggtgctt gtttccttaa ggatattaaa   5040
gaaaacaaac gtggaatgca ttctttgcaa aatgcccttc tctctgaact tttaagggaa   5100
aaagctaatt acaataatga ggaggatgga aagcaccaaa tggctagtag acttcgttcg   5160
aagaaggtcc taattgtgct tgatgatata gataataaag atcattattt ggagtattta   5220
gcaggtgatc ttgattggtt tggtaatggt agtagaatta ttataacaac tagagacaag   5280
catttgatag agaagaatga tataatatat gaggtgactg cactacccga tcatgaatcc   5340
attcaattgt tcaaacaaca tgctttcgga aaagaagttc caaatgagaa ttttgagaag   5400
ctttcattag aggtagtaaa ttatgctaaa ggccttcctt tagccctcaa agtgtggggt   5460
tctttgctgc ataacctacg attaactgaa tggaaaagtg ctatagagca catgaaaaat   5520
aactcttatt ctggaattat tgataagctc aaaataagtt atgatggatt agagcccaaa   5580
caacaagaga tgtttttaga tatagcatgc ttcttgcgag gggaagaaaa agattacatc   5640
ctacaaatcc ttgagagttg tcatattgga gctgaatacg ggttacgtat tttaattgac   5700
aaatctcttg tgttcatctc tgaatataat caggttcaaa tgcatgactt aatacaggat   5760
atgggtaaat atatagtgaa ttttcaaaaa gatcccggag aacgtagcag attatggctc   5820
gccaaggaag tcgaagaagt gatgagcaac aacacaggga ccatggcaat ggaagcaatt   5880
tgggtttctt cttattctag tactctacgc tttagcaatc aggccgtgaa aaatatgaaa   5940
aggcttaggg tatttaacat ggggaggtcg tcgacacatt atgccatcga ttatctgccc   6000
aacaacttgc gttgttttgt ttgcactaac tatccttggg agtcatttcc atctacattt   6060
gaactcaaaa tgcttgttca cctccaactc cgacacaatt ctctgcgtca tttatggaca   6120
gaaacaaagg tacaatagct tgaattctat tttgttgtca tttatttttc tctctaacta   6180
tctttgtcct ttaatttggt gataatgaac aaatattatt gttttttgtt atgaaacaat   6240
aaaagaagaa gaacaatatt gcagagaaag agggagatgg aattcttatt gaattttggg   6300
gcgatttaca atggggtaag acccctctat ttacagggga aaaataactt agcctcaaaa   6360
taaagctctt taaaagatag acattcactc taaatagaat tctattataa cacttttggc   6420
gtacttcctt ttttggctag aattatgata catgtcttta aatgaacaga agttgctttt   6480
gtaatttatc aggacttatg ttgaaactta tgaaaattgt tattgtttat gttgtctaat   6540
actaaatata aaatacaata atattttatc gtaatttttt aaaaatttgt caaataatgc   6600
aaatgaaaaa ttaaattttt tggtccttta aaaatttgag aatgaaaaag tacgagttat   6660
acttcctaaa agtttgatag tgaataatat gtaaaattta aagaatgact aatattggac   6720
taatacttta aaacaaataa cttaatatac aaattatagc gagacatttt cattcgttgt   6780
actgaatgca agaaagaaag gaaaaaaaaa ctcatttata atatagtttg tcttctacta   6840
ttttacctta ttgcttcaaa tttgtatttt atcgattttg ctatatctta tgattttttt   6900
cacggtcaat attcttctta caagaataaa ttttatatac ctcaagtgtt ttgtcaattt   6960
gataaataat ttttcttata tgatgaactt gtaaaataat agaattggat tcttttgcta   7020
attagttaat tcaacgactt aattatttat tctcaacatt aaaggaaata atttagtttt   7080
```

-continued

```
tattaattca aactcttagt atttgctcat tctaattttc agtccaataa gaattcaatt   7140
ttcaaatagt aagaaaagtc atatattttg aattttatgt tttccgaagc attgtttgtt   7200
tgtttaactc tacgggagtt ttctaactca cattttgtat aataaaattt tttgagtagt   7260
agttcagtac aactctaata ttaatgggct ttaaataagg aaatatatat tacgtaaaaa   7320
tttaaatcat tttaaagttc tttcctacca agtaaataag ggaaaattta ataacaaaaa   7380
tttagttgat tttaaaatcc taaatattag aaaattaact taaaatataa tttcgtctag   7440
tgtaaaattt atttttaaag ggtaaaaaag acgaacgaca ttaagagcct ttgtaatttt   7500
aatatagtat aaatataaat aatttacctt tattcagttt cttaacaagt aattttccat   7560
atataaaaaa taaatttcta tattcacaca aaaataatgt gttggccctc gtaattcaaa   7620
tactatcatt catttcttgt cgagggagta gtaaatactt ttaggaaagt tagcaataag   7680
taatcaagaa atcaagaaaa cagaggtcat ttgatgccca caaatacaaa tgaaaaaaca   7740
aaacaaatgt tacgaaacaa taaaagaaca agaatagcct caaagtaaaa ctctctgata   7800
gacatttact ctaaatagaa ttctatttat aacaatcaaa aagtttctac atttatagat   7860
agctccacta gccaaatatt ttattattgg aatcagcaaa ataggttgtt tcttttttta   7920
ttctcattct gtctgtgttc taaacagcat ttgccgtctc tacggaggat agatctcagc   7980
tggtctaaaa gattgacgcg aacaccagat ttcacgggga tgccaaattt ggagtatgtg   8040
aatttgtatc aatgtagtaa tcttgaagaa gttcaccatt ccctgggatg ttgcagcaaa   8100
gtcattggtt tatatttgaa tgattgtaaa agccttaaga ggtttccatg tgttaacgtg   8160
gaatctcttg aatatctggg tctaagaagt tgcgatagtt tagagaaatt gccagaaatc   8220
tacgggagaa tgaagccgga gatacagatt cacatgcaag gctctgggat aagggaacta   8280
ccatcatcta tttttcagta caaaactcat gttaccaagc tattgttgtg gaatatgaaa   8340
aaccttgtag ctcttccaag cagcatatgt aggttgaaaa gtttggttag tctgagtgtg   8400
tcgggttgct caaaacttga aagcttgcca gaagagatag ggatttaga caacttacgg    8460
gtgtttgatg ccagtgatac tctaatttta cgacctccgt cttccatcat acgcttgaac   8520
aaacttataa tcttgatgtt tcgaggcttc aaagatggag tgcactttga gttccctcct   8580
gtggctgaag gattacactc attggaatat ctgaatctca gttactgcaa tctaatagat   8640
ggaggacttc cggaagagat tggatcctta tcctctttga aaaagttgga tctcagtaga   8700
aataattttg agcatttgcc ttcaagtata gcccaacttg gtgctcttca atccttagac   8760
ttaaaagatt gccagaggct tacacagcta ccagaacttc ccccagaatt aaatgaattg   8820
catgtagatt gtcatatggc tctgaaattt atccattatt tagtaacaaa gagaaagaaa   8880
ctacatagag tgaaacttga tgatgcacac aatgatacta tgtacaattt gtttgcatat   8940
accatgtttc agaatatctc ttccatgagg catgacatct ctgcttcaga ttccttgtca   9000
ctaacagtat ttaccggtca accgtatcct gaaaagatcc cgagttggtt ccaccatcag   9060
ggttgggata gtagtgtatc agtcaatttg cctgaaaatt ggtatatacc tgataaattc   9120
ttgggatttg ctgtatgtta ctctcgtagc ttaattgaca caacagctca cttgattccc   9180
gtatgtgatg acaagatgtc gcgcatgacc cagaaacttg ccttatcaga atgtgataca   9240
gaatcatcca actattcaga atgggatata catttttcct ttgtaccttt tgctggctta   9300
tgggatacat ctaaggcaaa tggaaaaaca ccaaatgatt atgggattat taggctatct   9360
ttttctggag aagagaagat gtatggactt cgtttgttgt ataaagaagg accagaggtt   9420
```

-continued

```
aatgccttgt tacaaatgag ggaaaatagc aatgaaccaa cagaacattc cactgggata   9480

aggaggactc aatataacaa cagaacttcc ttttatgagc tcatcaatgg gtgatgtaca   9540

tatcaacaac gagttttaaa ggattccaac aagtataact ttttatgctc aaatcagctc   9600

cttgtattgt ggagaaagct gagtacgaga tgaagttgac gtccgttatc ctttatgatc   9660

tctctgttct ttgtgttaac ttgcctactt catcagatga ataacagaag cccgttcctc   9720

tcattctcaa cactgtttgc acgtctgttg ttacttgtta aaatggatct tgataaagta   9780

ataacatctc tatattactt ataagtggtt ttaacaagtt cactcttttg cttttgcagt   9840

tcaaatggga acacaatgta tattgagaac tagaacaatg acactgcata tatatatata   9900

tatgtatgta tgtaattctc gtcttttgga ctagaatacc ttgtttcatt atgaaatgaa   9960

ttaacatctt cgcctttgct gacaagtaac caattacaga tgaatgaaat cacctgatca  10020

acattcatta gctttgtatt ctttgacgat ttcggtttca taactctttc ccctgcagtt  10080

aaaatatgta gttagcccga ttgcacctct agggcgcagc ggagtattaa aaaaaaaaag  10140

atctttctca tttgtctaag tcttggtagt cagaattacg agtttgtata aagttggctc  10200

aaacatcacc tttgtataag aaaaatacat acacacacag tagaaaagaa acagatacct  10260

tcgcaaattt gattgggagg tactgatttc ttctttcagt tggcgattag cctcttgtgt  10320

catctttgga gcttcttatg attttttttt cttaggtaaa attcatttaa taatttgtta  10380

atcatattac tgttgggcta aactaccccg atacactcat aacatggtgt gatattgttc  10440

gctttgggcc aagcccgtat ggttttcccc aaaaggcttc gcaccattaa gagatccata  10500

caccttaaat gtagactcac aatcttttca gctattaatg tggcacttta ttcgcatacc  10560

caacattatg tgtacactac aggaattaga gttggaacag agttttaaaa ctagtcaaag  10620

agttttggag ctaacaaaac tatcttgata aatataatac aaacaattcg tagtgttcag  10680

aggcggaata actatgtgat tactgtagaa acttataaac tttaaatttt ggattcgcat  10740

ttgcttaccg ttgattttct atctcattta tcttggctgg ttgtgccata attaaatcca  10800

ttggagggac attgtaggat tagcttacgt aaatgtgctt gtaaattgaa taacgtgagc  10860

taacattgtt gacaaattct a                                            10881
```

<210> SEQ ID NO 10
<211> LENGTH: 24
<212> TYPE: DNA
<213> ORGANISM: artificial
<220> FEATURE:
<223> OTHER INFORMATION: primer 1

<400> SEQUENCE: 10

```
ggcacgagat tttttcacat acag                                            24
```

<210> SEQ ID NO 11
<211> LENGTH: 23
<212> TYPE: DNA
<213> ORGANISM: artificial
<220> FEATURE:
<223> OTHER INFORMATION: primer 2

<400> SEQUENCE: 11

```
aagtaatata gagatgttat tac                                             23
```

<210> SEQ ID NO 12
<211> LENGTH: 30
<212> TYPE: DNA
<213> ORGANISM: artificial

<220> FEATURE:
<223> OTHER INFORMATION: primer 3

<400> SEQUENCE: 12
atggcatctt cttcttcttc ttctagatgg 30

<210> SEQ ID NO 13
<211> LENGTH: 30
<212> TYPE: DNA
<213> ORGANISM: artificial
<220> FEATURE:
<223> OTHER INFORMATION: primer 4

<400> SEQUENCE: 13
cccattgatg agctcataaa aggaagttct 30

<210> SEQ ID NO 14
<211> LENGTH: 28
<212> TYPE: DNA
<213> ORGANISM: artificial
<220> FEATURE:
<223> OTHER INFORMATION: primer 5

<400> SEQUENCE: 14
gtacaatagc ttgaattcta ttttgttg 28

<210> SEQ ID NO 15
<211> LENGTH: 27
<212> TYPE: DNA
<213> ORGANISM: artificial
<220> FEATURE:
<223> OTHER INFORMATION: primer 6

<400> SEQUENCE: 15
ctgtttagaa cacagacaga atgagaa 27

<210> SEQ ID NO 16
<211> LENGTH: 5253
<212> TYPE: DNA
<213> ORGANISM: Artificial
<220> FEATURE:
<223> OTHER INFORMATION: cDNA-N/intron construct: E1-E2-E3-I3-E4-E5

<400> SEQUENCE: 16
atggcatctt cttcttcttc ttctagatgg agctatgatg ttttcttaag ttttagaggc 60
gaagatactc gaaaaacgtt tacaagtcac ttatacgaag tcttgaatga taagggaata 120
aaaacctttc aagatgataa aaggctagag tacggcgcaa ccatcccagg tgaactctgt 180
aaagctatag aagagtctca atttgccatt gttgttttct cagagaatta tgcaacatca 240
aggtggtgtt tgaatgaact agtgaagatc atggaatgca aaactcgatt taagcaaact 300
gttataccga tattctatga tgtggatcca tcacatgttc ggaaccaaaa ggagagcttt 360
gcaaaagcct ttgaagaaca tgaaacaaag tataaggatg atgttgaggg aatacaaaga 420
tggaggattg ctttaaatga agcggccaat ctcaaaggct cctgtgataa tcgtgacaag 480
actgatgcag actgtattcg acagattgtt gaccaaatct catccaaatt atgcaagatt 540
tctttatctt atttgcaaaa cattgttgga atagatactc atttagagaa aatagaatcc 600
ttactagaga taggaatcaa tggtgttcgg attatgggga tctggggaat ggggggagtc 660
ggtaaaacaa caatagcaag agctatattt gatactcttt taggaagaat ggatagttcc 720
tatcaatttg atggtgcttg tttccttaag gatattaaag aaaacaaacg tggaatgcat 780

-continued

```
tctttgcaaa atgcccttct ctctgaactt ttaagggaaa aagctaatta caataatgag     840
gaggatggaa agcaccaaat ggctagtaga cttcgttcga agaaggtcct aattgtgctt     900
gatgatatag ataataaaga tcattatttg gagtatttag caggtgatct tgattggttt     960
ggtaatggta gtagaattat tataacaact agagacaagc atttgataga gaagaatgat    1020
ataatatatg aggtgactgc actacccgat catgaatcca ttcaattgtt caaacaacat    1080
gctttcggaa aagaagttcc aaatgagaat tttgagaagc tttcattaga ggtagtaaat    1140
tatgctaaag gccttccttt agccctcaaa gtgtggggtt ctttgctgca taacctacga    1200
ttaactgaat ggaaaagtgc tatagagcac atgaaaaata actcttattc tggaattatt    1260
gataagctca aaataagtta tgatggatta gagcccaaac aacaagagat gtttttagat    1320
atagcatgct tcttgcgagg ggaagaaaaa gattacatcc tacaaatcct tgagagttgt    1380
catattggag ctgaatacgg gttacgtatt ttaattgaca aatctcttgt gttcatctct    1440
gaatataatc aggttcaaat gcatgactta atacaggata tgggtaaata tatagtgaat    1500
tttcaaaaag atcccggaga acgtagcaga ttatggctcg ccaaggaagt cgaagaagtg    1560
atgagcaaca acacagggac catggcaatg gaagcaattt gggtttcttc ttattctagt    1620
actctacgct ttagcaatca ggccgtgaaa aatatgaaaa ggcttagggt atttaacatg    1680
gggaggtcgt cgacacatta tgccatcgat tatctgccca acaacttgcg ttgttttgtt    1740
tgcactaact atccttggga gtcatttcca tctacatttg aactcaaaat gcttgttcac    1800
ctccaactcc gacacaattc tctgcgtcat ttatggacag aaacaaaggt acaatagctt    1860
gaattctatt ttgttgtcat ttatttttct ctctaactat ctttgtcctt taatttggtg    1920
ataatgaaca aatattattg ttttttgtta tgaaacaata aaagaagaag aacaatattg    1980
cagagaaaga gggagatgga attcttattg aattttgggg cgatttacaa tggggtaaga    2040
cccctctatt tacaggggaa aaataactta gcctcaaaat aaagctcttt aaaagataga    2100
cattcactct aaatagaatt ctattataac acttttggcg tacttccttt tttggctaga    2160
attatgatac atgtctttaa atgaacagaa gttgcttttg taatttatca ggacttatgt    2220
tgaaacttat gaaaattgtt attgtttatg ttgtctaata ctaaatataa aatacaataa    2280
tattttatcg taatttttta aaaatttgtc aaataatgca aatgaaaaat taaatttttt    2340
ggtcctttaa aaatttgaga atgaaaaagt acgagttata cttcctaaaa gtttgatagt    2400
gaataatatg taaaatttaa agaatgacta atattggact aatactttaa aacaaataac    2460
ttaatataca aattatagcg agacattttc attcgttgta ctgaatgcaa gaaagaaagg    2520
aaaaaaaaac tcatttataa tatagtttgt cttctactat tttaccttat tgcttcaaat    2580
ttgtatttta tcgattttgc tatatcttat gatttttttc acggtcaata ttcttcttac    2640
aagaataaat tttatatacc tcaagtgttt tgtcaatttg ataaataatt tttcttatat    2700
gatgaacttg taaaataata gaattggatt cttttgctaa ttagttaatt caacgactta    2760
attatttatt ctcaacatta aaggaaataa tttagttttt attaattcaa actcttagta    2820
tttgctcatt ctaattttca gtccaataag aattcaattt tcaaatagta agaaaagtca    2880
tatattttga attttatgtt ttccgaagca ttgtttgttt gtttaactct acgggagttt    2940
tctaactcac attttgtata ataaaatttt ttgagtagta gttcagtaca actctaatat    3000
taatgggctt taaataagga aatatatatt acgtaaaaat ttaaatcatt ttaaagttct    3060
ttcctaccaa gtaaataagg gaaaatttaa taacaaaaat ttagttgatt ttaaaatcct    3120
aaatattaga aaattaactt aaaatataat ttcgtctagt gtaaaattta tttttaaagg    3180
```

-continued

```
gtaaaaaaga cgaacgacat taagagcctt tgtaatttta atatagtata aatataaata   3240
atttaccttt attcagtttc ttaacaagta attttccata tataaaaaat aaatttctat   3300
attcacacaa aaataatgtg ttggccctcg taattcaaat actatcattc atttcttgtc   3360
gagggagtag taaatacttt taggaaagtt agcaataagt aatcaagaaa tcaagaaaac   3420
agaggtcatt tgatgcccac aaatacaaat gaaaaaacaa aacaaatgtt acgaaacaat   3480
aaaagaacaa gaatagcctc aaagtaaaac tctctgatag acatttactc taaatagaat   3540
tctatttata acaatcaaaa agtttctaca tttatagata gctccactag ccaaatattt   3600
tattattgga atcagcaaaa taggttgttt ctttttttat tctcattctg tctgtgttct   3660
aaacagcatt tgccgtctct acggaggata gatctcagct ggtctaaaag attgacgcga   3720
acaccagatt tcacggggat gccaaatttg gagtatgtga atttgtatca atgtagtaat   3780
cttgaagaag ttcaccattc cctgggatgt tgcagcaaag tcattggttt atatttgaat   3840
gattgtaaaa gccttaagag gtttccatgt gttaacgtgg aatctcttga atatctgggt   3900
ctaagaagtt gcgatagttt agagaaattg ccagaaatct acgggagaat gaagccggag   3960
atacagattc acatgcaagg ctctgggata agggaactac catcatctat ttttcagtac   4020
aaaactcatg ttaccaagct attgttgtgg aatatgaaaa accttgtagc tcttccaagc   4080
agcatatgta ggttgaaaag tttggttagt ctgagtgtgt cgggttgctc aaaacttgaa   4140
agcttgccag aagagatagg ggatttagac aacttacggg tgtttgatgc cagtgatact   4200
ctaattttac gacctccgtc ttccatcata cgcttgaaca aacttataat cttgatgttt   4260
cgaggcttca aagatggagt gcactttgag ttccctcctg tggctgaagg attacactca   4320
ttggaatatc tgaatctcag ttactgcaat ctaatagatg gaggacttcc ggaagagatt   4380
ggatccttat cctctttgaa aaagttggat ctcagtagaa ataattttga gcatttgcct   4440
tcaagtatag cccaacttgg tgctcttcaa tccttagact taaaagattg ccagaggctt   4500
acacagctac cagaacttcc cccagaatta aatgaattgc atgtagattg tcatatggct   4560
ctgaaattta tccattattt agtaacaaag agaaagaaac tacatagagt gaaacttgat   4620
gatgcacaca atgatactat gtacaatttg tttgcatata ccatgtttca gaatatctct   4680
tccatgaggc atgacatctc tgcttcagat tccttgtcac taacagtatt taccggtcaa   4740
ccgtatcctg aaaagatccc gagttggttc caccatcagg gttgggatag tagtgtatca   4800
gtcaatttgc ctgaaaattg gtatatacct gataaattct tgggatttgc tgtatgttac   4860
tctcgtagct taattgacac aacagctcac ttgattcccg tatgtgatga caagatgtcg   4920
cgcatgaccc agaaacttgc cttatcagaa tgtgatacag aatcatccaa ctattcagaa   4980
tgggatatac atttttcttt tgtacctttt gctggcttat gggatacatc taaggcaaat   5040
ggaaaaacac caaatgatta tgggattatt aggctatctt tttctggaga agagaagatg   5100
tatggacttc gtttgttgta taaagaagga ccagaggtta atgccttgtt acaaatgagg   5160
gaaaatagca atgaaccaac agaacattcc actgggataa ggaggactca atataacaac   5220
agaacttcct tttatgagct catcaatggg tga                                5253
```

```
<210> SEQ ID NO 17
<211> LENGTH: 5483
<212> TYPE: DNA
<213> ORGANISM: Artificial
<220> FEATURE:
<223> OTHER INFORMATION: cDNA-N/intron construct:  E1-I1-E2-E3-I3-E4-E5
```

-continued

<400> SEQUENCE: 17

```
atggcatctt cttcttcttc ttctagatgg agctatgatg ttttcttaag ttttagaggc     60
gaagatactc gaaaaacgtt tacaagtcac ttatacgaag tcttgaatga taagggaata    120
aaaacctttc aagatgataa aaggctagag tacggcgcaa ccatcccagg tgaactctgt    180
aaagctatag aagagtctca atttgccatt gttgttttct cagagaatta tgcaacatca    240
aggtggtgtt tgaatgaact agtgaagatc atggaatgca aaactcgatt taagcaaact    300
gttataccga tattctatga tgtggatcca tcacatgttc ggaaccaaaa ggagagcttt    360
gcaaaagcct ttgaagaaca tgaaacaaag tataaggatg atgttgaggg aatacaaaga    420
tggaggattg ctttaaatga agcggccaat ctcaaaggct cctgtgataa tcgtgacaag    480
tgagttaaaa acatataagc tgaatacttt gcattcaaat gagttaaaca taatcttaaa    540
taaatttttc aattttttgg aataaattga tagttgatta tatatgtttc tatcagttaa    600
ttacaaactc aataacatta ttacgtagat aaaattttta ttagttcttc aaagagtttg    660
atttatgtgc acactctttg tatatatcac aatcttttta cttttgtagg actgatgcag    720
actgtattcg acagattgtt gaccaaatct catccaaatt atgcaagatt tctttatctt    780
atttgcaaaa cattgttgga atagatactc atttagagaa aatagaatcc ttactagaga    840
taggaatcaa tggtgttcgg attatgggga tctggggaat ggggggagtc ggtaaaacaa    900
caatagcaag agctatattt gatactcttt taggaagaat ggatagttcc tatcaatttg    960
atggtgcttg tttccttaag gatattaaag aaaacaaacg tggaatgcat tctttgcaaa   1020
atgcccttct ctctgaactt ttaagggaaa aagctaatta caataatgag gaggatggaa   1080
agcaccaaat ggctagtaga cttcgttcga agaaggtcct aattgtgctt gatgatatag   1140
ataataaaga tcattatttg gagtatttag caggtgatct tgattggttt ggtaatggta   1200
gtagaattat tataacaact agagacaagc atttgataga gaagaatgat ataatatatg   1260
aggtgactgc actacccgat catgaatcca ttcaattgtt caaacaacat gctttcggaa   1320
aagaagttcc aaatgagaat tttgagaagc tttcattaga ggtagtaaat tatgctaaag   1380
gccttccttt agccctcaaa gtgtggggtt ctttgctgca taacctacga ttaactgaat   1440
ggaaaagtgc tatagagcac atgaaaaata actcttattc tggaattatt gataagctca   1500
aaataagtta tgatggatta gagcccaaac aacaagagat gtttttagat atagcatgct   1560
tcttgcgagg ggaagaaaaa gattacatcc tacaaatcct tgagagttgt catattggag   1620
ctgaatacgg gttacgtatt ttaattgaca aatctcttgt gttcatctct gaatataatc   1680
aggttcaaat gcatgactta atacaggata tgggtaaata tatagtgaat tttcaaaaag   1740
atcccggaga acgtagcaga ttatggctcg ccaaggaagt cgaagaagtg atgagcaaca   1800
acacagggac catggcaatg gaagcaattt gggtttcttc ttattctagt actctacgct   1860
ttagcaatca ggccgtgaaa aatatgaaaa ggcttagggt atttaacatg gggaggtcgt   1920
cgacacatta tgccatcgat tatctgccca acaacttgcg ttgttttgtt tgcactaact   1980
atccttggga gtcatttcca tctacatttg aactcaaaat gcttgttcac ctccaactcc   2040
gacacaattc tctgcgtcat ttatggacag aaacaaaggt acaatagctt gaattctatt   2100
ttgttgtcat ttatttttct ctctaactat ctttgtcctt taatttggtg ataatgaaca   2160
aatattattg ttttttgtta tgaaacaata aaagaagaag aacaatattg cagagaaaga   2220
gggagatgga attcttattg aattttgggg cgatttacaa tggggtaaga cccctctatt   2280
tacaggggaa aaataactta gcctcaaaat aaagctcttt aaaagataga cattcactct   2340
```

-continued

```
aaatagaatt ctattataac acttttggcg tacttccttt tttggctaga attatgatac   2400
atgtctttaa atgaacagaa gttgcttttg taatttatca ggacttatgt tgaaacttat   2460
gaaaattgtt attgtttatg ttgtctaata ctaaatataa aatacaataa tattttatcg   2520
taattttttta aaaatttgtc aaataatgca aatgaaaaat taaatttttt ggtcctttaa   2580
aaatttgaga atgaaaaagt acgagttata cttcctaaaa gtttgatagt gaataatatg   2640
taaaatttaa agaatgacta atattggact aatactttaa aacaaataac ttaatataca   2700
aattatagcg agacattttc attcgttgta ctgaatgcaa gaaagaaagg aaaaaaaaac   2760
tcatttataa tatagtttgt cttctactat tttaccttat tgcttcaaat ttgtatttta   2820
tcgattttgc tatatcttat gatttttttc acggtcaata ttcttcttac aagaataaat   2880
tttatatacc tcaagtgttt tgtcaatttg ataaataatt tttcttatat gatgaacttg   2940
taaaataata gaattggatt cttttgctaa ttagttaatt caacgactta attatttatt   3000
ctcaacatta aaggaaataa tttagttttt attaattcaa actcttagta tttgctcatt   3060
ctaattttca gtccaataag aattcaattt tcaaatagta agaaaagtca tatattttga   3120
attttatgtt ttccgaagca ttgtttgttt gtttaactct acgggagttt tctaactcac   3180
attttgtata ataaaatttt ttgagtagta gttcagtaca actctaatat taatgggctt   3240
taaataagga aatatatatt acgtaaaaat ttaaatcatt ttaaagttct ttcctaccaa   3300
gtaaataagg gaaaatttaa taacaaaaat ttagttgatt ttaaaatcct aaatattaga   3360
aaattaactt aaaatataat ttcgtctagt gtaaaattta tttttaaagg gtaaaaaaga   3420
cgaacgacat taagagcctt tgtaatttta atatagtata aatataaata atttaccttt   3480
attcagtttc ttaacaagta attttccata tataaaaaat aaatttctat attcacacaa   3540
aaataatgtg ttggccctcg taattcaaat actatcattc atttcttgtc gagggagtag   3600
taaatacttt taggaaagtt agcaataagt aatcaagaaa tcaagaaaac agaggtcatt   3660
tgatgcccac aaatacaaat gaaaaaacaa aacaaatgtt acgaaacaat aaaagaacaa   3720
gaatagcctc aaagtaaaac tctctgatag acatttactc taaatagaat tctatttata   3780
acaatcaaaa agtttctaca tttatagata gctccactag ccaaatattt tattattgga   3840
atcagcaaaa taggttgttt cttttttttat tctcattctg tctgtgttct aaacagcatt   3900
tgccgtctct acggaggata gatctcagct ggtctaaaag attgacgcga acaccagatt   3960
tcacggggat gccaaatttg gagtatgtga atttgtatca atgtagtaat cttgaagaag   4020
ttcaccattc cctgggatgt tgcagcaaag tcattggttt atatttgaat gattgtaaaa   4080
gccttaagag gtttccatgt gttaacgtgg aatctcttga atatctgggt ctaagaagtt   4140
gcgatagttt agagaaattg ccagaaatct acgggagaat gaagccggag atacagattc   4200
acatgcaagg ctctgggata agggaactac catcatctat ttttcagtac aaaactcatg   4260
ttaccaagct attgttgtgg aatatgaaaa accttgtagc tcttccaagc agcatatgta   4320
ggttgaaaag tttggttagt ctgagtgtgt cgggttgctc aaaacttgaa agcttgccag   4380
aagagatagg ggatttagac aacttacggg tgtttgatgc cagtgatact ctaattttac   4440
gacctccgtc ttccatcata cgcttgaaca aacttataat cttgatgttt cgaggcttca   4500
aagatggagt gcactttgag ttccctcctg tggctgaagg attacactca ttggaatatc   4560
tgaatctcag ttactgcaat ctaatagatg gaggacttcc ggaagagatt ggatccttat   4620
cctctttgaa aaagttggat ctcagtagaa ataattttga gcatttgcct tcaagtatag   4680
```

-continued

```
cccaacttgg tgctcttcaa tccttagact taaaagattg ccagaggctt acacagctac   4740

cagaacttcc cccagaatta aatgaattgc atgtagattg tcatatggct ctgaaattta   4800

tccattattt agtaacaaag agaaagaaac tacatagagt gaaacttgat gatgcacaca   4860

atgatactat gtacaatttg tttgcatata ccatgtttca gaatatctct tccatgaggc   4920

atgacatctc tgcttcagat tccttgtcac taacagtatt taccggtcaa ccgtatcctg   4980

aaaagatccc gagttggttc caccatcagg gttgggatag tagtgtatca gtcaatttgc   5040

ctgaaaattg gtatatacct gataaattct tgggatttgc tgtatgttac tctcgtagct   5100

taattgacac aacagctcac ttgattcccg tatgtgatga caagatgtcg cgcatgaccc   5160

agaaacttgc cttatcagaa tgtgatacag aatcatccaa ctattcagaa tgggatatac   5220

atttttttctt tgtacctttt gctggcttat gggatacatc taaggcaaat ggaaaaacac   5280

caaatgatta tgggattatt aggctatctt tttctggaga agagaagatg tatggacttc   5340

gtttgttgta taaagaagga ccagaggtta atgccttgtt acaaatgagg gaaaatagca   5400

atgaaccaac agaacattcc actgggataa ggaggactca atataacaac agaacttcct   5460

tttatgagct catcaatggg tga                                           5483
```

<210> SEQ ID NO 18
<211> LENGTH: 6095
<212> TYPE: DNA
<213> ORGANISM: artificial
<220> FEATURE:
<223> OTHER INFORMATION: cDNA-N/intron construct: E1-E2-I2-E3-I3-E4-E5

<400> SEQUENCE: 18

```
atggcatctt cttcttcttc ttctagatgg agctatgatg ttttcttaag ttttagaggc     60

gaagatactc gaaaaacgtt tacaagtcac ttatacgaag tcttgaatga taagggaata    120

aaaacctttc aagatgataa aaggctagag tacggcgcaa ccatcccagg tgaactctgt    180

aaagctatag aagagtctca atttgccatt gttgttttct cagagaatta tgcaacatca    240

aggtggtgtt tgaatgaact agtgaagatc atggaatgca aaactcgatt taagcaaact    300

gttataccga tattctatga tgtggatcca tcacatgttc ggaaccaaaa ggagagcttt    360

gcaaaagcct ttgaagaaca tgaaacaaag tataaggatg atgttgaggg aatacaaaga    420

tggaggattg ctttaaatga agcggccaat ctcaaaggct cctgtgataa tcgtgacaag    480

actgatgcag actgtattcg acagattgtt gaccaaatct catccaaatt atgcaagatt    540

tctttatctt atttgcaaaa cattgttgga atagatactc atttagagaa aatagaatcc    600

ttactagaga taggaatcaa tggtgttcgg attatgggga tctggggaat gggggggagtc    660

ggtaaaacaa caatagcaag agctatattt gatactcttt taggaagaat ggatagttcc    720

tatcaatttg atggtgcttg tttccttaag gatattaaag aaaacaaacg tggaatgcat    780

tctttgcaaa atgcccttct ctctgaactt ttaagggaaa aagctaatta caataatgag    840

gaggatggaa agcaccaaat ggctagtaga cttcgttcga agaaggtcct aattgtgctt    900

gatgatatag ataataaaga tcattatttg gagtatttag caggtgatct tgattggttt    960

ggtaatggta gtagaattat tataacaact agagacaagc atttgataga gaagaatgat   1020

ataatatatg aggtgactgc actacccgat catgaatcca ttcaattgtt caaacaacat   1080

gctttcggaa aagaagttcc aaatgagaat tttgagaagc tttcattaga ggtagtaaat   1140

tatgctaaag gccttccttt agccctcaaa gtgtggggtt ctttgctgca taacctacga   1200

ttaactgaat ggaaaagtgc tatagagcac atgaaaaata actcttattc tggaattatt   1260
```

-continued

```
gataagctca aaataagtta tgatggatta gagcccaaac aacaagagat gtttttagat   1320
atagcatgct tcttgcgagg ggaagaaaaa gattacatcc tacaaatcct tgagagttgt   1380
catattggag ctgaatacgg gttacgtatt ttaattgaca aatctcttgt gttcatctct   1440
gaatataatc aggttcaaat gcatgactta atacaggata tgggtaaata tatagtgaat   1500
tttcaaaaag atcccggaga acgtagcaga ttatggctcg ccaaggaagt cgaagaagtg   1560
atgagcaaca acacagtaag taagctaaat aatgcaataa tatttaattt ctaattttat   1620
attctaaaga cacatagggc agtcaattcc agttatttgt tcctcttgct tcatagtctt   1680
gacggtacat cattttagtt gtttacttta gttagtagga gatataaaag taatattaat   1740
tacctcatta gtaaaaaaaa acattaattg cctaatttgt ttagtagccg ctttaattta   1800
cgttccctaa ttcgtttttt cttatatttt ttagggatgg attagtctag tagccactta   1860
atctgtttga tccaatgtct ttctttggat taacttgaaa attttatgac attatatata   1920
ataactcaat cattcattca ctttaccatt attatttttt atataaagtt acaatttatt   1980
ggtactgttt cagttacaat tactttccaa catggaaaac ttataaactg gactccaata   2040
aacttataag aaaaatgtaa taatagaaaa taaaattata taattaatta caaaaaagta   2100
tttttctgaa gtaacatcag tatttcttaa aaagaatcca attaacattg tatcttaaac   2160
tttggtattg taaggcgtga gaaagtagtg gccttatttc aatttgacgt gaagaataga   2220
atgcctttta acgacataag ggaagggggc aagaataagt ttctattcag ccgggctcga   2280
agcagaaggt agaacgtaat atcttttgtt ggttcagctc atcaagctat tacaaaagag   2340
tccgctcata ttaacaaacg gagtttatac gacatttgaa attatacttt gtagactaat   2400
gatcttcttg ttaccagggg accatggcaa tggaagcaat ttgggtttct tcttattcta   2460
gtactctacg ctttagcaat caggccgtga aaaatatgaa aaggcttagg gtatttaaca   2520
tggggaggtc gtcgacacat tatgccatcg attatctgcc caacaacttg cgttgttttg   2580
tttgcactaa ctatccttgg gagtcatttc catctacatt tgaactcaaa atgcttgttc   2640
acctccaact ccgacacaat tctctgcgtc atttatggac agaaacaaag gtacaatagc   2700
ttgaattcta ttttgttgtc atttattttt ctctctaact atctttgtcc tttaatttgg   2760
tgataatgaa caaatattat tgttttttgt tatgaaacaa taaaagaaga agaacaatat   2820
tgcagagaaa gagggagatg gaattcttat tgaattttgg ggcgatttac aatggggtaa   2880
gacccctcta tttacagggg aaaaataact tagcctcaaa ataaagctct ttaaaagata   2940
gacattcact ctaaatagaa ttctattata acacttttgg cgtacttcct tttttggcta   3000
gaattatgat acatgtcttt aaatgaacag aagttgcttt tgtaatttat caggacttat   3060
gttgaaactt atgaaaattg ttattgttta tgttgtctaa tactaaatat aaaatacaat   3120
aatattttat cgtaattttt taaaaatttg tcaaataatg caaatgaaaa attaaatttt   3180
ttggtccttt aaaaatttga gaatgaaaaa gtacgagtta tacttcctaa aagtttgata   3240
gtgaataata tgtaaaattt aaagaatgac taatattgga ctaatacttt aaaacaaata   3300
acttaatata caaattatag cgagacattt tcattcgttg tactgaatgc aagaaagaaa   3360
ggaaaaaaaa actcatttat aatatagttt gtcttctact attttacctt attgcttcaa   3420
atttgtattt tatcgatttt gctatatctt atgatttttt tcacggtcaa tattcttctt   3480
acaagaataa attttatata cctcaagtgt tttgtcaatt tgataaataa tttttcttat   3540
atgatgaact tgtaaaataa tagaattgga ttcttttgct aattagttaa ttcaacgact   3600
```

-continued

```
taattattta ttctcaacat taaaggaaat aatttagttt ttattaattc aaactcttag   3660
tatttgctca ttctaatttt cagtccaata agaattcaat tttcaaatag taagaaaagt   3720
catatatttt gaattttatg ttttccgaag cattgtttgt ttgtttaact ctacgggagt   3780
tttctaactc acattttgta taataaaatt ttttgagtag tagttcagta caactctaat   3840
attaatgggc tttaaataag gaaatatata ttacgtaaaa atttaaatca ttttaaagtt   3900
ctttcctacc aagtaaataa gggaaaattt aataacaaaa atttagttga ttttaaaatc   3960
ctaaatatta gaaaattaac ttaaaatata atttcgtcta gtgtaaaatt tatttttaaa   4020
gggtaaaaaa gacgaacgac attaagagcc tttgtaattt taatatagta taaatataaa   4080
taatttacct ttattcagtt tcttaacaag taattttcca tatataaaaa ataaatttct   4140
atattcacac aaaaataatg tgttggccct cgtaattcaa atactatcat tcatttcttg   4200
tcgagggagt agtaaatact tttaggaaag ttagcaataa gtaatcaaga aatcaagaaa   4260
acagaggtca tttgatgccc acaaatacaa atgaaaaaac aaaacaaatg ttacgaaaca   4320
ataaaagaac aagaatagcc tcaaagtaaa actctctgat agacatttac tctaaataga   4380
attctattta taacaatcaa aaagtttcta catttataga tagctccact agccaaatat   4440
tttattattg gaatcagcaa aataggttgt ttcttttttt attctcattc tgtctgtgtt   4500
ctaaacagca tttgccgtct ctacggagga tagatctcag ctggtctaaa agattgacgc   4560
gaacaccaga tttcacgggg atgccaaatt tggagtatgt gaatttgtat caatgtagta   4620
atcttgaaga agttcaccat tccctgggat gttgcagcaa agtcattggt ttatatttga   4680
atgattgtaa aagccttaag aggtttccat gtgttaacgt ggaatctctt gaatatctgg   4740
gtctaagaag ttgcgatagt ttagagaaat tgccagaaat ctacgggaga atgaagccgg   4800
agatacagat tcacatgcaa ggctctggga taagggaact accatcatct atttttcagt   4860
acaaaactca tgttaccaag ctattgttgt ggaatatgaa aaaccttgta gctcttccaa   4920
gcagcatatg taggttgaaa agtttggtta gtctgagtgt gtcgggttgc tcaaaacttg   4980
aaagcttgcc agaagagata ggggatttag acaacttacg ggtgtttgat gccagtgata   5040
ctctaatttt acgacctccg tcttccatca tacgcttgaa caaacttata atcttgatgt   5100
ttcgaggctt caaagatgga gtgcactttg agttccctcc tgtggctgaa ggattacact   5160
cattggaata tctgaatctc agttactgca atctaataga tggaggactt ccggaagaga   5220
ttggatcctt atcctctttg aaaaagttgg atctcagtag aaataatttt gagcatttgc   5280
cttcaagtat agcccaactt ggtgctcttc aatccttaga cttaaaagat tgccagaggc   5340
ttacacagct accagaactt cccccagaat taaatgaatt gcatgtagat tgtcatatgg   5400
ctctgaaatt tatccattat ttagtaacaa agagaaagaa actacataga gtgaaacttg   5460
atgatgcaca caatgatact atgtacaatt tgtttgcata taccatgttt cagaatatct   5520
cttccatgag gcatgacatc tctgcttcag attccttgtc actaacagta tttaccggtc   5580
aaccgtatcc tgaaaagatc ccgagttggt tccaccatca gggttgggat agtagtgtat   5640
cagtcaattt gcctgaaaat tggtatatac ctgataaatt cttgggattt gctgtatgtt   5700
actctcgtag cttaattgac acaacagctc acttgattcc cgtatgtgat gacaagatgt   5760
cgcgcatgac ccagaaactt gccttatcag aatgtgatac agaatcatcc aactattcag   5820
aatgggatat acattttttc tttgtacctt ttgctggctt atgggataca tctaaggcaa   5880
atggaaaaac accaaatgat tatgggatta ttaggctatc tttttctgga gaagagaaga   5940
tgtatggact tcgtttgttg tataaagaag gaccagaggt taatgccttg ttacaaatga   6000
```

gggaaaatag caatgaacca acagaacatt ccactgggat aaggaggact caatataaca 6060
acagaacttc cttttatgag ctcatcaatg ggtga 6095

<210> SEQ ID NO 19
<211> LENGTH: 5586
<212> TYPE: DNA
<213> ORGANISM: artificial
<220> FEATURE:
<223> OTHER INFORMATION: cDNA-N/intron construct: E1-E2-E3-I3-E4-I4-E5

<400> SEQUENCE: 19
atggcatctt cttcttcttc ttctagatgg agctatgatg ttttcttaag ttttagaggc 60
gaagatactc gaaaaacgtt tacaagtcac ttatacgaag tcttgaatga taagggaata 120
aaaacctttc aagatgataa aaggctagag tacggcgcaa ccatcccagg tgaactctgt 180
aaagctatag aagagtctca atttgccatt gttgttttct cagagaatta tgcaacatca 240
aggtggtgtt tgaatgaact agtgaagatc atggaatgca aaactcgatt taagcaaact 300
gttataccga tattctatga tgtggatcca tcacatgttc ggaaccaaaa ggagagcttt 360
gcaaaagcct ttgaagaaca tgaaacaaag tataaggatg atgttgaggg aatacaaaga 420
tggaggattg ctttaaatga agcggccaat ctcaaaggct cctgtgataa tcgtgacaag 480
actgatgcag actgtattcg acagattgtt gaccaaatct catccaaatt atgcaagatt 540
tctttatctt atttgcaaaa cattgttgga atagatactc atttagagaa aatagaatcc 600
ttactagaga taggaatcaa tggtgttcgg attatgggga tctggggaat gggggggagtc 660 ggtaaaacaa caatagcaag agctatattt gatactcttt taggaagaat ggatagttcc 720
tatcaatttg atggtgcttg tttccttaag gatattaaag aaaacaaacg tggaatgcat 780
tctttgcaaa atgcccttct ctctgaactt ttaagggaaa aagctaatta caataatgag 840
gaggatggaa agcaccaaat ggctagtaga cttcgttcga agaaggtcct aattgtgctt 900
gatgatatag ataataaaga tcattatttg gagtatttag caggtgatct tgattggttt 960
ggtaatggta gtagaattat tataacaact agagacaagc atttgataga gaagaatgat 1020
ataatatatg aggtgactgc actacccgat catgaatcca ttcaattgtt caaacaacat 1080
gctttcggaa aagaagttcc aaatgagaat tttgagaagc tttcattaga ggtagtaaat 1140
tatgctaaag gccttccttt agccctcaaa gtgtggggtt ctttgctgca taacctacga 1200
ttaactgaat ggaaaagtgc tatagagcac atgaaaaata actcttattc tggaattatt 1260
gataagctca aaataagtta tgatggatta gagcccaaac aacaagagat gtttttagat 1320
atagcatgct tcttgcgagg ggaagaaaaa gattacatcc tacaaatcct tgagagttgt 1380
catattggag ctgaatacgg gttacgtatt ttaattgaca aatctcttgt gttcatctct 1440
gaatataatc aggttcaaat gcatgactta atacaggata tgggtaaata tatagtgaat 1500
tttcaaaaag atcccggaga acgtagcaga ttatggctcg ccaaggaagt cgaagaagtg 1560
atgagcaaca acacagggac catggcaatg gaagcaattt gggtttcttc ttattctagt 1620
actctacgct ttagcaatca ggccgtgaaa aatatgaaaa ggcttagggt atttaacatg 1680
gggaggtcgt cgacacatta tgccatcgat tatctgccca acaacttgcg ttgttttgtt 1740
tgcactaact atccttggga gtcatttcca tctacatttg aactcaaaat gcttgttcac 1800
ctccaactcc gacacaattc tctgcgtcat ttatggacag aaacaaaggt acaatagctt 1860
gaattctatt ttgttgtcat ttatttttct ctctaactat ctttgtcctt taatttggtg 1920

-continued

```
ataatgaaca aatattattg ttttttgtta tgaaacaata aaagaagaag aacaatattg   1980
cagagaaaga gggagatgga attcttattg aattttgggg cgatttacaa tggggtaaga   2040
cccctctatt tacaggggaa aaataactta gcctcaaaat aaagctcttt aaaagataga   2100
cattcactct aaatagaatt ctattataac acttttggcg tacttccttt tttggctaga   2160
attatgatac atgtctttaa atgaacagaa gttgcttttg taatttatca ggacttatgt   2220
tgaaacttat gaaaattgtt attgtttatg ttgtctaata ctaaatataa aatacaataa   2280
tattttatcg taattttta aaaatttgtc aaataatgca aatgaaaaat taaattttt   2340
ggtcctttaa aaatttgaga atgaaaaagt acgagttata cttcctaaaa gtttgatagt   2400
gaataatatg taaaatttaa agaatgacta atattggact aatactttaa aacaaataac   2460
ttaatataca aattatagcg agacattttc attcgttgta ctgaatgcaa gaaagaaagg   2520
aaaaaaaaac tcatttataa tatagtttgt cttctactat tttaccttat tgcttcaaat   2580
ttgtatttta tcgattttgc tatatcttat gattttttc acggtcaata ttcttcttac   2640
aagaataaat tttatatacc tcaagtgttt tgtcaatttg ataaataatt tttcttatat   2700
gatgaacttg taaaataata gaattggatt cttttgctaa ttagttaatt caacgactta   2760
attatttatt ctcaacatta aaggaaataa tttagttttt attaattcaa actcttagta   2820
tttgctcatt ctaattttca gtccaataag aattcaattt tcaaatagta agaaaagtca   2880
tatattttga attttatgtt ttccgaagca ttgtttgttt gtttaactct acgggagttt   2940
tctaactcac attttgtata ataaaatttt ttgagtagta gttcagtaca actctaatat   3000
taatgggctt taaataagga aatatatatt acgtaaaaat ttaaatcatt ttaaagttct   3060
ttcctaccaa gtaaataagg gaaaatttaa taacaaaaat ttagttgatt ttaaaatcct   3120
aaatattaga aaattaactt aaaatataat ttcgtctagt gtaaaattta tttttaaagg   3180
gtaaaaaaga cgaacgacat taagagcctt tgtaatttta atatagtata aatataaata   3240
atttaccttt attcagtttc ttaacaagta attttccata tataaaaaat aaatttctat   3300
attcacacaa aaataatgtg ttggccctcg taattcaaat actatcattc atttcttgtc   3360
gagggagtag taaatacttt taggaaagtt agcaataagt aatcaagaaa tcaagaaaac   3420
agaggtcatt tgatgcccac aaatacaaat gaaaaaacaa aacaaatgtt acgaaacaat   3480
aaaagaacaa gaatagcctc aaagtaaaac tctctgatag acatttactc taaatagaat   3540
tctatttata acaatcaaaa agtttctaca tttatagata gctccactag ccaaatattt   3600
tattattgga atcagcaaaa taggttgttt cttttttat tctcattctg tctgtgttct   3660
aaacagcatt tgccgtctct acggaggata gatctcagct ggtctaaaag attgacgcga   3720
acaccagatt tcacggggat gccaaatttg gagtatgtga atttgtatca atgtagtaat   3780
cttgaagaag ttcaccattc cctgggatgt tgcagcaaag tcattggttt atatttgaat   3840
gattgtaaaa gccttaagag gtttccatgt gttaacgtgg aatctcttga atatctgggt   3900
ctaagaagtt gcgatagttt agagaaattg ccagaaatct acgggagaat gaagccggag   3960
atacagattc acatgcaagg ctctgggata agggaactac catcatctat tttcagtac   4020
aaaactcatg ttaccaagct attgttgtgg aatatgaaaa accttgtagc tcttccaagc   4080
agcatatgta ggttgaaaag tttggttagt ctgagtgtgt cgggttgctc aaaacttgaa   4140
agcttgccag aagagatagg ggatttagac aacttacggg tgtttgatgc cagtgatact   4200
ctaattttac gacctccgtc ttccatcata cgcttgaaca aacttataat cttgatgttt   4260
cgaggcttca aagatggagt gcactttgag ttccctcctg tggctgaagg attacactca   4320
```

```
ttggaatatc tgaatctcag ttactgcaat ctaatagatg gaggacttcc ggaagagatt   4380

ggatccttat cctctttgaa aaagttggat ctcagtagaa ataattttga gcatttgcct   4440

tcaagtatag cccaacttgg tgctcttcaa tccttagact taaaagattg ccagaggctt   4500

acacagctac cagaacttcc cccagaatta aatgaattgc atgtagattg tcatatggct   4560

ctgaaattta tccattattt agtaacaaag agaaagaaac tacatagagt gaaacttgat   4620

gatgcacaca atgatactat gtacaatttg tttgcatata ccatgtttca gaatatctct   4680

tccatgaggc atgacatctc tgcttcagat tccttgtcac taacagtatt taccggtcaa   4740

ccgtatcctg aaaagatccc gagttggttc caccatcagg gttgggatag tagtgtatca   4800

gtcaatttgc ctgaaaattg gtatatacct gataaattct tgggatttgc tgtatgttac   4860

tctcgtagct taattgacac aacagctcac ttgattcccg tatgtgatga caagatgtcg   4920

cgcatgaccc agaaacttgc cttatcagaa tgtgatacag aatcatccaa ctattcagaa   4980

tgggatatac atttttcttt tgtacctttt gctggcttat gggatacatc taaggcaaat   5040

ggaaaaacac caaatgatta tgggattatt aggctatctt tttctggaga agagaagatg   5100

tatggacttc gtttgttgta taaagaagga ccagaggtta atgccttgtt acaaatgagg   5160

gaaaatagca atgaaccaac agaacattcc actgggataa ggaggactca atataacaac   5220

agaacttcct tttatgtaag tctctacttc tattagctac aaagtcttct tccaaaatca   5280

atactccatc cgttccagtt tatgtgaacc tatttttttgt tcgtccattc taaaaagaat   5340

gacccctttc taaatttgga aataattttg gttaaactta taattctacc attaacgaga   5400

agcttttata accacacaaa tattctgggg ccctttttga attgtttagg accataaatt   5460

ccaaaagtcc tcattttttc ttaaactccg tgcccaatca aacaagttca cgtaaattgg   5520

aacggaggga atatattttt tcttctcatt cttttcccct atttacagga gctcatcaat   5580

gggtga                                                              5586
```

<210> SEQ ID NO 20
<211> LENGTH: 6325
<212> TYPE: DNA
<213> ORGANISM: Artificial
<220> FEATURE:
<223> OTHER INFORMATION: cDNA-N/intron construct: E1-I1-E2-I2-E3-I3-E4-E5

<400> SEQUENCE: 20

```
atggcatctt cttcttcttc ttctagatgg agctatgatg ttttcttaag ttttagaggc     60

gaagatactc gaaaaacgtt tacaagtcac ttatacgaag tcttgaatga taagggaata    120

aaaacctttc aagatgataa aaggctagag tacggcgcaa ccatcccagg tgaactctgt    180

aaagctatag aagagtctca atttgccatt gttgttttct cagagaatta tgcaacatca    240

aggtggtgtt tgaatgaact agtgaagatc atggaatgca aaactcgatt taagcaaact    300

gttataccga tattctatga tgtggatcca tcacatgttc ggaaccaaaa ggagagcttt    360

gcaaaagcct ttgaagaaca tgaaacaaag tataaggatg atgttgaggg aatacaaaga    420

tggaggattg ctttaaatga agcggccaat ctcaaaggct cctgtgataa tcgtgacaag    480

tgagttaaaa acatataagc tgaatacttt gcattcaaat gagttaaaca taatcttaaa    540

taaatttttc aatttttttgg aataaattga tagttgatta tatatgtttc tatcagttaa    600

ttacaaactc aataacatta ttacgtagat aaaattttta ttagttcttc aaagagtttg    660

atttatgtgc acactctttg tatatatcac aatcttttta cttttgtagg actgatgcag    720
```

-continued

```
actgtattcg acagattgtt gaccaaatct catccaaatt atgcaagatt tctttatctt    780
atttgcaaaa cattgttgga atagatactc atttagagaa aatagaatcc ttactagaga    840
taggaatcaa tggtgttcgg attatgggga tctggggaat gggggagtc ggtaaaacaa    900
caatagcaag agctatattt gatactcttt taggaagaat ggatagttcc tatcaatttg    960
atggtgcttg tttccttaag gatattaaag aaaacaaacg tggaatgcat tctttgcaaa   1020
atgcccttct ctctgaactt ttaagggaaa aagctaatta caataatgag gaggatggaa   1080
agcaccaaat ggctagtaga cttcgttcga agaaggtcct aattgtgctt gatgatatag   1140
ataataaaga tcattatttg gagtatttag caggtgatct tgattggttt ggtaatggta   1200
gtagaattat tataacaact agagacaagc atttgataga gaagaatgat ataatatatg   1260
aggtgactgc actacccgat catgaatcca ttcaattgtt caaacaacat gctttcggaa   1320
aagaagttcc aaatgagaat tttgagaagc tttcattaga ggtagtaaat tatgctaaag   1380
gccttccttt agccctcaaa gtgtggggtt ctttgctgca taacctacga ttaactgaat   1440
ggaaaagtgc tatagagcac atgaaaaata actcttattc tggaattatt gataagctca   1500
aaataagtta tgatggatta gagcccaaac aacaagagat gtttttagat atagcatgct   1560
tcttgcgagg ggaagaaaaa gattacatcc tacaaatcct tgagagttgt catattggag   1620
ctgaatacgg gttacgtatt ttaattgaca aatctcttgt gttcatctct gaatataatc   1680
aggttcaaat gcatgactta atacaggata tgggtaaata tatagtgaat tttcaaaaag   1740
atcccggaga acgtagcaga ttatggctcg ccaaggaagt cgaagaagtg atgagcaaca   1800
acacagtaag taagctaaat aatgcaataa tatttaattt ctaattttat attctaaaga   1860
cacatagggc agtcaattcc agttatttgt tcctcttgct tcatagtctt gacggtacat   1920
cattttagtt gtttacttta gttagtagga gatataaaag taatattaat tacctcatta   1980
gtaaaaaaaa acattaattg cctaatttgt ttagtagccg ctttaattta cgttccctaa   2040
ttcgtttttt cttatatttt ttagggatgg attagtctag tagccactta atctgtttga   2100
tccaatgtct ttctttggat taacttgaaa attttatgac attatatata ataactcaat   2160
cattcattca ctttaccatt attatttttt atataaagtt acaatttatt ggtactgttt   2220
cagttacaat tactttccaa catggaaaac ttataaactg gactccaata aacttataag   2280
aaaaatgtaa taatagaaaa taaaattata taattaatta caaaaaagta tttttctgaa   2340
gtaacatcag tatttcttaa aaagaatcca attaacattg tatcttaaac tttggtattg   2400
taaggcgtga gaaagtagtg gccttatttc aatttgacgt gaagaataga atgcctttta   2460
acgacataag ggaagggggc aagaataagt ttctattcag ccgggctcga agcagaaggt   2520
agaacgtaat atcttttgtt ggttcagctc atcaagctat tacaaaagag tccgctcata   2580
ttaacaaacg gagtttatac gacatttgaa attatacttt gtagactaat gatcttcttg   2640
ttaccagggg accatggcaa tggaagcaat ttgggtttct tcttattcta gtactctacg   2700
ctttagcaat caggccgtga aaaatatgaa aaggcttagg gtatttaaca tggggaggtc   2760
gtcgacacat tatgccatcg attatctgcc caacaacttg cgttgttttg tttgcactaa   2820
ctatccttgg gagtcatttc catctacatt tgaactcaaa atgcttgttc acctccaact   2880
ccgacacaat tctctgcgtc atttatggac agaaacaaag gtacaatagc ttgaattcta   2940
ttttgttgtc atttattttt ctctctaact atctttgtcc tttaatttgg tgataatgaa   3000
caaatattat tgttttttgt tatgaaacaa taaaagaaga agaacaatat tgcagagaaa   3060
gagggagatg gaattcttat tgaattttgg ggcgatttac aatggggtaa gacccctcta   3120
```

-continued

```
tttacagggg aaaaataact tagcctcaaa ataaagctct ttaaaagata gacattcact   3180
ctaaatagaa ttctattata acacttttgg cgtacttcct tttttggcta gaattatgat   3240
acatgtcttt aaatgaacag aagttgcttt tgtaatttat caggacttat gttgaaactt   3300
atgaaaattg ttattgttta tgttgtctaa tactaaatat aaaatacaat aatattttat   3360
cgtaattttt taaaaatttg tcaaataatg caaatgaaaa attaaatttt ttggtccttt   3420
aaaaatttga gaatgaaaaa gtacgagtta tacttcctaa aagtttgata gtgaataata   3480
tgtaaaattt aaagaatgac taatattgga ctaatacttt aaaacaaata acttaatata   3540
caaattatag cgagacattt tcattcgttg tactgaatgc aagaaagaaa ggaaaaaaaa   3600
actcatttat aatatagttt gtcttctact attttacctt attgcttcaa atttgtattt   3660
tatcgatttt gctatatctt atgatttttt tcacggtcaa tattcttctt acaagaataa   3720
attttatata cctcaagtgt tttgtcaatt tgataaataa tttttcttat atgatgaact   3780
tgtaaaataa tagaattgga ttcttttgct aattagttaa ttcaacgact taattattta   3840
ttctcaacat taaaggaaat aatttagttt ttattaattc aaactcttag tatttgctca   3900
ttctaatttt cagtccaata agaattcaat tttcaaatag taagaaaagt catatatttt   3960
gaattttatg ttttccgaag cattgtttgt ttgtttaact ctacgggagt tttctaactc   4020
acattttgta taataaaatt ttttgagtag tagttcagta caactctaat attaatgggc   4080
tttaaataag gaaatatata ttacgtaaaa atttaaatca ttttaaagtt ctttcctacc   4140
aagtaaataa gggaaaattt aataacaaaa atttagttga ttttaaaatc ctaaatatta   4200
gaaaattaac ttaaaatata atttcgtcta gtgtaaaatt tatttttaaa gggtaaaaaa   4260
gacgaacgac attaagagcc tttgtaattt taatatagta taaatataaa taatttacct   4320
ttattcagtt tcttaacaag taattttcca tatataaaaa ataaatttct atattcacac   4380
aaaaataatg tgttggccct cgtaattcaa atactatcat tcatttcttg tcgagggagt   4440
agtaaatact tttaggaaag ttagcaataa gtaatcaaga aatcaagaaa acagaggtca   4500
tttgatgccc acaaatacaa atgaaaaaac aaaacaaatg ttacgaaaca ataaaagaac   4560
aagaatagcc tcaaagtaaa actctctgat agacatttac tctaaataga attctattta   4620
taacaatcaa aaagtttcta catttataga tagctccact agccaaatat tttattattg   4680
gaatcagcaa aataggttgt ttcttttttt attctcattc tgtctgtgtt ctaaacagca   4740
tttgccgtct ctacggagga tagatctcag ctggtctaaa agattgacgc gaacaccaga   4800
tttcacgggg atgccaaatt tggagtatgt gaatttgtat caatgtagta atcttgaaga   4860
agttcaccat tccctgggat gttgcagcaa agtcattggt ttatatttga atgattgtaa   4920
aagccttaag aggtttccat gtgttaacgt ggaatctctt gaatatctgg gtctaagaag   4980
ttgcgatagt ttagagaaat tgccagaaat ctacgggaga atgaagccgg agatacagat   5040
tcacatgcaa ggctctggga taagggaact accatcatct atttttcagt acaaaactca   5100
tgttaccaag ctattgttgt ggaatatgaa aaaccttgta gctcttccaa gcagcatatg   5160
taggttgaaa agtttggtta gtctgagtgt gtcgggttgc tcaaaacttg aaagcttgcc   5220
agaagagata ggggatttag acaacttacg ggtgtttgat gccagtgata ctctaatttt   5280
acgacctccg tcttccatca tacgcttgaa caaacttata atcttgatgt ttcgaggctt   5340
caaagatgga gtgcactttg agttccctcc tgtggctgaa ggattacact cattggaata   5400
tctgaatctc agttactgca atctaataga tggaggactt ccggaagaga ttggatcctt   5460
```

-continued

```
atcctctttg aaaaagttgg atctcagtag aaataatttt gagcatttgc cttcaagtat   5520

agcccaactt ggtgctcttc aatccttaga cttaaaagat tgccagaggc ttacacagct   5580

accagaactt cccccagaat taaatgaatt gcatgtagat tgtcatatgg ctctgaaatt   5640

tatccattat ttagtaacaa agagaaagaa actacataga gtgaaacttg atgatgcaca   5700

caatgatact atgtacaatt tgtttgcata taccatgttt cagaatatct cttccatgag   5760

gcatgacatc tctgcttcag attccttgtc actaacagta tttaccggtc aaccgtatcc   5820

tgaaaagatc ccgagttggt tccaccatca gggttgggat agtagtgtat cagtcaattt   5880

gcctgaaaat tggtatatac ctgataaatt cttgggattt gctgtatgtt actctcgtag   5940

cttaattgac acaacagctc acttgattcc cgtatgtgat gacaagatgt cgcgcatgac   6000

ccagaaactt gccttatcag aatgtgatac agaatcatcc aactattcag aatgggatat   6060

acatttttc tttgtacctt ttgctggctt atgggataca tctaaggcaa atggaaaaac   6120

accaaatgat tatgggatta ttaggctatc tttttctgga gaagagaaga tgtatggact   6180

tcgtttgttg tataaagaag gaccagaggt taatgccttg ttacaaatga gggaaaatag   6240

caatgaacca acagaacatt ccactgggat aaggaggact caatataaca acagaacttc   6300

cttttatgag ctcatcaatg ggtga                                         6325
```

<210> SEQ ID NO 21
<211> LENGTH: 5816
<212> TYPE: DNA
<213> ORGANISM: artificial
<220> FEATURE:
<223> OTHER INFORMATION: cDNA-N/intron construct: E1-I1-E2-E3-I3-E4-
I4-E5

<400> SEQUENCE: 21

```
atggcatctt cttcttcttc ttctagatgg agctatgatg ttttcttaag ttttagaggc     60

gaagatactc gaaaaacgtt tacaagtcac ttatacgaag tcttgaatga taagggaata    120

aaaacctttc aagatgataa aaggctagag tacggcgcaa ccatcccagg tgaactctgt    180

aaagctatag aagagtctca atttgccatt gttgttttct cagagaatta tgcaacatca    240

aggtggtgtt tgaatgaact agtgaagatc atggaatgca aaactcgatt taagcaaact    300

gttataccga tattctatga tgtggatcca tcacatgttc ggaaccaaaa ggagagcttt    360

gcaaaagcct ttgaagaaca tgaaacaaag tataaggatg atgttgaggg aatacaaaga    420

tggaggattg ctttaaatga agcggccaat ctcaaaggct cctgtgataa tcgtgacaag    480

tgagttaaaa acatataagc tgaatacttt gcattcaaat gagttaaaca taatcttaaa    540

taaatttttc aattttttgg aataaattga tagttgatta tatatgtttc tatcagttaa    600

ttacaaactc aataacatta ttacgtagat aaaattttta ttagttcttc aaagagtttg    660

atttatgtgc acactctttg tatatatcac aatcttttta cttttgtagg actgatgcag    720

actgtattcg acagattgtt gaccaaatct catccaaatt atgcaagatt tctttatctt    780

atttgcaaaa cattgttgga atagatactc atttagagaa aatagaatcc ttactagaga    840

taggaatcaa tggtgttcgg attatgggga tctggggaat ggggggagtc ggtaaaacaa    900

caatagcaag agctatattt gatactcttt taggaagaat ggatagttcc tatcaatttg    960

atggtgcttg tttccttaag gatattaaag aaaacaaacg tggaatgcat tctttgcaaa   1020

atgcccttct ctctgaactt ttaagggaaa aagctaatta caataatgag gaggatggaa   1080

agcaccaaat ggctagtaga cttcgttcga agaaggtcct aattgtgctt gatgatatag   1140
```

-continued

```
ataataaaga tcattatttg gagtatttag caggtgatct tgattggttt ggtaatggta   1200
gtagaattat tataacaact agagacaagc atttgataga gaagaatgat ataatatatg   1260
aggtgactgc actacccgat catgaatcca ttcaattgtt caaacaacat gctttcggaa   1320
aagaagttcc aaatgagaat tttgagaagc tttcattaga ggtagtaaat tatgctaaag   1380
gccttccttt agccctcaaa gtgtggggtt ctttgctgca taacctacga ttaactgaat   1440
ggaaaagtgc tatagagcac atgaaaaata actcttattc tggaattatt gataagctca   1500
aaataagtta tgatggatta gagcccaaac aacaagagat gtttttagat atagcatgct   1560
tcttgcgagg ggaagaaaaa gattacatcc tacaaatcct tgagagttgt catattggag   1620
ctgaatacgg gttacgtatt ttaattgaca aatctcttgt gttcatctct gaatataatc   1680
aggttcaaat gcatgactta atacaggata tgggtaaata tatagtgaat tttcaaaaag   1740
atcccggaga acgtagcaga ttatggctcg ccaaggaagt cgaagaagtg atgagcaaca   1800
acacagggac catggcaatg gaagcaattt gggtttcttc ttattctagt actctacgct   1860
ttagcaatca ggccgtgaaa aatatgaaaa ggcttagggt atttaacatg ggaggtcgt    1920
cgacacatta tgccatcgat tatctgccca acaacttgcg ttgttttgtt tgcactaact   1980
atccttggga gtcatttcca tctacatttg aactcaaaat gcttgttcac ctccaactcc   2040
gacacaattc tctgcgtcat ttatggacag aaacaaaggt acaatagctt gaattctatt   2100
ttgttgtcat ttatttttct ctctaactat ctttgtcctt taatttggtg ataatgaaca   2160
aatattattg ttttttgtta tgaaacaata aaagaagaag aacaatattg cagagaaaga   2220
gggagatgga attcttattg aattttgggg cgatttacaa tggggtaaga cccctctatt   2280
tacaggggaa aaataactta gcctcaaaat aaagctcttt aaaagataga cattcactct   2340
aaatagaatt ctattataac acttttggcg tacttccttt tttggctaga attatgatac   2400
atgtctttaa atgaacagaa gttgcttttg taatttatca ggacttatgt tgaaacttat   2460
gaaaattgtt attgtttatg ttgtctaata ctaaatataa aatacaataa tattttatcg   2520
taattttta aaaatttgtc aaataatgca aatgaaaaat taaatttttt ggtcctttaa    2580
aaatttgaga atgaaaaagt acgagttata cttcctaaaa gtttgatagt gaataatatg   2640
taaaatttaa agaatgacta atattggact aatactttaa aacaaataac ttaatataca   2700
aattatagcg agacattttc attcgttgta ctgaatgcaa gaaagaaagg aaaaaaaaac   2760
tcatttataa tatagtttgt cttctactat tttaccttat tgcttcaaat ttgtatttta   2820
tcgattttgc tatatcttat gatttttttc acggtcaata ttcttcttac aagaataaat   2880
tttatatacc tcaagtgttt tgtcaatttg ataaataatt tttcttatat gatgaacttg   2940
taaaataata gaattggatt cttttgctaa ttagttaatt caacgactta attatttatt   3000
ctcaacatta aaggaaataa tttagttttt attaattcaa actcttagta tttgctcatt   3060
ctaattttca gtccaataag aattcaattt tcaaatagta agaaaagtca tatattttga   3120
attttatgtt ttccgaagca ttgtttgttt gtttaactct acgggagttt tctaactcac   3180
attttgtata ataaaatttt ttgagtagta gttcagtaca actctaatat taatgggctt   3240
taaataagga aatatatatt acgtaaaaat ttaaatcatt ttaaagttct ttcctaccaa   3300
gtaaataagg gaaaatttaa taacaaaaat ttagttgatt ttaaaatcct aaatattaga   3360
aaattaactt aaaatataat ttcgtctagt gtaaaattta tttttaaagg gtaaaaaaga   3420
cgaacgacat taagagcctt tgtaatttta atatagtata aatataaata atttaccttt   3480
attcagtttc ttaacaagta attttccata tataaaaaat aaatttctat attcacacaa   3540
```

```
aaataatgtg ttggccctcg taattcaaat actatcattc atttcttgtc gagggagtag   3600
taaatacttt taggaaagtt agcaataagt aatcaagaaa tcaagaaaac agaggtcatt   3660
tgatgcccac aaatacaaat gaaaaaacaa aacaaatgtt acgaaacaat aaaagaacaa   3720
gaatagcctc aaagtaaaac tctctgatag acatttactc taaatagaat tctatttata   3780
acaatcaaaa agtttctaca tttatagata gctccactag ccaaatattt tattattgga   3840
atcagcaaaa taggttgttt cttttttat tctcattctg tctgtgttct aaacagcatt   3900
tgccgtctct acggaggata gatctcagct ggtctaaaag attgacgcga acaccagatt   3960
tcacggggat gccaaatttg gagtatgtga atttgtatca atgtagtaat cttgaagaag   4020
ttcaccattc cctgggatgt tgcagcaaag tcattggttt atatttgaat gattgtaaaa   4080
gccttaagag gtttccatgt gttaacgtgg aatctcttga atatctgggt ctaagaagtt   4140
gcgatagttt agagaaattg ccagaaatct acgggagaat gaagccggag atacagattc   4200
acatgcaagg ctctgggata agggaactac catcatctat tttcagtac aaaactcatg   4260
ttaccaagct attgttgtgg aatatgaaaa accttgtagc tcttccaagc agcatatgta   4320
ggttgaaaag tttggttagt ctgagtgtgt cgggttgctc aaaacttgaa agcttgccag   4380
aagagatagg ggatttagac aacttacggg tgtttgatgc cagtgatact ctaattttac   4440
gacctccgtc ttccatcata cgcttgaaca aacttataat cttgatgttt cgaggcttca   4500
aagatggagt gcactttgag ttccctcctg tggctgaagg attacactca ttggaatatc   4560
tgaatctcag ttactgcaat ctaatagatg gaggacttcc ggaagagatt ggatccttat   4620
cctctttgaa aaagttggat ctcagtagaa ataattttga gcatttgcct tcaagtatag   4680
cccaacttgg tgctcttcaa tccttagact taaaagattg ccagaggctt acacagctac   4740
cagaacttcc cccagaatta aatgaattgc atgtagattg tcatatggct ctgaaattta   4800
tccattattt agtaacaaag agaaagaaac tacatagagt gaaacttgat gatgcacaca   4860
atgatactat gtacaatttg tttgcatata ccatgtttca gaatatctct tccatgaggc   4920
atgacatctc tgcttcagat tccttgtcac taacagtatt taccggtcaa ccgtatcctg   4980
aaaagatccc gagttggttc caccatcagg gttgggatag tagtgtatca gtcaatttgc   5040
ctgaaaattg gtatatacct gataaattct tgggatttgc tgtatgttac tctcgtagct   5100
taattgacac aacagctcac ttgattcccg tatgtgatga caagatgtcg cgcatgaccc   5160
agaaacttgc cttatcagaa tgtgatacag aatcatccaa ctattcagaa tgggatatac   5220
attttttctt tgtacctttt gctggcttat gggatacatc taaggcaaat ggaaaaacac   5280
caaatgatta tgggattatt aggctatctt tttctggaga agagaagatg tatggacttc   5340
gtttgttgta taaagaagga ccagaggtta atgccttgtt acaaatgagg gaaaatagca   5400
atgaaccaac agaacattcc actgggataa ggaggactca atataacaac agaacttcct   5460
tttatgtaag tctctacttc tattagctac aaagtcttct tccaaaatca atactccatc   5520
cgttccagtt tatgtgaacc tattttttgt tcgtccattc taaaaagaat gacccctttc   5580
taaatttgga aataattttg gttaaactta taattctacc attaacgaga agcttttata   5640
accacacaaa tattctgggg cccttttga attgtttagg accataaatt ccaaaagtcc   5700
tcatttttc ttaaactccg tgcccaatca aacaagttca cgtaaattgg aacggaggga   5760
atatattttt tcttctcatt cttttcccct atttacagga gctcatcaat gggtga       5816
```

<210> SEQ ID NO 22

-continued

```
<211> LENGTH: 6428
<212> TYPE: DNA
<213> ORGANISM: artificial
<220> FEATURE:
<223> OTHER INFORMATION: cDNA-N/intron construct: E1-E2-I2-E3-I3-E4-
      I4-E5

<400> SEQUENCE: 22

atggcatctt cttcttcttc ttctagatgg agctatgatg ttttcttaag ttttagaggc     60

gaagatactc gaaaaacgtt tacaagtcac ttatacgaag tcttgaatga taagggaata    120

aaaacctttc aagatgataa aaggctagag tacggcgcaa ccatcccagg tgaactctgt    180

aaagctatag aagagtctca atttgccatt gttgttttct cagagaatta tgcaacatca    240

aggtggtgtt tgaatgaact agtgaagatc atggaatgca aaactcgatt taagcaaact    300

gttataccga tattctatga tgtggatcca tcacatgttc ggaaccaaaa ggagagcttt    360

gcaaaagcct ttgaagaaca tgaaacaaag tataaggatg atgttgaggg aatacaaaga    420

tggaggattg ctttaaatga agcggccaat ctcaaaggct cctgtgataa tcgtgacaag    480

actgatgcag actgtattcg acagattgtt gaccaaatct catccaaatt atgcaagatt    540

tctttatctt atttgcaaaa cattgttgga atagatactc atttagagaa aatagaatcc    600

ttactagaga taggaatcaa tggtgttcgg attatgggga tctggggaat gggggggagtc    660

ggtaaaacaa caatagcaag agctatattt gatactcttt taggaagaat ggatagttcc    720

tatcaatttg atggtgcttg tttccttaag gatattaaag aaaacaaacg tggaatgcat    780

tctttgcaaa atgcccttct ctctgaactt ttaagggaaa aagctaatta caataatgag    840

gaggatggaa agcaccaaat ggctagtaga cttcgttcga agaaggtcct aattgtgctt    900

gatgatatag ataataaaga tcattatttg gagtatttag caggtgatct tgattggttt    960

ggtaatggta gtagaattat tataacaact agagacaagc atttgataga gaagaatgat   1020

ataatatatg aggtgactgc actacccgat catgaatcca ttcaattgtt caaacaacat   1080

gctttcggaa aagaagttcc aaatgagaat tttgagaagc tttcattaga ggtagtaaat   1140

tatgctaaag gccttccttt agccctcaaa gtgtggggtt ctttgctgca taacctacga   1200

ttaactgaat ggaaaagtgc tatagagcac atgaaaaata actcttattc tggaattatt   1260

gataagctca aaataagtta tgatggatta gagcccaaac aacaagagat gtttttagat   1320

atagcatgct tcttgcgagg ggaagaaaaa gattacatcc tacaaatcct tgagagttgt   1380

catattggag ctgaatacgg gttacgtatt ttaattgaca aatctcttgt gttcatctct   1440

gaatataatc aggttcaaat gcatgactta atacaggata tgggtaaata tatagtgaat   1500

tttcaaaaag atcccggaga acgtagcaga ttatggctcg ccaaggaagt cgaagaagtg   1560

atgagcaaca acacagtaag taagctaaat aatgcaataa tatttaattt ctaattttat   1620

attctaaaga cacatagggc agtcaattcc agttatttgt tcctcttgct tcatagtctt   1680

gacggtacat cattttagtt gtttacttta gttagtagga gatataaaag taatattaat   1740

tacctcatta gtaaaaaaaa acattaattg cctaatttgt ttagtagccg ctttaattta   1800

cgttccctaa ttcgtttttt cttatatttt ttagggatgg attagtctag tagccactta   1860

atctgtttga tccaatgtct ttctttggat taacttgaaa attttatgac attatatata   1920

ataactcaat cattcattca ctttaccatt attatttttt atataaagtt acaatttatt   1980

ggtactgttt cagttacaat tactttccaa catggaaaac ttataaactg gactccaata   2040

aacttataag aaaaatgtaa taatagaaaa taaaattata taattaatta caaaaaagta   2100
```

-continued

```
tttttctgaa gtaacatcag tatttcttaa aaagaatcca attaacattg tatcttaaac   2160
tttggtattg taaggcgtga gaaagtagtg gccttatttc aatttgacgt gaagaataga   2220
atgcctttta acgacataag ggaagggggc aagaataagt ttctattcag ccgggctcga   2280
agcagaaggt agaacgtaat atcttttgtt ggttcagctc atcaagctat tacaaaagag   2340
tccgctcata ttaacaaacg gagtttatac gacatttgaa attatacttt gtagactaat   2400
gatcttcttg ttaccagggg accatggcaa tggaagcaat ttgggtttct tcttattcta   2460
gtactctacg ctttagcaat caggccgtga aaaatatgaa aaggcttagg gtatttaaca   2520
tggggaggtc gtcgacacat tatgccatcg attatctgcc caacaacttg cgttgttttg   2580
tttgcactaa ctatccttgg gagtcatttc catctacatt tgaactcaaa atgcttgttc   2640
acctccaact ccgacacaat tctctgcgtc atttatggac agaaacaaag gtacaatagc   2700
ttgaattcta ttttgttgtc atttattttt ctctctaact atctttgtcc tttaatttgg   2760
tgataatgaa caaatattat tgttttttgt tatgaaacaa taaaagaaga agaacaatat   2820
tgcagagaaa gagggagatg gaattcttat tgaattttgg ggcgatttac aatggggtaa   2880
gacccctcta tttacagggg aaaaataact tagcctcaaa ataaagctct ttaaaagata   2940
gacattcact ctaaatagaa ttctattata acacttttgg cgtacttcct tttttggcta   3000
gaattatgat acatgtcttt aaatgaacag aagttgcttt tgtaatttat caggacttat   3060
gttgaaactt atgaaaattg ttattgttta tgttgtctaa tactaaatat aaaatacaat   3120
aatattttat cgtaattttt taaaaatttg tcaaataatg caaatgaaaa attaaatttt   3180
ttggtccttt aaaaatttga gaatgaaaaa gtacgagtta tacttcctaa aagtttgata   3240
gtgaataata tgtaaaattt aaagaatgac taatattgga ctaatacttt aaaacaaata   3300
acttaatata caaattatag cgagacattt tcattcgttg tactgaatgc aagaaagaaa   3360
ggaaaaaaaa actcatttat aatatagttt gtcttctact attttacctt attgcttcaa   3420
atttgtattt tatcgatttt gctatatctt atgatttttt tcacggtcaa tattcttctt   3480
acaagaataa attttatata cctcaagtgt tttgtcaatt tgataaataa tttttcttat   3540
atgatgaact tgtaaaataa tagaattgga ttcttttgct aattagttaa ttcaacgact   3600
taattattta ttctcaacat taaaggaaat aatttagttt ttattaattc aaactcttag   3660
tatttgctca ttctaatttt cagtccaata agaattcaat tttcaaatag taagaaaagt   3720
catatatttt gaattttatg ttttccgaag cattgtttgt ttgtttaact ctacgggagt   3780
tttctaactc acattttgta taataaaatt ttttgagtag tagttcagta caactctaat   3840
attaatgggc tttaaataag gaaatatata ttacgtaaaa atttaaatca ttttaaagtt   3900
ctttcctacc aagtaaataa gggaaaattt aataacaaaa atttagttga ttttaaaatc   3960
ctaaatatta gaaaattaac ttaaaatata atttcgtcta gtgtaaaatt tatttttaaa   4020
gggtaaaaaa gacgaacgac attaagagcc tttgtaattt taatatagta taaatataaa   4080
taatttacct ttattcagtt tcttaacaag taattttcca tatataaaaa ataaatttct   4140
atattcacac aaaaataatg tgttggccct cgtaattcaa atactatcat tcatttcttg   4200
tcgagggagt agtaaatact tttaggaaag ttagcaataa gtaatcaaga aatcaagaaa   4260
acagaggtca tttgatgccc acaaatacaa atgaaaaaac aaaacaaatg ttacgaaaca   4320
ataaaagaac aagaatagcc tcaaagtaaa actctctgat agacatttac tctaaataga   4380
attctattta taacaatcaa aaagtttcta catttataga tagctccact agccaaatat   4440
tttattattg gaatcagcaa aataggttgt ttcttttttt attctcattc tgtctgtgtt   4500
```

-continued

```
ctaaacagca tttgccgtct ctacggagga tagatctcag ctggtctaaa agattgacgc   4560
gaacaccaga tttcacgggg atgccaaatt tggagtatgt gaatttgtat caatgtagta   4620
atcttgaaga agttcaccat tccctgggat gttgcagcaa agtcattggt ttatatttga   4680
atgattgtaa aagccttaag aggtttccat gtgttaacgt ggaatctctt gaatatctgg   4740
gtctaagaag ttgcgatagt ttagagaaat tgccagaaat ctacgggaga atgaagccgg   4800
agatacagat tcacatgcaa ggctctggga taagggaact accatcatct atttttcagt   4860
acaaaactca tgttaccaag ctattgttgt ggaatatgaa aaaccttgta gctcttccaa   4920
gcagcatatg taggttgaaa agtttggtta gtctgagtgt gtcgggttgc tcaaaacttg   4980
aaagcttgcc agaagagata ggggatttag acaacttacg ggtgtttgat gccagtgata   5040
ctctaatttt acgacctccg tcttccatca tacgcttgaa caaacttata atcttgatgt   5100
ttcgaggctt caaagatgga gtgcactttg agttccctcc tgtggctgaa ggattacact   5160
cattggaata tctgaatctc agttactgca atctaataga tggaggactt ccggaagaga   5220
ttggatcctt atcctctttg aaaaagttgg atctcagtag aaataatttt gagcatttgc   5280
cttcaagtat agcccaactt ggtgctcttc aatccttaga cttaaaagat tgccagaggc   5340
ttacacagct accagaactt cccccagaat taaatgaatt gcatgtagat tgtcatatgg   5400
ctctgaaatt tatccattat ttagtaacaa agagaaagaa actacataga gtgaaacttg   5460
atgatgcaca caatgatact atgtacaatt tgtttgcata taccatgttt cagaatatct   5520
cttccatgag gcatgacatc tctgcttcag attccttgtc actaacagta tttaccggtc   5580
aaccgtatcc tgaaaagatc ccgagttggt tccaccatca gggttgggat agtagtgtat   5640
cagtcaattt gcctgaaaat tggtatatac ctgataaatt cttgggattt gctgtatgtt   5700
actctcgtag cttaattgac acaacagctc acttgattcc cgtatgtgat gacaagatgt   5760
cgcgcatgac ccagaaactt gccttatcag aatgtgatac agaatcatcc aactattcag   5820
aatgggatat acatttttc tttgtacctt ttgctggctt atgggataca tctaaggcaa   5880
atggaaaaac accaaatgat tatgggatta ttaggctatc tttttctgga gaagagaaga   5940
tgtatggact tcgtttgttg tataaagaag gaccagaggt taatgccttg ttacaaatga   6000
gggaaaatag caatgaacca acagaacatt ccactgggat aaggaggact caatataaca   6060
acagaacttc cttttatgta agtctctact tctattagct acaaagtctt cttccaaaat   6120
caatactcca tccgttccag tttatgtgaa cctatttttt gttcgtccat tctaaaaaga   6180
atgacccctt tctaaatttg gaaataattt tggttaaact tataattcta ccattaacga   6240
gaagctttta taaccacaca aatattctgg ggcccttttt gaattgttta ggaccataaa   6300
ttccaaaagt cctcattttt tcttaaactc cgtgcccaat caaacaagtt cacgtaaatt   6360
ggaacggagg gaatatattt tttcttctca ttcttttccc ctatttacag gagctcatca   6420
atgggtga                                                            6428
```